(12) United States Patent
Eckhardt et al.

(10) Patent No.: US 11,851,418 B2
(45) Date of Patent: Dec. 26, 2023

(54) HETEROAROMATIC CARBOXAMIDE DERIVATIVES AS PLASMA KALLIKREIN INHIBITORS

(71) Applicant: Boehringer Ingelheim International GmbH, Ingelheim am Rhein (DE)

(72) Inventors: Matthias Eckhardt, Biberach an der Riss (DE); Maude Giroud, Basel (CH); Camilla Mayer, Warthausen (DE); Holger Wagner, Mettenberg (DE); Dieter Wiedenmayer, Bieberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 148 days.

(21) Appl. No.: 17/173,212

(22) Filed: Feb. 11, 2021

(65) Prior Publication Data

US 2021/0276976 A1 Sep. 9, 2021

(30) Foreign Application Priority Data

Feb. 13, 2020 (EP) .................................. 20157257

(51) Int. Cl.
  *C07D 401/14* (2006.01)
  *C07D 403/14* (2006.01)
  *A61K 45/06* (2006.01)

(52) U.S. Cl.
  CPC ............ *C07D 401/14* (2013.01); *A61K 45/06* (2013.01); *C07D 403/14* (2013.01)

(58) Field of Classification Search
  CPC ....................... C07D 401/14; C07D 403/14
  See application file for complete search history.

(56) References Cited

U.S. PATENT DOCUMENTS

| | | | |
|---|---|---|---|
| 10,399,961 B2 | 9/2019 | Frattini et al. | |
| 10,501,440 B2 | 12/2019 | Frattini et al. | |
| 10,640,486 B2 | 5/2020 | Frattini et al. | |
| 10,695,334 B2 | 6/2020 | Eckhardt et al. | |
| 2005/0090529 A1 | 4/2005 | McAlpine et al. | |
| 2020/0054617 A1 | 2/2020 | Eckhardt et al. | |
| 2021/0276976 A1 | 9/2021 | Eckhardt et al. | |
| 2021/0292301 A1 | 9/2021 | Eckhardt et al. | |

FOREIGN PATENT DOCUMENTS

| | | | |
|---|---|---|---|
| JP | 2005089362 A | 4/2005 | |
| WO | 2002064545 A1 | 8/2002 | |
| WO | 2009097141 A1 | 8/2009 | |
| WO | 2013111107 A1 | 8/2013 | |
| WO | 2013111108 A1 | 8/2013 | |
| WO | 2014188211 A1 | 11/2014 | |
| WO | 2017072020 A1 | 5/2017 | |
| WO | 2017072021 A1 | 5/2017 | |
| WO | 2017207983 A1 | 12/2017 | |
| WO | 2018011628 A1 | 1/2018 | |
| WO | 2018192866 A1 | 10/2018 | |

OTHER PUBLICATIONS

International Search Report for PCT/EP2016/075221 dated Jan. 18, 2017.
Written Opinion for PCT/EP2016/075221 dated Jan. 18, 2017.
Keener, Plasma Kallikrein and Diabetic Macular Edema, Curr. Diab. Rep. 2010.
International Search Report for PCT/EP2016/075222 dated Oct. 25, 2016.
Written Opinion for PCT/EP2016/075222 dated Oct. 26, 2016.
International Search Report and Written Opinion for PCT/EP2018059633 dated Jul. 6, 2018.
Japtap, Heck Reaction, Catalysts, 2017.
Hashiguchi, Asymmetric Transfer Hrydogenation of Aromatic Ketones Catalyzed by Chiral Ruthenium (II) Complexes, J. Am. Chem. Soc, 1995, vol. 117, p. 7562-7563.
Li, Enantioselective, Organocataltyic Reduction of Ketones using Bifunctional Thiorea-Amine Catalysts, Organic Letters, 2010, vol. 12, p. 1756-1759.
Kim, Asymmetric Reductions involving Borohydrides, Organic Research and Development, 2006, vol. 10, p. 949-958.
Nakamura, Recent Developments in asymmetric reduction of ketones with biocatalysts, Tetrahedron: Asymmetry, 2003, vol. 14, p. 2659-2681.
Yoshimura, Recent topics in catalytic asymmetric hydrogenation of ketones, Tetrahedron Letters, 2014, vol. 55, p. 3635-3640.
Biagetti, Synthesis and structure-activity relationship of N-(3-azabicyclo[3.1.0]hex-6-ylmethyl)-5-(2-pyridinyl)-1,3-thiazol-2-amines derivatives as NPY Y5 antagonists, Bioorganic & Medicinal Chem Letters, 2010, vol. 20, p. 4741-4744.
International Search Report and Written Opinion for PCT/EP2019/071855 dated Sep. 1, 2019.
Database Pub Chem, NCBI, No. 8248531, 2014.
Mormino et al., "Copper-Mediated Perfluoroalkylation of Heteroaryl Bromides with (phen)CuRf", Organic Letters, 2014, vol. 16, No. 6, pp. 1744-1747.
PubChem Substance Record SID 299284535; (2016) 5 pgs.
PubChem Substance Record SID 299284560; (2016) 5 pgs.

*Primary Examiner* — Brian E McDowell

(74) *Attorney, Agent, or Firm* — Shelley A. Jones

(57) ABSTRACT

Disclosed are heteroaromatic carboxamides of formula (I),

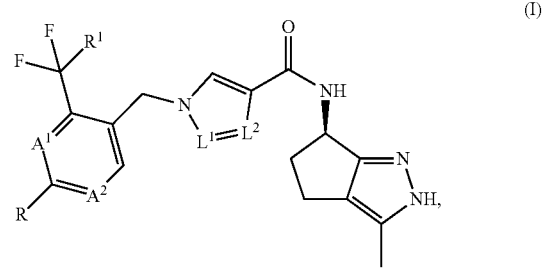

wherein R, $R^1$, $A^1$, $A^2$, $L^1$, and $L^2$ are as defined herein, and pharmaceutically acceptable salts thereof. Also disclosed are methods of using the compounds of formula (I) for treatment of diseases, which can be influenced by inhibition of plasma kallikrein.

10 Claims, No Drawings

HETEROAROMATIC CARBOXAMIDE DERIVATIVES AS PLASMA KALLIKREIN INHIBITORS

FIELD OF THE INVENTION

This invention relates to novel heteroaromatic carboxamide derivatives, and pharmaceutically acceptable salts thereof, that are plasma kallikrein inhibitors. In addition, the invention relates to pharmaceutical compositions and combinations comprising said compounds and to their use in methods for the treatment of diseases which can be influenced by the inhibition of plasma kallikrein. Particularly, the pharmaceutical compositions of the invention are suitable for the prophylaxis and/or therapy of diabetic complications, ocular diseases and edema-associated diseases, in particular diabetic macular edema, age-related macular degeneration, choroidal neovascularization, hereditary angioedema, and brain edema after stroke.

BACKGROUND OF THE INVENTION

Plasma kallikrein (PKK) is a trypsin-like serine protease secreted by hepatocytes in the liver as an inactive plasma prekallikrein that circulates in plasma either as a free zymogen or as a heterodimer complex bound to high molecular weight kininogen which is activated to give the active PKK that can liberate kinins from kininogens in addition to processing other substrates. Kinins are potent mediators of inflammation that act through G protein-coupled receptors such as bradykinin receptors.

PKK is thought to play a role in a number of inflammatory disorders and may have numerous implications in disorders such as hereditary angioedema (HAE), retinopathy or diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), choroidal neovascularization (CNV; e.g. non-exudative choroidal neovascularization), posterior vitreous detachment (PVD), ischemic reperfusion injuries, e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke (including edema in the central nervous system after stroke), myocardial infarction, acquired angioedema, drug-related edema (including ACE-inhibitor induced edema as well as tissue plasminogen activator (tPA)-induced angioedemas), high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associated with injury or surgery, brain aneurysm, arterio-venous malformation, reduction of blood losses during surgical procedures (e.g. cardiothoracic surgery, such as cardiopulmonary bypass or coronary artery bypass grafting), itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), cerebral hemorrhage, blood coagulation disorders such as thrombosis, deep vein thrombosis, coagulation from post fibrinolytic treatments, angina, angioedema, sepsis, arthritis (e.g. rheumatoid arthritis, osteoarthritis, infection arthritis), lupus, gout, psoriasis, inflammatory bowel diseases (IBDs, such as ulcerative colitis (UC) and Crohn's disease (CD)), diabetes, diabetic complications, complications arising from metabolic syndrome, infectious diseases, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma), allergic edema e.g. airflow obstruction in chronic allergic sinusitis or perennial rhinitis; airflow obstruction in acute asthma; serositis associated with systemic lupus erythematosus (SLE), acute respiratory distress syndrome (ARDS), coronavirus disease 2019 (COVID-19) related pneumonia, fibrotic disease, hepatic fibrosis, nonalcoholic steatohepatitis (NASH), renal injury, and other diseases. PKK is also thought to play an important role in hypersensitivity reactions and thrombosis during hemodialysis.

PKK inhibitors, like the compounds of the present invention, are considered to be useful in the treatment of a wide range of disorders, e.g. as mentioned hereinbefore; in particular, they should have utility as a treatment to reduce retinal vascular permeability associated with diabetic retinopathy and diabetic macular edema or edema-associated diseases.

PKK inhibitors should be particularly useful in the treatment of edema formation in diseases, e.g. edema formation related to ischemic reperfusion injuries, retinopathy or edema-associated diseases, such as hereditary angioedema, macular edema and brain edema. PKK inhibitors are considered to be especially useful in the treatment of retinopathy, e.g. retinopathy associated with diabetes and/or hypertension, and in the treatment of macular edema, e.g. macular edema associated with diabetes and/or hypertension.

Other complications of diabetes such as cerebral hemorrhage, nephropathy, cardiomyopathy and neuropathy, all of which have associations with PKK, may also be considered as targets for a PKK inhibitor.

PKK inhibitors suitable for therapeutic and/or prophylactic use should bind potently and with high selectivity to PKK. They should be well absorbed from the gastrointestinal tract, be sufficiently metabolically stable and possess favorable pharmacokinetic properties. They should be non-toxic and demonstrate few side-effects.

Low molecular weight PKK inhibitors are known in the art, for example, the compounds disclosed in WO 2009/097141, WO 2013/111107, WO 2013/111108, WO 2014/188211, WO 2017/072020, WO 2017/072021, and WO 2018/192866.

SUMMARY OF THE INVENTION

In a first aspect, the present invention relates to a compound of formula (I)

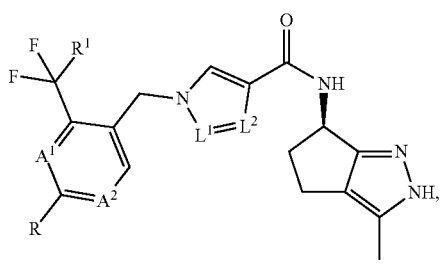

(I)

wherein
R is selected from the group R-G1 consisting of

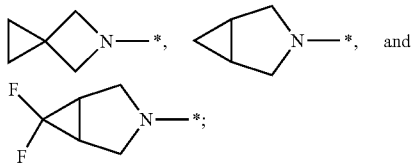

and $R^1$ is selected from the group $R^1$-G1 consisting of H and F; the moiety $=A^1$-CR$=A^2$- is selected from the group A-G1 consisting of =N—CR=N—, =N—CR=CH— and =CH—CR=N—; and
the moiety -$L^1$=$L^2$- is selected from the group L-G1 consisting of —N=N—, —N=CH— and —CH=N—;
the isoforms, tautomers, stereoisomers, metabolites, prodrugs, solvates, hydrates, cocrystals and the salts thereof, particularly the pharmaceutically acceptable cocrystals and salts thereof, or the combinations thereof.

In a second aspect, the present invention relates to a pharmaceutical composition comprising one or more compounds of formula (I), as defined hereinbefore or hereinafter, and/or their tautomers or pharmaceutically acceptable salts thereof, optionally together with one or more inert carriers and/or diluents.

In a third aspect, the present invention relates to a pharmaceutical composition comprising one or more compounds of formula (I), as defined hereinbefore or hereinafter, and/or their tautomers or pharmaceutically acceptable salts thereof, and one or more additional therapeutic agents, optionally together with one or more inert carriers and/or diluents.

In a fourth aspect, the present invention relates to a compound of formula (I), as defined hereinbefore or hereinafter, and/or its tautomers or a pharmaceutically acceptable salt thereof for use as a medicament.

In a fifth aspect, the present invention relates to a method for the treatment, i.e. therapy and/or prevention, of diseases or conditions which can be influenced by the inhibition of plasma kallikrein in a patient in need thereof, the method comprising administering to the patient one or more compounds of formula (I), as defined hereinbefore or hereinafter, and/or their tautomers or pharmaceutically acceptable salts thereof.

In addition, the present invention relates to the use of one or more compounds of formula (I), as defined hereinbefore or hereinafter, and/or their tautomers or pharmaceutically acceptable salts thereof in the manufacture of a medicament for the treatment, i.e. therapy and/or prevention, of diseases or conditions which can be influenced by the inhibition of plasma kallikrein.

Furthermore, the present invention relates to a compound of formula (I), as defined hereinbefore or hereinafter, and/or its tautomers or a pharmaceutically acceptable salt thereof for use in a method for the treatment, i.e. therapy and/or prevention, of diseases or conditions which can be influenced by the inhibition of plasma kallikrein, in a patient in need thereof.

Further aspects of the present invention will become apparent to the person skilled in the art directly from the foregoing and following description and the examples.

General Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of formula (I) according to the present invention including their tautomers, stereoisomers and mixtures thereof and the salts thereof, in particular the pharmaceutically acceptable salts thereof, and the solvates, hydrates and cocrystals of such compounds, in particular the pharmaceutically acceptable cocrystals thereof, including the solvates, hydrates and cocrystals of such tautomers, stereoisomers and salts thereof.

Also, unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof, and solvates thereof, such as for instance hydrates, including solvates of the free compounds or solvates of a salt of the compound, and cocrystals thereof, including pharmaceutically acceptable cocrystals thereof and cocrystals of the free compounds or of a salt thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, EtOAc, EtOH, isopropanol, or MeCN, or a mixture thereof.

Salts of other acids than those mentioned above which for example are useful for purifying or isolating the compounds of the present invention (e.g. trifluoro acetate salts) also comprise a part of the invention.

As used herein, "pharmaceutically acceptable cocrystals" refer to derivatives of the disclosed compounds wherein the parent compound is modified by making a cocrystal thereof with the help of one or more coformers. Also, cocrystals of solvates and/or salts of the disclosed compounds are encompassed.

For example, coformers include hydrogen bond donors, such as carboxylic acids, and hydrogen bond acceptors, such as amines and amides.

The pharmaceutically acceptable cocrystals of the present invention can be synthesized from the parent compound by methods known to the one skilled in the art, including solid-based methods, such as solid state grinding, melt extrusion and melt crystallization, and liquid-based methods, such as solution crystallization, solvent evaporation, cooling crystallization, supercritical fluid assisted crystallization, ultrasound assisted crystallization, spray drying, liquid assisted grinding and planetary milling.

In case a compound of the present invention is depicted in form of a chemical name and as a formula, in case of any discrepancy the formula shall prevail.

In the groups, radicals, or moieties defined below, the number of carbon atoms is often specified preceding the group, for example, $C_{1-6}$-alkyl means an alkyl group or radical having 1 to 6 carbon atoms.

An asterisk may be used in sub-formulas to indicate the bond which is connected to the core molecule as defined. In the case of more than one attachment point, i.e. more than one asterisk, in a sub-formula, the asterisks may be further specified by a bracketed designation of the connected part of the core molecule.

The numeration of the atoms of a substituent starts with the atom which is closest to the core or to the group to which the substituent is attached.

For example, the term "3-carboxypropyl-group" represents the following substituent:

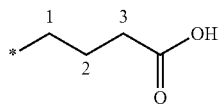 [SMILES: *CCCC(=O)O]

wherein the carboxy group is attached to the third carbon atom of the propyl group. The terms "1-methylpropyl-", "2,2-dimethylpropyl-" or "cyclopropylmethyl-" group represent the following groups:

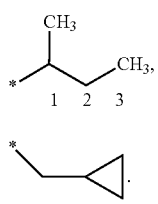

The term "$C_{1-n}$alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$.

The terms "treatment" and "treating" as used herein embrace both therapeutic, i.e. curative and/or palliative, and preventive, i.e. prophylactic, treatment.

Therapeutic treatment refers to the treatment of patients having already developed one or more of said conditions in manifest, acute or chronic form. Therapeutic treatment may be symptomatic treatment in order to relieve the symptoms of the specific indication or causal treatment in order to reverse or partially reverse the conditions of the indication or to stop or slow down progression of the disease.

Preventive treatment ("prevention") refers to the treatment of patients at risk of developing one or more of said conditions, prior to the clinical onset of the disease in order to reduce said risk.

The terms "treatment" and "treating" include the administration of one or more active compounds in order to prevent or delay the onset of the symptoms or complications and to prevent or delay the development of the disease, condition or disorder and/or in order to eliminate or control the disease, condition or disorder as well as to alleviate the symptoms or complications associated with the disease, condition or disorder.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

DETAILED DESCRIPTION OF THE INVENTION

The present invention discloses novel heteroaromatic carboxamide derivatives, which are effective plasma kallikrein (PKK) inhibitors and possess suitable pharmacological and pharmacokinetic properties to use them as medicaments for the treatment of diseases and/or conditions that may be influenced by PKK inhibition, including but not limited to diabetic complications, ocular diseases and edema-associated diseases, in particular diabetic macular edema, age-related macular degeneration, choroidal neovascularization, hereditary angioedema, and brain edema after stroke. The compounds of the present invention may provide several advantages, such as enhanced potency, high metabolic and/or chemical stability, high selectivity, safety and tolerability, enhanced solubility, enhanced permeability, desirable plasma protein binding, enhanced bioavailability, improved pharmacokinetic profiles, and the possibility to form stable salts.

Compounds of the Invention

In a first aspect of the present invention, it is found that compounds of formula (I)

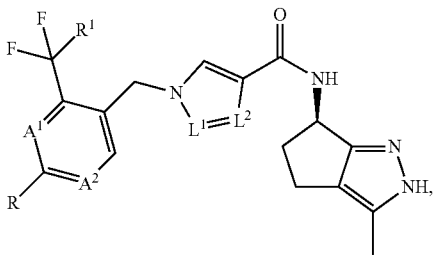

wherein R, R$^1$, A$^1$, A$^2$, L$^1$, and L$^2$ are defined as hereinbefore and hereinafter, are potent inhibitors of PKK and exhibit favorable properties with regard to selectivity, safety and tolerability, metabolic and/or chemical stability, pharmacokinetic and physicochemical characteristics, solubility, permeability, plasma protein binding, bioavailability and/or the possibility to form stable salts. In particular, they provide an advantageous combination of high potency on human PKK and significant selectivity, e.g. vs. various serine proteases, such as human tissue kallikrein 1 (TK1), as well as advantageous membrane permeabilities at physiologically relevant pH values. In addition, advantageous safety features, such as low potential of mutagenicity and low propensity for mechanism based inhibition of cytochrome P450 (CYP) 3A4, are exhibited.

Therefore, the compounds of formula (I), as defined hereinbefore or hereinafter, or pharmaceutically acceptable salts thereof are expected to be useful in the treatment of diseases and/or conditions that can be influenced by PKK inhibition.

Thus, according to one aspect of the present invention, a compound of formula (I)

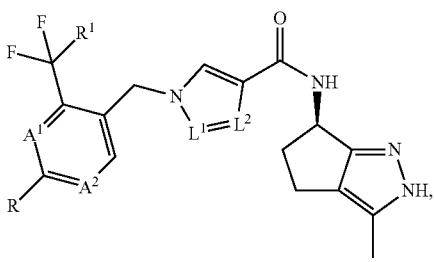

wherein R, R$^1$, A$^1$, A$^2$, L$^1$, and L$^2$ are defined as hereinbefore or hereinafter, is provided
as well as the isoforms, tautomers, stereoisomers, metabolites, prodrugs, solvates, hydrates, cocrystals, and the salts thereof, particularly the pharmaceutically acceptable cocrystals and salts thereof.

Unless otherwise stated, the groups, residues and substituents, particularly R, R$^1$, A$^1$, A$^2$, L$^1$, and L$^2$ are defined as hereinbefore and hereinafter. Preferred meanings of the substituents R, R$^1$, A$^1$, A$^2$, L$^1$, and L$^2$ of formula (I) will be given hereinafter as embodiments of the invention. Any and each of these definitions and embodiments may be combined with one another.

R:

According to one embodiment, R is selected from the group R-G1 consisting of

According to another embodiment, R is selected from the group R-G2 consisting of

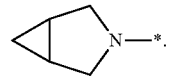

According to another embodiment, R is selected from the group R-G3 consisting of

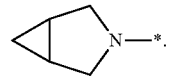

According to another embodiment, R is selected from the group R-G4 consisting of

R$^1$:

According to one embodiment, R$^1$ is selected from the group R$^1$-G1 consisting of H and F.

According to another embodiment, R$^1$ is selected from the group R$^1$-G2 consisting of H.

According to another embodiment, R$^1$ is selected from the group R$^1$-G3 consisting of F.

A$^1$, A$^2$:

According to one embodiment, the moiety =A$^1$-CR=A$^2$- is selected from the group A-G1 consisting of =N—CR=N—, =N—CR=CH— and =CH—CR=N—.

According to another embodiment, the moiety =A$^1$-CR=A$^2$- is selected from the group A-G2 consisting of =N—CR=N—.

According to another embodiment, the moiety =A$^1$-CR=A$^2$- is selected from the group A-G3 consisting of =N—CR=CH—.

According to another embodiment, the moiety =A$^1$-CR=A$^2$- is selected from the group A-G4 consisting of =CH—CR=N—.

For the above definitions of the moiety =A$^1$-CR=A$^2$-, the order of the 3 subunits represents the orientation of the moiety, i.e., for instance in group A-G3, A$^1$ is N and A$^2$ is CH.

L$^1$, L$^2$:

According to one embodiment, -L$^1$=L$^2$- is selected from the group L-G1 consisting of —N=N—, —N=CH— and —CH=N—.

According to another embodiment, -L$^1$=L$^2$- is selected from the group L-G2 consisting of —N=N—.

According to another embodiment, -L¹=L²- is selected from the group L-G3 consisting of —N═CH—.

According to another embodiment, -L¹=L²- is selected from the group L-G4 consisting of —CH═N—.

For the above definitions of the moiety -L¹=L²-, the order of the 2 subunits represents the orientation of the moiety, i.e., for instance in group L-G3, L¹ is N and L² is CH.

Further preferred subgeneric embodiments of the compounds of formula (I) are set forth as embodiments (I-a) to (I-u) in the following Table 1, wherein the above-mentioned substituent definitions are used. For example, the entry -G1 in column R and row (I-a) means that in embodiment (I-a) substituent R is selected from the definition designated R-G1. The same applies analogously to the other variables incorporated in the general formulas.

TABLE 1

| Embodiment | Substituents | | | |
|---|---|---|---|---|
| | R | R¹ | ═A¹—CR═A²— | —L¹═L²— |
| (I-a) | R-G1 | R¹-G1 | A-G1 | L-G1 |
| (I-b) | R-G2 | R¹-G1 | A-G1 | L-G1 |
| (I-c) | R-G3 | R¹-G1 | A-G1 | L-G1 |
| (I-d) | R-G4 | R¹-G1 | A-G1 | L-G1 |
| (I-e) | R-G1 | R¹-G1 | A-G2 | L-G2 |
| (I-f) | R-G1 | R¹-G1 | A-G2 | L-G3 |
| (I-g) | R-G1 | R¹-G1 | A-G2 | L-G4 |
| (I-h) | R-G1 | R¹-G1 | A-G3 | L-G2 |
| (I-i) | R-G1 | R¹-G1 | A-G3 | L-G3 |
| (I-j) | R-G1 | R¹-G1 | A-G3 | L-G4 |
| (I-k) | R-G1 | R¹-G1 | A-G4 | L-G2 |
| (I-m) | R-G1 | R¹-G1 | A-G4 | L-G3 |
| (I-n) | R-G1 | R¹-G1 | A-G4 | L-G4 |
| (I-o) | R-G2 | R¹-G2 | A-G3 | L-G1 |
| (I-p) | R-G3 | R¹-G2 | A-G2 | L-G1 |
| (I-q) | R-G3 | R¹-G2 | A-G3 | L-G1 |
| (I-r) | R-G3 | R¹-G3 | A-G4 | L-G1 |
| (I-s) | R-G4 | R¹-G2 | A-G3 | L-G1 |
| (I-t) | R-G3 | R¹-G2 | A-G3 | L-G3 |
| (I-u) | R-G3 | R¹-G2 | A-G3 | L-G4 |

Particularly preferred compounds, including their tautomers, the salts thereof, or any solvates or hydrates thereof, are

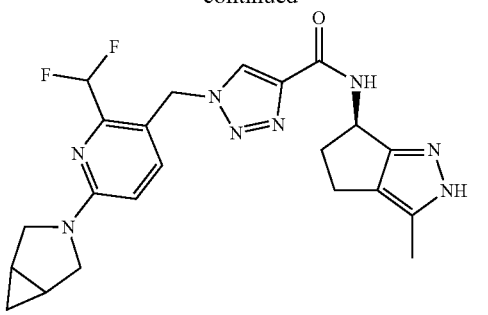

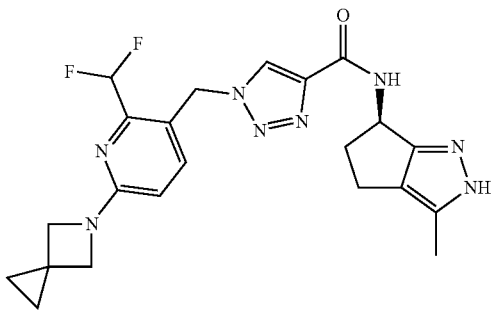

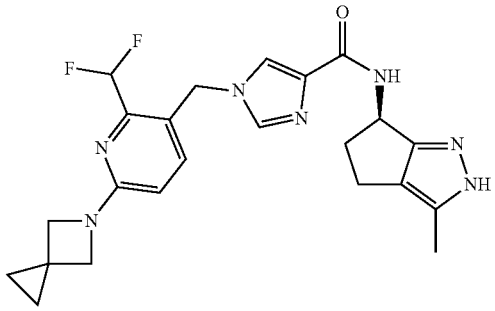

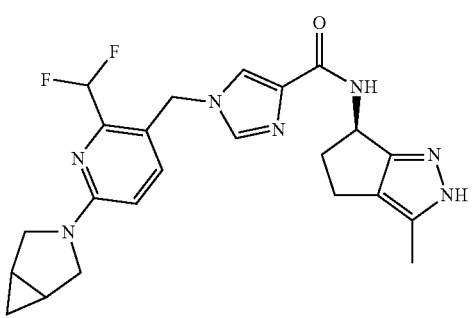

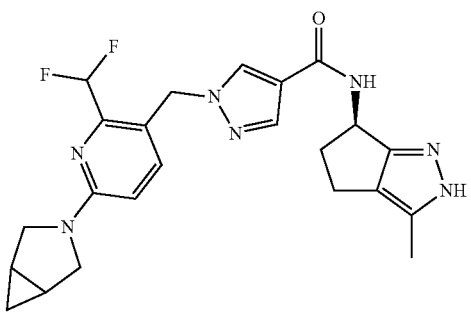

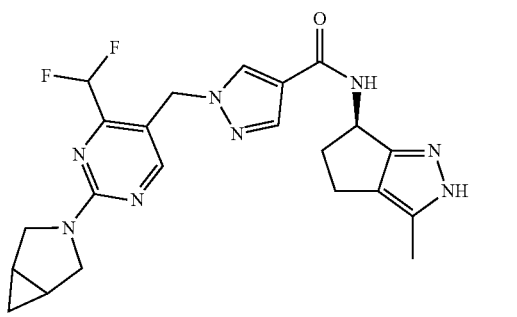
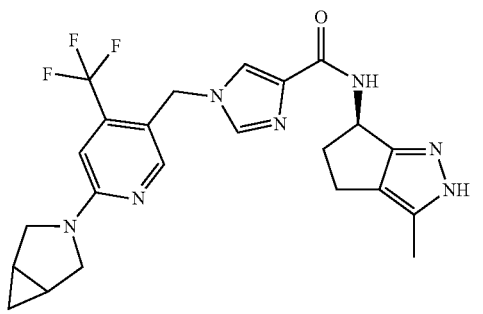
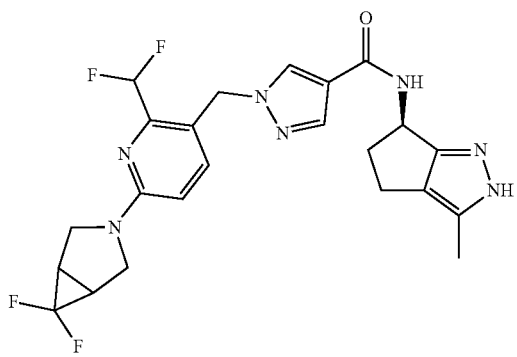
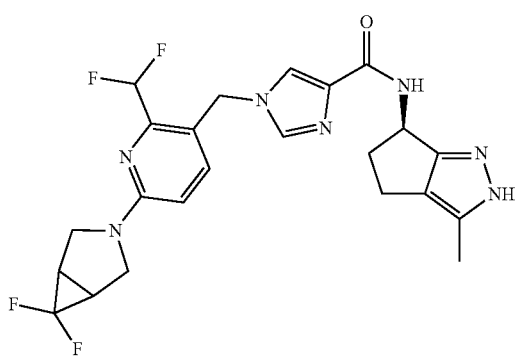
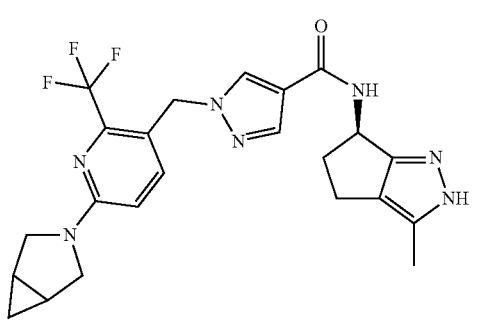
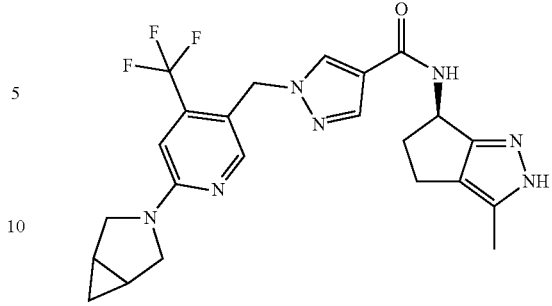

Preparation

The compounds according to the invention and their intermediates may be obtained using methods of synthesis which are known to the one skilled in the art and described in the literature of organic synthesis for example using methods described in "Comprehensive Organic Transformations", $2^{nd}$ Edition, Richard C. Larock, John Wiley & Sons, 2010, and "March's Advanced Organic Chemistry", 7th Edition, Michael B. Smith, John Wiley & Sons, 2013. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled person but are not described in detail here may also be used. The general processes for preparing the compounds according to the invention will become apparent to the skilled person on studying the schemes that follow. Starting compounds are commercially available or may be prepared by methods that are described in the literature or herein, or may be prepared in an analogous or similar manner. Before the reaction is carried out, any corresponding functional groups in the starting compounds may be protected using conventional protecting groups. These protecting groups may be cleaved again at a suitable stage within the reaction sequence using methods familiar to the skilled person and described in the literature for example in "Protecting Groups", $3^{rd}$ Edition, Philip J. Kocienski, Thieme, 2005, and "Protective Groups in Organic Synthesis", $4^{th}$ Edition, Peter G. M. Wuts, Theodora W. Greene, John Wiley & Sons, 2006.

Scheme 1

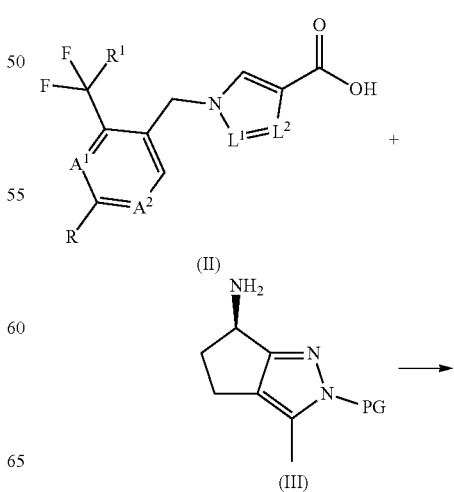

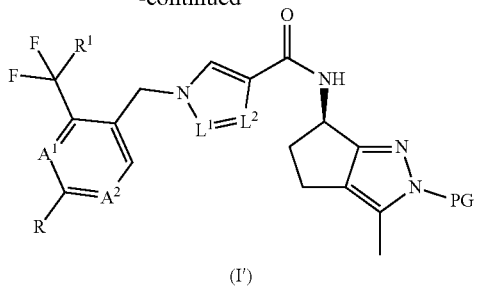

(I')

PG = H or protective group such as CH₂OCH₂CH₂SiMe₃

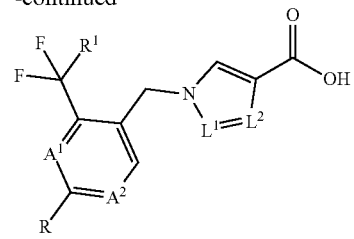

(II)

R⁵ = C₁₋₄-alkyl, benzyl

Scheme 1: Compounds of formula (I') can be prepared by reacting a suitable acid of formula (II) (either as free acid or carboxylate with a suitable metal cation such as Li⁺, Na⁺, K⁺, etc.) and a suitable amine of formula (III) (either as free amine or a salt such as hydrochloride, hydrobromide, etc.) in a suitable solvent (e.g., DCM, THF, 1,4-dioxane, DMF, N,N-dimethylacetamide, and 1-methyl-2-pyrrolidinone) in the presence of a suitable coupling agent (e.g., O-(7-azabenzotriazol-1-yl)-N,N,N',N'-tetramethyluronium-hexafluorophosphate (HATU), O-(benzotriazol-1-yl)-N,N,N',N'-tetramethyluronium tetrafluoroborate (TBTU), (benzotriazol-1-yloxy)tripyrrolidinophosphonium hexafluorophosphate (PyBOP), carbodiimide reagents, etc.) and a base (e.g., triethylamine, N,N-diisopropyl-ethylamine, pyridine, etc.) to form an amide bond; R, R¹, A¹, A², L¹, and L² in Scheme 1 have the meanings as defined hereinbefore. Alternatively, the carboxylic acid is transformed into a carboxylic chloride (using, e.g., oxalyl choride or thionyl chloride in DCM) and coupled as such with amine (III) in the presence of a suited base (e.g., triethylamine, N,N-diisopropyl-ethylamine, pyridine, etc.). In case amine (III) is employed with a protective group on the pyrazole ring (PG is not H) this group is cleaved off afterwards by applying standard procedures reported in the literature of organic chemistry. 2-Trimethylsilylethyloxymethyl and tert-butyl esters are preferably cleaved under acidic conditions with, e.g., TFA or hydrochloric acid in a solvent such as DCM, 1,4-dioxane, isopropanol, or EtOAc. 2-Trimethylsilylethyloxymethyl may also be removed by using a fluoride source (e.g., ⁿBu₄NF) in a suited solvent such as THF. A benzyloxymethyl group can be removed by using hydrogen in the presence of a transition metal such as palladium on carbon. Benzyloxymethyl groups bearing electron donating groups such as methoxy on the phenyl ring may also be cleaved under oxidative conditions (with, e.g., ceric ammonium nitrate (CAN) or 2,3-dichloro-5,6-dicyanoquinone (DDQ)) or acidic conditions (with, e.g., TFA or hydrochloric acid).

Scheme 2

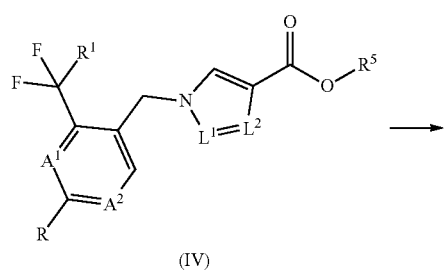

(IV)

Scheme 2: Acids of formula (II), wherein R, R¹, A¹, A², L¹, and L² in Scheme 2 have the meanings as defined hereinbefore, are preferably prepared from the corresponding ester (IV) through hydrolysis or hydrogenolysis depending on the nature of R⁵. Lower alkyl group esters such as ethyl or methyl esters are preferably cleaved by hydrolysis with a hydroxide salt such as NaOH, LiOH, or KOH in a mixture of water and a suitable miscible solvent (e.g., THF, MeOH, EtOH, 1,4-dioxane, or mixtures of these) at ambient or elevated temperature. The acid may be isolated either as a salt with the metal cation or as free acid. A tert-butyl ester is preferably cleaved by treatment with an acid (e.g., hydrochloric acid or TFA) in a suitable solvent (e.g., DCM, 1,4-dioxane, MeOH, EtOH, THF, water, or mixtures of these). A benzyl ester is preferably cleaved by hydrogenolysis with a suitable catalyst (e.g., palladium on carbon) in a suitable solvent (e.g., EtOH, MeOH, THF, DCM, or EtOAc) under an atmosphere of hydrogen (preferably 1 to 5 bar).

Scheme 3

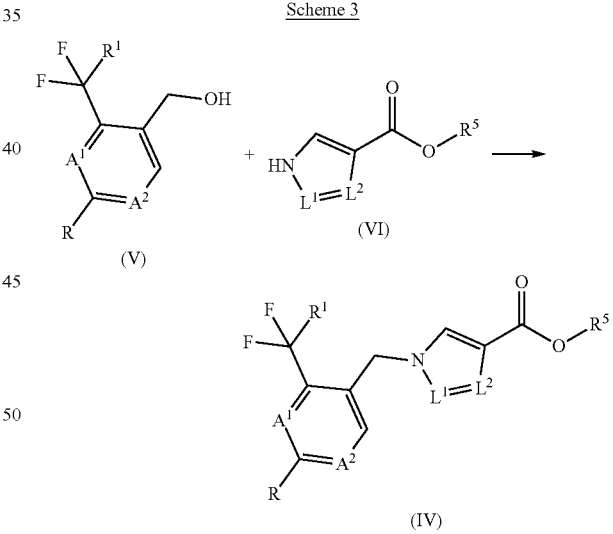

R⁵ = C₁₋₄-alkyl or benzyl

Scheme 3: Some of the compounds (IV) can be prepared by reaction of an alcohol (V) with an ester (VI) employing the conditions of the Mitsunobu reaction (e.g., triphenylphosphine or tri-n-butylphosphine combined with, e.g., diethyl azodicarboxylate (DEAD), diisopropyl azodicarboxylate (DIAD), or di-tert-butyl azodicarboxylate (DBAD) in a solvent such as THF, 1,4-dioxane, toluene, etc.); R, R¹, A¹, A², and L² in Scheme 3 have the meanings as defined hereinbefore. Alcohol (V) may bear the desired residue R on the heteroaromatic ring or a leaving group instead to introduce R later on. Alternatively, some of the compounds (IV) can be obtained by reacting alcohol (V) and ester (VI) in the presence of a Lewis acid or Brønsted acid (e.g., 4-toluenesulfonic acid) in a suited solvent (e.g., MeCN) at elevated temperature (20 to 120° C.).

Scheme 4

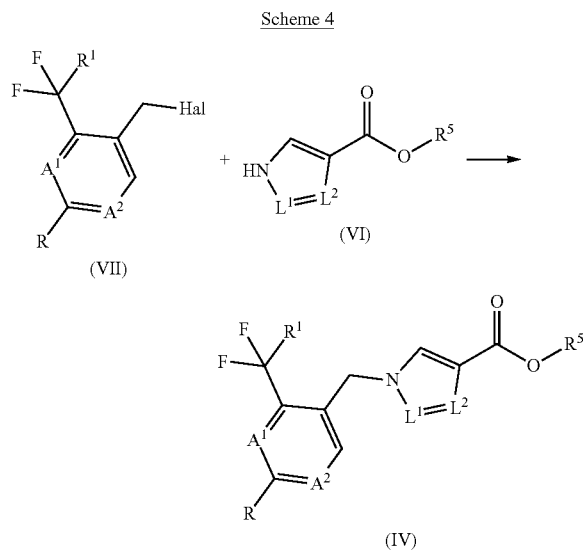

$R^5$ = $C_{1-4}$-alkyl or benzyl
Hal = leaving group such as Cl, Br, I, $OSO_2CH_3$ Scheme 4: Some of the compounds (IV) can also be prepared by reaction of compound (VII), bearing a leaving group at the heteroarylmethyl position such as Cl, Br, or mesyloxy (methanesulfonyloxy), with ester (VI) in the presence of a suitable base (e.g., sodium hydride, cesium carbonate, potassium carbonate, or triethylamine) in a suitable solvent (e.g., THF, DMF); R, $R^1$, $A^1$, $A^2$, $L^1$, and $L^2$ in Scheme 4 have the meanings as defined hereinbefore. Compound (VII) may bear the desired residue R on the heteroaromatic ring or a replaceable group instead to introduce R later on.

Scheme 5

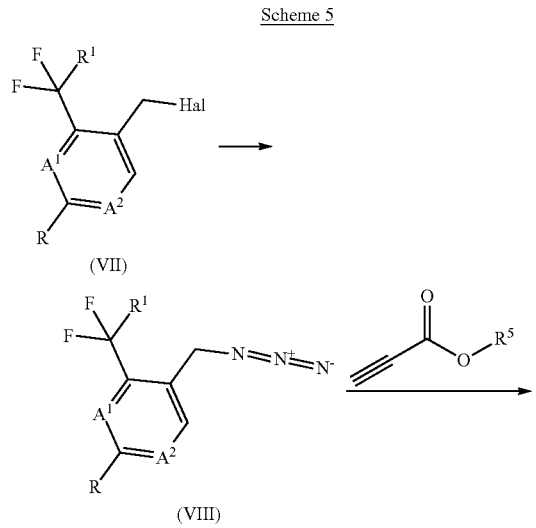

-continued

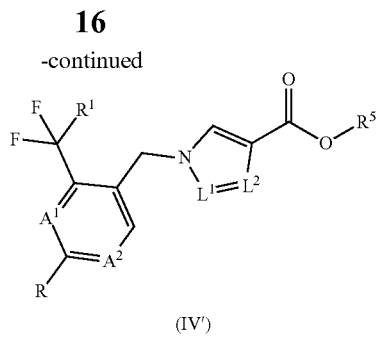

(IV')

$R^5$ = $C_{1-4}$-alkyl or benzyl
Hal = leaving group such as OH, Cl, Br, I, $OSO_2CH_3$ Scheme 5: Some esters of formula (IV'), wherein R, $R^1$, $A^1$, and $A^2$ in Scheme 5 have the meanings defined hereinbefore, can be prepared by treatment of a corresponding alkyl halide (bromide or chloride) or sulfonate (e.g., mesylate) of formula (VII) with sodium azide in DMF or another suitable solvent to give an intermediate of formula (VIII) which is then reacted with a suitable propiolic acid ester under copper mediated conditions (e.g., ethyl propiolate or tert-butyl propiolate with catalytic copper sulfate and sodium ascorbate in water/tert-butanol) to give compound (IV'). Alternatively, azide (VIII) can be obtained from an alcohol of formula (V) (or (VII) wherein Hal is OH) by treatment with diphenylphosphoryl azide in the presence of a suitable base such as DBU in a suitable solvent (e.g., THF or DMF). Compound (VII) may bear the desired residue R on the heteroaromatic ring or a leaving group instead to introduce R later on.

Scheme 6

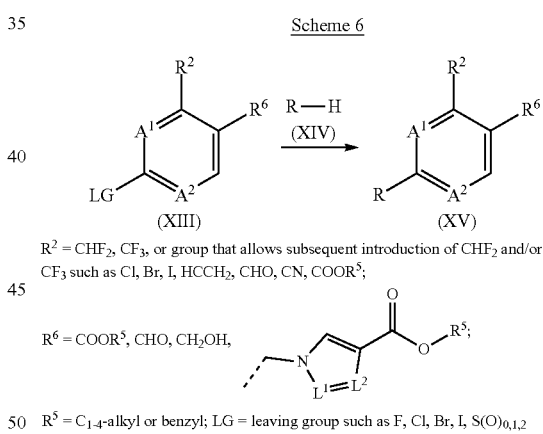

$R^2$ = $CHF_2$, $CF_3$, or group that allows subsequent introduction of $CHF_2$ and/or $CF_3$ such as Cl, Br, I, $HCCH_2$, CHO, CN, $COOR^5$;

$R^6$ = $COOR^5$, CHO, $CH_2OH$, $R^5$ = $C_{1-4}$-alkyl or benzyl; LG = leaving group such as F, Cl, Br, I, $S(O)_{0,1,2}$ Scheme 6: Intermediates of formula (XV) can be prepared from aromatic compound (XIII) and amine (XIV) via either a nucleophilic substitution reaction on the heteroaromatic ring or a transition metal catalyzed coupling reaction; $A^1$, $A^2$ and R in Scheme 6 have the meanings defined hereinbefore. The nucleophilic substitution of a leaving group on the heteroaromatic ring in (XIII) with the N in compound (XIV) can be conducted in the presence of a suitable base (e.g., sodium hydride, cesium carbonate, potassium carbonate, N,N-diisopropyl-ethylamine) in a suitable solvent (e.g., THF, 1,4-dioxane, DMF, DMSO) at ambient or elevated temperature. A transition metal catalyzed coupling reaction is preferably carried out with the chloride, bromide, or iodide of compound (XIII) in analogy to procedures reported in the literature of organic chemistry referred to as Ullmann or Buchwald/Hartwig coupling reaction using suitable copper or palladium salts or complexes thereof, optionally combined with additional ligands, in the presence of a base and in a suited solvent.

a suited vinyl nucleophile, e.g., vinylzincchloride or vinylboronic acid or ester, and the conditions reported for the so-called Negishi (e.g., with Pd(PPh$_3$)$_4$ in THF at 30 to 60° C.) or Suzuki coupling reaction (e.g., with PdCl$_2$(dppf), in the presence of Na$_2$CO$_3$ and water in 1,4-dioxane or DMF at 60 to 110° C.). Compounds (IX) are then submitted to C=C cleaving conditions (e.g., ozonolysis in DCM at −70° C. followed by reductive quenching with PPh$_3$ or Me$_2$S, or dihydroxylation with OsO$_4$ in acetone, tert-butanol, and water at ambient temperature followed by glycol cleavage of the resulting intermediate with NaIO$_4$ in water, tert-butanol, and acetone at ambient temperature). The subsequent deoxofluorination of aldehydes (X) using a suited deoxofluorinat-

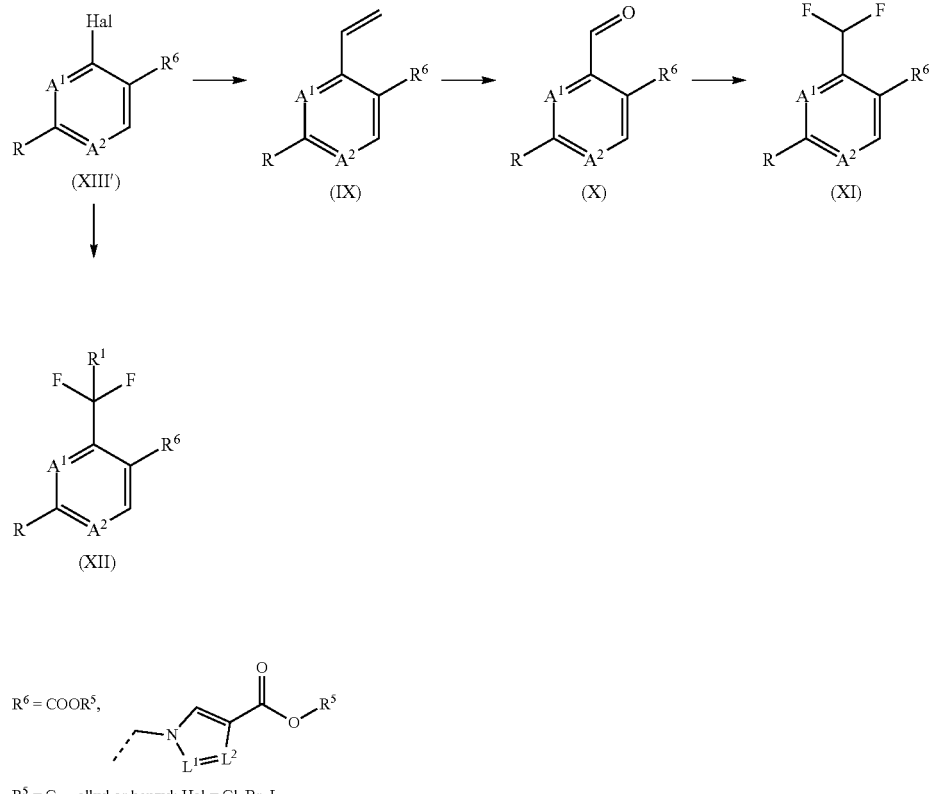

Scheme 7: Intermediates of formula (XII) can be accessed from compounds (XIII') via a transition metal catalyzed coupling reaction with a suited difluoromethyl or trifluoromethyl nucleophile or precursor thereof; R, R$^1$, A$^1$, A$^2$, L$^1$, and L$^2$ in Scheme 7 have the meanings defined hereinbefore. Difluoromethyltrimethylsilane or trifluoromethyltrimethylsilane as the respective nucleophile precursor combined with a copper salt (e.g., CuI) and a base (e.g., CsF or KF) in a suited solvent (e.g., NMP or DMF) at ambient or elevated temperature, 20 to 150° C., may provide compounds of formula (XII). Preformed nucleophiles already incorporating the catalyst such as in F$_3$CCu(phen) (phen=phenanthroline) may be used as well providing compounds (XII) under reported conditions (e.g., in DMF at 80 to 100° C.; see, e.g., Org. Lett. 2014, 16, 1744-1747).

Compounds (XI) may also be obtained from halides (XIII') via a three-step-synthesis sequence. Accordingly, halide (XIII') is vinylated to form compound (IX) employing ing agent (e.g., DAST (Et$_2$NSF$_3$), Deoxofluor ((MeOCH$_2$CH$_2$)$_2$NSF$_3$), or XtalFluor-E ([Et$_2$NSF$_2$]BF$_4$)) in a suited solvent (e.g., DCM or toluene), optionally in the presence of catalytic amounts of methanol or a fluoride salt, at ambient to elevated temperature concludes this sequence.

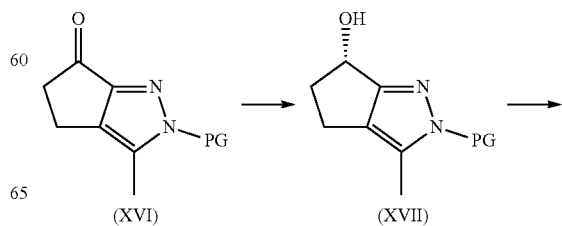

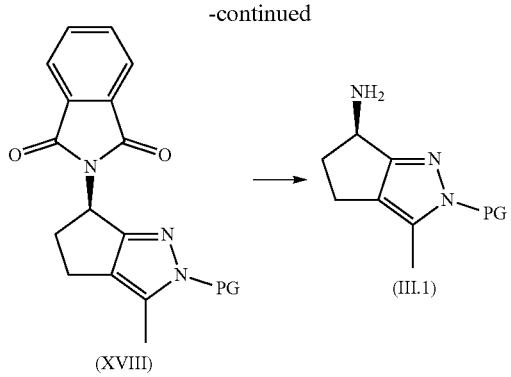

(XVIII) → (III.1)

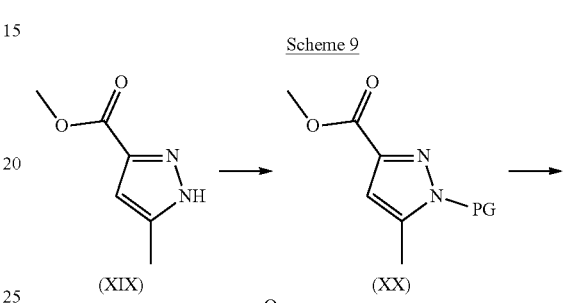

(XVI')     (III'.1)

PG = protective group such as CH$_2$OCH$_2$CH$_2$SiMe$_3$

Scheme 8: Enantiopure amines of formulae (III.1) and (III'.1) can be prepared from ketone (XVI) and (XVI'), respectively, as delineated in Scheme 8. Ketones of formula (XVI) can be enantioselectively reduced under various conditions reported in the literature of organic chemistry (e.g., J. Am. Chem. Soc. 1995, 117, 7562-3; Org. Lett. 2010, 12, 1756-9; Org. Proc. Res. Dev. 2006, 10, 949-958; Tetrahedron: Asymmetry 2003, 14, 2659-2681; Tetrahedron Lett. 2014, 55, 3635-40; and references quoted therein) to give an enantiopure or enantioenriched alcohol of formula (XVII) or (XVII') (not shown), the compound derived from ketone (XVI'). The alcohol can then be reacted with a sufficiently acidic N—H containing molecule such as phthalimide or (tert-Bu-OCO)$_2$NH in a Mitsunobu or Mitsunobu-type reaction (using, e.g., triphenylphosphine or tri-n-butylphosphine combined with dimethyl or diethyl or diisopropyl azodicarboxylate, di-(4-chlorobenzyl) azodicarboxylate, dibenzyl azodicarboxylate, DBAD, azodicarboxylic acid bis-(dimethylamide), azodicarboxylic acid dipiperidide, or azodicarboxylic acid dimorpholide in a suitable solvent (e.g., THF, 1,4-dioxane, EtOAc, benzene, toluene, etc.) leading to introduction of a N residue with inversion of the configuration of the stereocenter (→(XVIII)). Alternatively, a phosphoryl azide (e.g., diphenylphosphoryl azide) can be employed to replace the OH in (XVII) under inversion of the configuration of the adjacent carbon atom with an azide. The amino group can be liberated from the phthalimide group by treatment with, e.g., hydrazine, hydroxylamine, methylamine, n-butylamine, or ethanolamine in a suitable solvent (e.g., EtOH, MeOH, MeCN, THF, dioxane, DMSO, N,N-dimethylacetamide, water, or mixtures of these) with heating if necessary to give a compound of formula (III.1). tert-Bu-O—CO is preferably removed under acidic conditions (using, e.g., TFA or hydrochloric acid) to give amine (III.1). An azide can be reduced to amine (III.1) with, e.g., hydrogen in the presence of a transition metal (e.g., Pd on carbon, Raney-Ni, PtO$_2$, etc.) or a phosphine (e.g., triphenylphosphine).

Alternatively, compound (III.1) can be obtained from ketone (XVI) via a 3-step synthesis sequence employing enantiopure tert-butanesulfinamide in the presence of a titanium alcoholate (e.g., Ti(OEt)$_4$ or Ti (O$^i$Pr)$_4$) in a solvent (e.g., THF, DCM, toluene, or neat) at ambient or elevated temperature to generate the corresponding enantiopure tert-butylsulfinylated imine which can be diastereoselectively reduced to the corresponding tert-butylsulfinylated amine using a hydride (e.g., lithium or sodium borohydride, L-selectride, diisobutylaluminum hydride, etc.) in a suited solvent (e.g., THF, toluene, MeOH, etc., depending on the hydride source used). tert-Butylsulfinyl group can be cleaved off using an acid (e.g., TFA or hydrochloric acid) in a suitable solvent (e.g., toluene, DCM, dioxane, alcohol, water, etc.) at ambient or elevated temperature.

Scheme 9

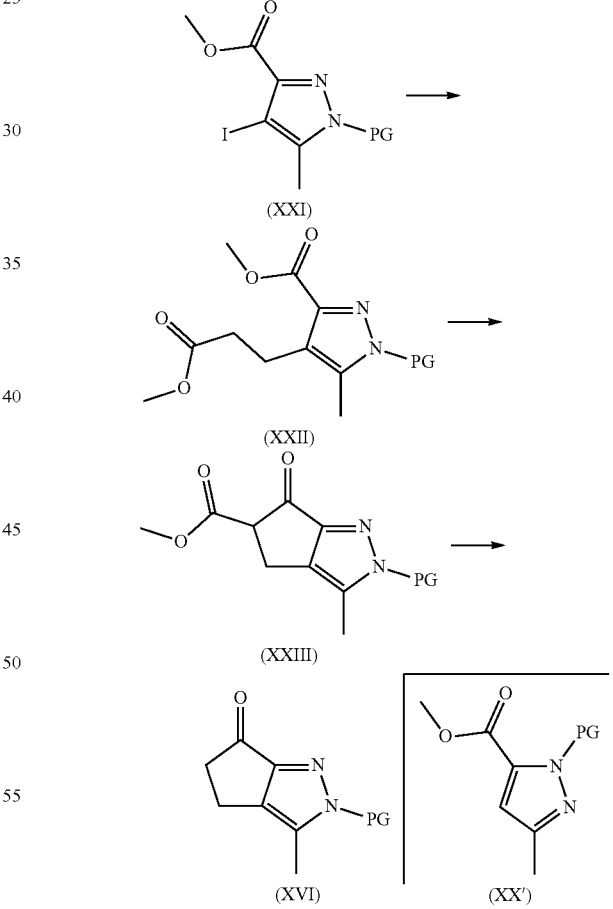

PG = protectice group such as CH$_2$OCH$_2$CH$_2$SiMe$_3$

Scheme 9: Compounds (XVI) can be obtained from reported ester (XIX) (or the corresponding higher alkyl esters, e.g., ethyl, propyl, isopropyl, or tert-butyl ester) in a sequence consisting of 5 or 6 reaction steps. Compound (XIX) can be derivatized on one of its N atoms with a broad range of protecting groups that are reported in the literature of organic chemistry. For instance, compound (XIX) can be transformed into compound (XX) by treatment with a base (e.g., a hydride such as sodium hydride, a hydroxide such as sodium hydroxide, a carbonate such as sodium or potassium carbonate, an alcoholate such as lithium methoxide or potassium tert-butylate, an organic amine such as triethylamine, Hunig's base, DABCO, DBN, or DBU, a phosphazene such as P$_2$Et phosphazene, an amide such as lithium diisopropylamide or lithium hexamethyldisilazide) in a suited solvent (e.g., benzene, toluene, DCM, THF, dioxane, EtOAc, ACN, DMF, N,N-dimethylacetamide, N-methylpyrrolidinone, etc., depending on the nature of the base used) and concurrent or subsequent reaction with an electrophile (a protective group bearing a leaving group such as chloride, bromide, iodide, alkyl- or arylsulfonyloxy, alkyloxy, acyloxy, etc.) of a suited protective group (e.g., 2-trimethylsilylethyloxymethyl chloride for introducing 2-trimethylsilylethyloxymethyl as protective group). Compound (XX) can be chlorinated, brominated, or iodinated employing a suited electrophilic source of the corresponding halogen (e.g., N-chlorosuccinimide for Cl, N-bromosuccinimide or Br$_2$ for Br, N-iodosuccinimide, I$_2$, or ICl for I, optionally in the presence of additives such as silver salts or acids) in a suited solvent (e.g., DCM, dichloroethane, dioxane, MeCN, DMF, etc.). For instance, iodine can be introduced using N-iodosuccinimide and TFA in MeCN to furnish compound (XXI). Compound (XXII) can then be prepared from the corresponding halide (e.g., iodide (XXI)) employing a 1- or 2-step synthesis route encompassing a Heck coupling reaction (broadly covered in the literature of organic chemistry, e.g., in Catalysts 2017, 7, 267 and references quoted therein) with either acrolein dialkyl acetal (e.g., acrolein dimethyl acetal) or an acrylic acid ester (e.g., acrylic methyl ester); using the latter coupling partner requires an additional step to reduce the olefinic bond formed that can be conducted with hydrogen in the presence of a transition metal catalyst (e.g., Pd such as palladium on carbon, Ni such as Raney-Ni, Pt such as platinum oxide, Rh such as rhodium on carbon, etc.) in a suited solvent (e.g., DCM, dioxane, THF, EtOAc, alcohol such as MeOH, water, etc.). Ketoester (XXIII) may be produced upon treatment of compound (XXII) with a base (e.g., a hydride such as sodium hydride, an alcoholate such as lithium methoxide or potassium tert-butylate, an organic amine such as DBU, a phosphazene such as P2Et phosphazene, an amide such as lithium diisopropylamide, lithium, sodium or potassium hexamethyldisilazide, etc.) in a suited solvent (e.g., benzene, toluene, dioxane, THF, alcohol, etc., depending on the base used) at low to increased temperature (−78° C. to 100° C., depending on the base and solvent employed). Hydrolysis of the ester group in compound (XXIII) followed by decarboxylation can be achieved by stirring the compound in a solvent (e.g., dioxane, THF, MeCN, DMF, N,N-dimethylacetamide, DMSO, alcohol, water, etc., or mixtures of these), optionally in the presence of a base (e.g., sodium hydroxide), a halide salt such as lithium iodide or chloride, or an acid (e.g., hydrochloric acid) at 0 to 140° C. to give ketone (XVI). The entire sequence may be analogously applied to the isomerically protected compound (XX') to give the ketone (XVI') and does not necessarily rely on the use of a protective group and thus might be carried out without one (PG=H).

As mentioned above, the compounds of formula (I) may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled person from the literature.

Thus, according to another aspect of the present invention, processes for the synthesis of compounds of formula (I) are provided.

According to another aspect of the present invention, intermediates of the synthesis of compounds of formula (I) are provided.

Pharmacological Activity

The activity of the compounds of the invention may be demonstrated using the following assays:

Biological Methods

The ability of compounds of formula (I) to inhibit plasma kallikrein (PKK), Factor XIIa (FXIIa), Factor XIa (FXIa), Factor Xa (FXa), Factor IIa (alpha-thrombin; FIIa), plasmin, trypsin, tissue kallikrein 1 (TK1), Factor VIIa (FVIIa), or FVIIa complexed with Tissue Factor, phospholipids and CaCl$_2$ (FVIIa/TF/PL/CaCl$_2$) is determined using the following biochemical assays in assay buffer (100 mM Tris, 150 mM NaCL, adjusted to a pH of 7.8 with HCl, and containing 0.1% (w/v) BSA and 0.05% (v/v) Tween20) in the presence of 1% (v/v) DMSO:

Evaluation of the Inhibition of PKK Using an Endpoint Assay

Human PKK (0.01 U/mL; Enzyme Research Laboratories) or rat PKK (0.625 nM; produced in-house) is incubated for 1 h at room temperature with 0.10 µM fluorogenic substrate H-Pro-Phe-Arg-AMC (I1295 from Bachem) and various concentrations of the test compound in assay buffer. Subsequently, PPACK 11 (Calbiochem) is added as a stop solution to achieve a final concentration of 1 µM and fluorescence is measured using an Envision Reader (PerkinElmer) with the wavelength excitation setting of 355 nm and the wavelength emission setting of 460 nm.

IC$_{50}$ values for compounds according to the invention are shown in the following table. The number of the compound corresponds to the number of the Example in the experimental section.

| Example | IC$_{50}$ (nM) |
|---|---|
| 1 | 0.8 |
| 5 | 0.5 |
| 9 | 1.8 |
| 13 | 1.9 |
| 2 | 1.8 |
| 6 | 0.7 |
| 10 | 0.8 |
| 3 | 0.9 |
| 7 | 0.8 |
| 11 | 0.6 |
| 4 | 0.5 |
| 8 | 2.1 |
| 12 | 2.6 |

Evaluation of the Inhibition of PKK in Kaolin Activated Human PPP

Platelet poor plasma (PPP) obtained from human whole-blood, anticoagulated with Na-Citrate, is incubated with various concentrations of the test compound together with either 25, 75, 250, or 750 µg/mL kaolin in assay buffer for 20 min at 37° C. such that for each kaolin dose used a concentration response is obtained for the test compound.

Afterwards 0.25 mM fluorogenic substrate H-Pro-Phe-Arg-AMC (I1295 from Bachem) is added to the mixture and measurements are performed in a kinetic interval every 2nd minute for 12 min using a Spectramax M5 (Molecular Devices) with the following settings of the wavelength excitation of 350 nm and wavelength emission of 450 nm. pIC50 and pIC90 values are obtained from 4 x/y-plots (x=log M, Compound; y=delta rfu/min) fitted with GraphPad prism 7.0 (Equation: log(agonist) vs. response —Find ECanything; the four concentration response curves obtained for the test compound, each obtained using a different kaolin dose, are fitted using a global fitting procedure yielding shared pIC50 or pIC90 values).

$IC_{90}$ values for compounds according to the invention are shown in the following table. The number of the compound corresponds to the number of the Example in the experimental section.

| Example | $IC_{90}$ (nM) |
|---|---|
| 1 | 182 |
| 5 | 149 |
| 9 | 539 |
| 2 | 499 |
| 6 | 293 |
| 10 | 242 |
| 3 | 486 |
| 7 | 195 |
| 11 | 236 |
| 4 | 122 |
| 8 | 305 |
| 13 | 746 |

Evaluation of the Inhibition of PKK ($K_i$)

Human PKK (1.78 nM or 0.025 U/mL; Enzyme Research Laboratories) is incubated at 24° C. with 0.25 mM fluorogenic substrate H-Pro-Phe-Arg-AMC (I1295 from Bachem) and various concentrations of the test compound in assay buffer. Measurements are performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FXIIa ($K_i$)

Human FXIIa (47.5 nM or 1.1 U/mL; Enzyme Research Laboratories) is incubated at 24° C. with 0.5 mM chromogenic Substrate S2302 (Chromogenix) and various concentrations of the test compound in assay buffer. Measurements are performed in a kinetic interval every $2^{nd}$ minute for 16 min using a Spectramax M5 (Molecular Devices) measuring the optical absorbance at 405 nm.

Evaluation of the Inhibition of FXIa ($K_i$)

Human FXIa (0.5 nM or 0.016 U/mL; Enzyme Research Laboratories) is incubated at 24° C. with 0.25 mM fluorogenic substrate Boc-Glu(OBzl)-Ala-Arg-AMC.HCl (11575 from Bachem) and various concentrations of the test compound in assay buffer. Measurements are performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FXa ($K_i$)

Human FXa (0.86 nM or 0.01 U/mL; Enzyme Research Laboratories) is incubated at 24° C. with 0.5 mM chromogenic Substrate S2765 (Chromogenix) and various concentrations of the test compound in assay buffer. Measurements are performed in a kinetic interval every $2^{nd}$ minute for 16 min using a Spectramax M5 (Molecular Devices) measuring the optical absorbance at 405 nm.

Evaluation of the Inhibition of FIIa ($K_i$)

Human FIIa (44.6 nM or 5 U/mL; Enzyme Research Laboratories) is incubated at 24° C. with 0.5 mM chromogenic Substrate S2238 (Chromogenix) and various concentrations of the test compound in assay buffer. Measurements are performed in a kinetic interval every $2^{nd}$ minute for 16 min using a Spectramax M5 (Molecular Devices) measuring the optical absorbance at 405 nm.

Evaluation of the Inhibition of Plasmin ($K_i$)

Human plasmin (64.1 nM or 0.0275 U/mL; Enzyme Research Laboratories) is incubated at 24° C. with 0.3 mM chromogenic Substrate S2251 (Chromogenix) and various concentrations of the test compound in assay buffer. Measurements are performed in a kinetic interval every $2^{nd}$ minute for 16 min using a Spectramax M5 (Molecular Devices) measuring the optical absorbance at 405 nm.

Evaluation of the Inhibition of Trypsin ($K_i$)

Human trypsin (4.54 nM or 250 U/mL; Calbiochem) is incubated at 24° C. with 0.5 mM chromogenic Substrate S2222 (Chromogenix) and various concentrations of the test compound in assay buffer. Measurements are performed in a kinetic interval every $2^{nd}$ minute for 16 min using a Spectramax M5 (Molecular Devices) measuring the optical absorbance at 405 nm.

Evaluation of the Inhibition of TK1 ($K_i$)

Prior to the assay, human TK1 (R&D Systems) is activated by incubation with human trypsin (Calbiochem) in a 1:10,000 ratio for 15 min at 37° C. For assaying TK1 inhibitory activity, activated TK1 (31.25 nM or 1 U/mL) is incubated at 24° C. with 0.1 mM fluorogenic substrate H-Pro-Phe-Arg-AMC (I1295 from Bachem) and various concentrations of the test compound in assay buffer. Measurements are performed in a kinetic interval every $2^{nd}$ minute for 16 min using a Spectramax M5 (Molecular Devices) with the following settings of the wavelength excitation of 350 nm and wavelength emission of 450 nm.

$K_i$ values for compounds according to the invention are shown in the following table. The number of the compound corresponds to the number of the Example in the experimental section.

| Example | $K_i$ (nM) | Example | $K_i$ (nM) |
|---|---|---|---|
| 9 | >10000 | 13 | >10000 |

Evaluation of the Inhibition of FVIIa ($K_i$)

Human FVIIa (0.86 nM or 0.01 U/mL; Enzyme Research Laboratories) is incubated at 24° C. with 1.5 mM chromogenic Pefachrome® FVIIa (Loxo) and various concentrations of the test compound in assay buffer. Measurements are performed in a kinetic interval every $2^{nd}$ minute for 16 min using a Spectramax M5 (Molecular Devices) measuring the optical absorbance at 405 nm.

Evaluation of the Inhibition of FVIIa/TF/PL/CaCl$_2$($K_i$)

Human FVIIa (300 nM or 585 U/mL; Enzyme Research Laboratories) together with 10 mM CaCl$_2$*2H$_2$O and 13.3% (v/v) Dade® Innovin® (Siemens; OQUMI94E0002(5534), which contains recombinant human tissue factor synthetic phospholipids (thromboplastin), is incubated at 24° C. with 1.5 mM chromogenic Pefachrome® FVIIa (Loxo) and various concentrations of the test compound in assay buffer. Measurements are performed in a kinetic interval every $2^{nd}$ minute for 16 min using a Spectramax M5 (Molecular Devices) measuring the optical absorbance at 405 nm.

Calculation of $pIC_{50}$ and $pK_i$ Values

The average $V_{max}$ values for the time interval from 2 to 12 min after initiation of the assay (expressed as either delta OD/min for assays using a chromogenic substrate or delta RFU/min for assays using a fluorogenic substrate, respectively) are plotted versus the Log of the concentration in molar of the evaluated inhibitor compound. The $pIC_{50}$ values are then fitted using a four-parametric fitting procedure using GraphPad Prism (version 6; GraphPad Software, Inc.). Respective $K_i$ values are obtained by correction of the $IC_{50}$ values for the respective $K_M$ value of the used substrate (see Table A for the obtained $K_M$ values of the used substrates) using the following formula:

$$K_i = \frac{IC_{50}}{1+\frac{[\text{Substrate, mM}]}{K_M}}$$

Where the $IC_{50}$ is in molar and the $K_M$ value in mM.

TABLE A $K_M$ values obtained for the substrates used in the enzymatic assays.

| Enzyme | Substrate | $K_M$ (mM) |
|---|---|---|
| PKK | I1295 | 0.16 |
| FXIIa | S2302 | 0.20 |
| FXIa | I1575 | 0.29 |
| FXa | S2765 | 1.31 |
| FIIa | S2238 | 1.25 |
| Plasmin | S2251 | 1.45 |
| Trypsin | S2222 | 2.03 |
| TK1 | I1295 | 0.07 |
| FVIIa | Pefachrome ® FVIIa | 0.42 |
| FVIIa/TF/PL/CaCl$_2$ | Pefachrome ® FVIIa | 3.92 |

Evaluation of Permeability

Caco-2 cells (1-2×10$^5$ cells/1 cm$^2$ area) are seeded on filter inserts (Costar transwell polycarbonate or PET filters, 0.4 µm pore size) and cultured (DMEM) for 10 to 25 days.

Compounds are dissolved in appropriate solvent (like DMSO, 1-20 mM stock solutions). Stock solutions are diluted with HTP-4 buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$×7H$_2$O, 0.41 mM NaH$_2$PO$_4$×H$_2$O, 15 mM HEPES, 20 mM glucose, pH 7.2) containing 0.25% BSA to prepare the transport solutions (0.1-300 µM compound, final DMSO<=0.5%). The transport solution (TL) is applied to the apical or basolateral donor side for measuring A-B or B-A permeability (2 filter replicates), respectively. The receiver side contains HTP-4 buffer supplemented with 0.25% BSA. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Evaluation of Metabolic Stability in Human or Rat Liver Microsomes

The metabolic degradation of the test compound is assayed at 37° C. with pooled human (HLM) or rat liver microsomes (RLM). The final incubation volume of 60 µl per time point contains TRIS buffer pH 7.6 at RT (0.1 M), magnesium chloride (5 mM), microsomal protein (HLM: 1 mg/mL, RLM: 0.5 mg/mL) and the test compound at a final concentration of 1 µM.

Following a short preincubation period at 37° C., the reactions are initiated by addition of beta-nicotinamide adenine dinucleotide phosphate, reduced form (NADPH, 1 mM) and terminated by transferring an aliquot into solvent after different time points. Additionally, the NADPH-independent degradation is monitored in incubations without NADPH, terminated at the last time point. The quenched incubations are pelleted by centrifugation (10000 g, 5 min). An aliquot of the supernatant is assayed by LC-MS/MS for the amount of parent compound. The half-life (t½ INVITRO) is determined by the slope of the semilogarithmic plot of the concentration-time profile.

Evaluation of Metabolic Stability in Human or Rat Hepatocytes

The metabolic degradation of the test compound is assayed in a hepatocyte suspension. After recovery from cryopreservation, human or rat hepatocytes are incubated in Dulbecco's modified eagle medium supplemented with 3.5 µg glucagon/500 ml, 2.5 mg insulin/500 ml and 3.75 mg/500 ml hydrocortisone) containing 5% or 50% human or rat serum or in absence of serum.

Following a 30 min preincubation in a cell culture incubator (37° C., 10% CO$_2$), test compound solution is spiked into the hepatocyte suspension to obtain a final cell density of 1.0*106 cells/ml, a final test compound concentration of 1 µM, and a final DMSO concentration of 0.05%.

The cells are incubated for six hours (incubator, horizontal shaker) and samples are removed from the incubation after 0, 0.5, 1, 2, 4 and 6 hours. Samples are quenched with acetonitrile and pelleted by centrifugation. The supernatant is transferred to a 96-deepwell plate, and prepared for analysis of decline of parent compound by HPLC-MS/MS.

$CL_{int}$ is calculated as follows:

$$CL_{int}=Dose/AUC=(C0/CD)/(AUD+clast/k)\times 1000/60$$

C0: initial concentration in the incubation [µM], CD: cell density of vital cells [10e6 cells/ml], AUD: area under the data [µM×h], clast: concentration of last data point [µM], k: slope of the regression line for parent decline [h$^{-1}$]. The calculated in vitro hepatic intrinsic clearance can be scaled up to the intrinsic in vivo hepatic clearance and used to predict hepatic in vivo blood clearance (CL) by the use of a liver model (well-stirred model).

Evaluation of Plasma Protein Binding

The equilibrium dialysis (ED) technique is used to determine the approximate in vitro fractional binding of test compounds to plasma proteins applying Dianorm Teflon dialysis cells (micro 0.2). Each dialysis cell consists of a donor and an acceptor chamber, separated by an ultrathin semipermeable membrane with a 5 kDa molecular weight cutoff. Stock solutions for each test compound are prepared in DMSO at 1 mM and serially diluted to obtain a final test concentration of 1 µM. The subsequent dialysis solutions are prepared in plasma (supplemented with NaEDTA as anticoagulant), and aliquots of 200 µl test compound dialysis solution in plasma are dispensed into the donor (plasma) chambers. Aliquots of 200 µl dialysis buffer (100 mM potassium phosphate, pH 7.4) are dispensed into the buffer (acceptor) chamber. Incubation is carried out for 2 hours under rotation at 37° C. for establishing equilibrium. At the end of the dialysis period, aliquots obtained from donor and acceptor chambers, respectively, are transferred into reaction tubes, spiked with Internal Standard solution and processed for HPLC-MS/MS analysis. Analyte concentrations are quantified in aliquots of samples by HPLC-MS/MS against external calibration curves.

Percent bound is calculated using the formula:

% bound=(plasma concentration−buffer concentration/plasma concentration)×100

Evaluation of Solubility

The aqueous solubility of the test compound is determined by comparing the amount dissolved in buffer to the amount in an ACN/water (1/1) solution. Starting from a 10 mM DMSO stock solution aliquots are diluted with acetonitrile/water (1/1) or buffer resp. After 24 h of shaking, the solutions are filtrated and analyzed by LC-UV. The amount dissolved in buffer is compared to the amount in the ACN solution.

Solubility will usually be measured from 0.001 to 0.125 mg/mL at a DMSO concentration of 2.5%. If more than 90% of the compound is dissolved in buffer, the value is marked with ">".

Evaluation of Pharmacokinetic Characteristics in Rodents

The test compound is administered either intravenously to fed rats or orally to fasted rats. Blood samples are taken at several time points post application of the test compound, anticoagulated and centrifuged.

The concentration of analytes—the administered compound and/or metabolites—are quantified in the plasma samples. PK parameters are calculated using non compartment methods. AUC and Cmax are normalized to a dose of 1 μmol/kg.

Evaluation of Inhibition of Cytochrome P450 Isoenzyme-Catalysed Reactions

The inhibition of cytochrome P450 isoenzyme-catalysed reactions by the test compound is assayed at 37° C. with human liver microsomes. All assays are carried out on a robotic system in 384-well plates. Test compounds are directly spotted into incubation plates from DMSO stocks by acoustic liquid dispensing (using the Labyte ECHO® system). The final incubation volume contains TRIS buffer (0.1 M), $MgCl_2$ (5 mM), human liver microsomes, specific cytochrome P450 isoenzyme-substrate and the test compound at five different concentrations or no compound (high control) in duplicate (e.g. highest concentration 50 μM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor is determined. Experimental IC50 values are calculated by least square regression according to the following equation:

% control activity=(100% control activity/(1+($I$/$IC_{50}$)$S$)))−$b$ with
I=inhibitor concentration
S=slope factor
B=background activity If the inhibition of the reaction is already >50% at the lowest concentration of the test compound, the $IC_{50}$ is assigned "<lowest concentration tested" (usually <0.2 μM). If the inhibition of the reaction is still <50% at the highest concentration of the test compound, the IC50 is assigned ">highest concentration tested" (usually >50 μM).

Evaluation of Mechanism-Based Inhibition (MBI) of Cytochrome P450 3A4-Catalysed Midazolam Turnover The mechanism-based inhibition towards CYP3A4 is assayed in human liver microsomes (0.02 mg/ml) with Midazolam (15 uM) as a substrate.

The test compounds are preincubated at 37° C. in presence of NADPH with human liver microsomes (0.2 mg/ml) at a concentration of 5 uM and 25 uM for 0 min, 10 min or 30 min. After preincubation, the incubate is diluted 1:10 and the substrate Midazolam is added for the main incubation (15 min). The main incubation is quenched with acetonitrile and the formation of Hydroxy-Midazolam is quantified via LC/MS-MS.

The turnover rates in pmol/min/mg protein are calculated and the activity after 10 and 30 min preincubation time is compared to that of the 0 min preincubation of the respective compound/concentration (% CTRL=% of the 0 min control of the respective compound/concentration). Additionally, the turnover rate is expressed relative to the turnover rate of the substrate reaction without compound added (% TR=% of the turnover rate without compound), in order to recognize competitive inhibition effects.

Methods of Treatment

In another aspect of the present invention, it is found that compounds of formula (I) or pharmaceutically acceptable salts thereof possess suitable properties for use in therapy and/or prevention, i.e. for use as medicaments. In particular, compounds of formula (I) or pharmaceutically acceptable salts thereof, as well as pharmaceutical compositions containing the same, may be useful for the treatment, i.e. therapy and/or prevention (prophylaxis), of diseases or conditions, which can be influenced by the inhibition of plasma kallikrein, e.g. which are mediated by unwanted PKK activity or in which inhibition of PKK is beneficial, in a patient.

Diseases and conditions which can be influenced by the inhibition of PKK, e.g. which are mediated by unwanted PKK activity or in which inhibition of PKK is beneficial, are, for instance, those mentioned in section Background of the Invention, in particular diabetic complications, diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retinal vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), choroidal neovascularization (CNV; e.g. non-exudative choroidal neovascularization), hereditary angioedema (HAE), acute respiratory distress syndrome (ARDS), hemorrhage and edema after stroke, e.g. brain edema after stroke, vascular dementia, Alzheimer's disease, fibrotic disease, colitis, arthritis and renal injury.

Thus, the compounds and pharmaceutical compositions of the present invention are particularly suitable for treating ocular diseases including diabetic retinopathy, proliferative and non-proliferative retinopathy, diabetic macular edema (DME), retinal vein occlusion, age-related macular degeneration (AMD), polypoidal choroidal vasculopathy (PCV) and choroidal neovascularization (CNV; e.g. non-exudative choroidal neovascularization).

In addition, the compounds and pharmaceutical compositions according to the invention are particularly suitable for the treatment of edema, such as hereditary angioedema (HAE) and brain edema after stroke.

In particular, the compounds and pharmaceutical compositions according to the invention are suitable for the treatment of diabetic retinopathy, proliferative and non-proliferative retinopathy, diabetic macular edema (DME), age-related macular degeneration (AMD), polypoidal choroidal vasculopathy (PCV), choroidal neovascularization (CNV), hereditary angioedema (HAE), and brain edema after stroke.

The compounds and pharmaceutical compositions according to the invention are most particularly suitable for treating diabetic macular edema (DME), wet age-related macular degeneration (AMD), non-exudative choroidal neovascularization (CNV), hereditary angioedema (HAE), and brain edema after stroke.

For instance, they are particularly suitable for the prevention of diabetic macular edema (DME), wet age-related macular degeneration (AMD), hereditary angioedema (HAE), and brain edema after stroke as well as for the prevention of the conversion from non-exudative choroidal neovascularization (neCNV) to exudative choroidal neovascularization (eCNV).

The dose range of the compounds of formula (I) applicable per day is usually from 0.01 to 10 mg per kg body weight. The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds and compositions, including any combinations with one or more additional therapeutic agents, according to the invention may be administered by oral, intravitreal, transdermal, inhalative, parenteral or sublingual route. Of the possible methods of administration, oral or intravitreal administration is preferred. In case of intravitreal injection the preferred dose should not exceed 5 mg per eye.

The patient to be treated is preferably a mammal, most preferably a human patient.

Thus, according to another aspect, the present invention provides a compound of formula (I) and its tautomers, including pharmaceutically acceptable salts thereof, for use as a medicament.

In another aspect, the present invention provides a method for the treatment of a disease or condition, which is mediated by unwanted plasma kallikrein activity or in which inhibition of plasma kallikrein is beneficial, in a patient in need thereof.

Likewise, the present invention provides a compound of formula (I) and/or its tautomers or a pharmaceutically acceptable salt thereof for use in a method for the treatment of a disease or condition, which is mediated by unwanted plasma kallikrein activity or in which inhibition of plasma kallikrein is beneficial, in a patient in need thereof.

Likewise, the present invention provides the use of a compound of formula (I) and/or its tautomers or a pharmaceutically acceptable salt thereof, in the manufacture of a medicament for use in a method for the treatment of a disease or condition, which is mediated by unwanted plasma kallikrein activity or in which inhibition of plasma kallikrein is beneficial, in a patient in need thereof.

Likewise, the present invention provides the use of a compound of formula (I) and/or its tautomers or a pharmaceutically acceptable salt thereof, in a method for the treatment of a disease or condition, which is mediated by unwanted plasma kallikrein activity or in which inhibition of plasma kallikrein is beneficial, in a patient in need thereof.

According to one embodiment, the method for the treatment comprises administering to the patient one or more compounds of formula (I) and/or its tautomers or pharmaceutically acceptable salts thereof, preferably administering to the patient a therapeutically effective amount of one or more compounds of formula (I) and/or its tautomers or pharmaceutically acceptable salts thereof.

According to another embodiment, the method for the treatment comprises administering to the patient a pharmaceutical composition according to the present invention.

According to one embodiment, the disease or condition, which is mediated by unwanted plasma kallikrein activity or in which inhibition of plasma kallikrein is beneficial, is selected from ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV).

According to another embodiment, the disease or condition, which is mediated by unwanted plasma kallikrein activity or in which inhibition of plasma kallikrein is beneficial, is selected from edema-associated diseases such as hereditary angioedema (HAE) and brain edema after stroke.

According to another embodiment, the disease or condition, which is mediated by unwanted plasma kallikrein activity or in which inhibition of plasma kallikrein is beneficial, is selected from diabetic complications such as retinal vascular permeability associated with diabetic retinopathy and diabetic macular edema.

According to one embodiment, the patient is a human patient.

Pharmaceutical Compositions

In another aspect of the present invention, it is described that a compound of the invention or a pharmaceutically acceptable salt thereof may be used as active ingredients in pharmaceutical compositions.

Suitable preparations for administering the compounds of the invention, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. For intravitreal injection, solutions are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled person on the basis of his specialist knowledge. The preferred ones are those that are suitable for the particular formulation and method of administration that are desired. The preparations or formulations according to the invention may be prepared using methods known per se that are familiar to the skilled person, such as for example by mixing or combining at least one compound of formula (I) according to the invention, or a pharmaceutically acceptable salt of such a compound, and one or more excipients, carriers and/or diluents.

Thus, according to another aspect of the present invention, pharmaceutical compositions comprising one or more compounds of formula (I) and/or their tautomers, or pharmaceutically acceptable salts thereof, optionally together with one or more inert carriers and/or diluents are provided.

Also, a pharmaceutical composition that comprises one or more of the above-mentioned compounds, or pharmaceutically acceptable salts thereof, optionally together with one or more inert carriers and/or diluents is provided for use in a method for the treatment of diseases or conditions which are mediated by unwanted plasma kallikrein activity or in which inhibition of plasma kallikrein is beneficial, in a patient in need thereof.

In particular, the invention provides a pharmaceutical composition according to this invention for use in a method for the treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) and of edema-associated diseases such as hereditary angioedema (HAE) and brain edema after stroke.

Furthermore, the present invention relates to the use of a pharmaceutical composition according to this invention for the treatment of diseases or conditions which are mediated by unwanted plasma kallikrein activity in a patient, preferably in a human.

Also, the present invention relates to the use of a pharmaceutical composition according to this invention for the treatment of diseases or conditions in which inhibition of plasma kallikrein is beneficial in a patient, preferably in a human.

According to another embodiment, a pharmaceutical composition comprising one or more compounds of formula (I) and/or their tautomers, or pharmaceutically acceptable salts thereof, and one or more additional therapeutic agents, optionally together with one or more inert carriers and/or diluents is provided.

Preferably, this composition comprises one compound of formula (I) and/or its tautomers or a pharmaceutically acceptable salt thereof and one or more additional therapeutic agents.

Combination Therapy

The compounds of the invention may further be combined with one or more, preferably one additional therapeutic agent.

According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia, or therapeutic agents useful for the treatment of ocular diseases.

Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity, agents for the treatment of high blood pressure, heart failure and/or atherosclerosis and agents for the treatment of ocular diseases. Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, 33-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

Therapeutic agents for the treatment of ocular diseases may include for example intravitreally administered corticosteroids, intravitreally administered anti-VEGF therapy, anti-Ang2 inhibitors, dual anti-VEGF/anti-Ang2 inhibitors, anti PDGF, dual anti-VEGF/anti-PDGF, VAP-1 (AOC3) inhibitors, Complement inhibitors (e.g. Complement factors 3, 5, B, and D inhibitors), Bradykinin receptor 1 antagonists, CCR-2 antagonists.

Additional treatments for ocular diseases may include laser coagulation therapy.

Preferably, compounds of the present invention and/or pharmaceutical compositions comprising a compound of the present invention optionally in combination with one or more additional therapeutic agents are administered in conjunction with exercise and/or a diet.

The dosage for the combination partners mentioned above is usually ⅕ of the lowest dose normally recommended up to 1/1 of the normally recommended dose.

The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Thus, according to another aspect, this invention relates to a pharmaceutical composition which comprises one or more compounds according to the invention and one or more additional therapeutic agents described hereinbefore and hereinafter, optionally together with one or more inert carriers and/or diluents.

According to another aspect, the present invention provides a method for the treatment of a disease or condition, which is mediated by unwanted plasma kallikrein activity or in which inhibition of plasma kallikrein is beneficial, in a patient in need thereof, the method comprising administering to the patient one or more compounds of formula (I) and/or its tautomers or pharmaceutically acceptable salts thereof, in combination with one or more additional therapeutic agents described in hereinbefore and hereinafter, preferably administering to the patient a therapeutically effective amount of one or more compounds of formula (I) and/or its tautomers or pharmaceutically acceptable salts thereof, in combination with a therapeutically effective amount of one or more additional therapeutic agents described in hereinbefore and hereinafter.

Likewise, the present invention provides a compound of formula (I) and/or its tautomers or a pharmaceutically acceptable salt thereof in combination with one or more additional therapeutic agents described hereinbefore or hereinafter for use in a method for the treatment of a disease or condition, which is mediated by unwanted plasma kallikrein activity or in which inhibition of plasma kallikrein is beneficial, in a patient in need thereof.

Likewise, the present invention provides the use of a compound of formula (I) and/or its tautomers or a pharmaceutically acceptable salt thereof, in combination with one or more additional therapeutic agents described hereinbefore or hereinafter, in the manufacture of a medicament for use in a method for the treatment of a disease or condition, which is mediated by unwanted plasma kallikrein activity or in which inhibition of plasma kallikrein is beneficial, in a patient in need thereof.

Likewise, the present invention provides the use of a compound of formula (I) and/or its tautomers or a pharmaceutically acceptable salt thereof, in combination with one or more additional therapeutic agents described hereinbefore or hereinafter, in a method for the treatment of a disease or condition, which is mediated by unwanted plasma kallikrein activity or in which inhibition of plasma kallikrein is beneficial, in a patient in need thereof.

According to one embodiment, the method for the treatment comprises administering to the patient one or more compounds of formula (I) and/or its tautomers or pharmaceutically acceptable salts thereof, in combination with one or more additional therapeutic agents described in hereinbefore and hereinafter, preferably administering to the patient a therapeutically effective amount of one or more compounds of formula (I) and/or its tautomers or pharmaceutically acceptable salts thereof, in combination with a therapeutically effective amount of one or more additional therapeutic agents described in hereinbefore and hereinafter.

According to another embodiment, the method for the treatment comprises administering to the patient a pharmaceutical composition comprising one or more compounds according to the invention and one or more additional therapeutic agents described hereinbefore and hereinafter, optionally together with one or more inert carriers and/or diluents.

According to one embodiment, the one or more additional therapeutic agents are selected from antidiabetic agents, agents for the treatment of overweight and/or obesity, agents for the treatment of high blood pressure, heart failure and/or atherosclerosis and agents for the treatment of ocular diseases, in particular from those agents specifically mentioned above.

According to one embodiment, the disease or condition, which is mediated by unwanted plasma kallikrein activity or in which inhibition of plasma kallikrein is beneficial, is selected from ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV);

from edema-associated diseases such as hereditary angioedema (HAE) and brain edema after stroke; or from diabetic complications such as retinal vascular permeability associated with diabetic retinopathy and diabetic macular edema.

According to one embodiment, the patient is a human patient.

Other features and advantages of the present invention will become apparent from the following more detailed Examples which illustrate, by way of example, the principles of the invention.

EXAMPLES AND EXPERIMENTAL DATA

The following examples are for the purpose of illustration of the invention only and are not intended in any way to limit the scope of the present invention.

Abbreviations

Ac acetyl
ACN acetonitrile
AMC 7-amino-4-methylcoumarin
Boc tert-butyloxycarbonyl
BSA bovine serum albumin
Bzl benzyl
d day(s)
DABCO 1,4-diazabicyclo[2.2.2]octane
DAD diode array detector
DBAD di-tert-butyl azodicarboxylate
DBU 1,8-diazabicyclo[5.4.0]undec-7-ene
DBN 1,5-diazabicyclo[4.3.0]non-5-ene
DCM dichloromethane
DIPEA N,N-diisopropylethylamine
DMEM Dulbecco's modified eagle medium
DMF N,N-dimethylformamide
DMSO dimethyl sulfoxide
EDTA ethylenediaminetetraacetate
ESI electrospray ionization (in MS)
EtOAc ethyl acetate
EtOH ethanol
h hour(s)
HATU O-(7-azabenzotriazol-1-yl)-N,N,N',N'-tetramethyluronium-hexafluorophosphate
HPLC high performance liquid chromatography
HPLC-MS coupled high performance liquid chromatography-mass spectrometry
LC liquid chromatography
LC-MS coupled liquid chromatography-mass spectrometry
LG leaving group
M molar (mol/L)
MeOH methanol
min minute(s)
MS mass spectrometry
NADPH nicotinamide adenine dinucleotide phosphate
NMP N-methyl-2-pyrrolidone NMR nuclear magnetic resonance
PET polyethylene terephthalate
PyBop (benzotriazol-1-yloxy)tripyrrolidinophosphonium hexafluorophosphate
$R_f$ retardation factor
RFU relative fluorescence units
RP reverse phase
rt room temperature
$t_R$ retention time (in HPLC/LC)
TBTU O-(benzotriazol-1-yl)-N,N,N',N'-tetramethyluronium tetrafluoroborate
TFA trifluoroacetic acid
THF tetrahydrofuran
UV ultraviolet The terms "ambient temperature" and "room temperature" are used interchangeably and designate a temperature of about 20° C., e.g. 15 to 25° C.

As a rule, $^1$H-NMR and/or mass spectra have been obtained for the compounds prepared.

Unless otherwise specified, compounds containing chiral centers have the stereochemistry depicted. The assignment of stereochemistry has been made either by use of a chiral starting material of known stereochemistry, by stereoselective synthesis of known stereochemistry or by biological activity.

Analytical Methods

| Method: | 1 | | | |
|---|---|---|---|---|
| Device: | Agilent 1200 with DA- and MS-Detector | | | |
| Column: | XBridge C18, 3 × 30 mm, 2.5 µm | | | |
| Column Supplier: | Waters | | | |

| Gradient/ Solvent Time [min] | % Solvent [H₂O, 0.1% NH₃] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 2 | | | |
|---|---|---|---|---|
| Device: | Agilent 1200 with DA- and MS-Detector | | | |
| Column: | Sunfire C18, 3 × 30 mm, 2.5 µm | | | |
| Column Supplier: | Waters | | | |

| Gradient/ Solvent Time [min] | % Solvent [H₂O, 0.1% TFA] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 3 | | | |
|---|---|---|---|---|
| Device: | Waters Acquity, QDa Detector | | | |
| Column: | XBridge C18, 3 × 30 mm, 2.5 µm | | | |
| Column Supplier: | Waters | | | |

| Gradient/ Solvent Time [min] | % Solvent [H₂O, 0.1% NH₃] | % Solvent [ACN] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

Synthesis of Intermediates

The starting materials and intermediates that are used in the processes leading to the compounds according to the invention are either commercially available or they may be prepared by methods (or by analogous or similar methods to those) described in the following or already known to those skilled in the art from the literature, e.g. from WO 2017/072020, WO 2017/072021 and WO 2018/192866 which are hereby incorporated by reference in their entirety.

Intermediate 1

(6R)-3-Methyl-2H,4H,5H,6H-cyclopenta[c]pyrazol-6-amine; semi-(2S,3S)-2,3-bis(4-methylbenzoyloxy)butanedioic acid salt

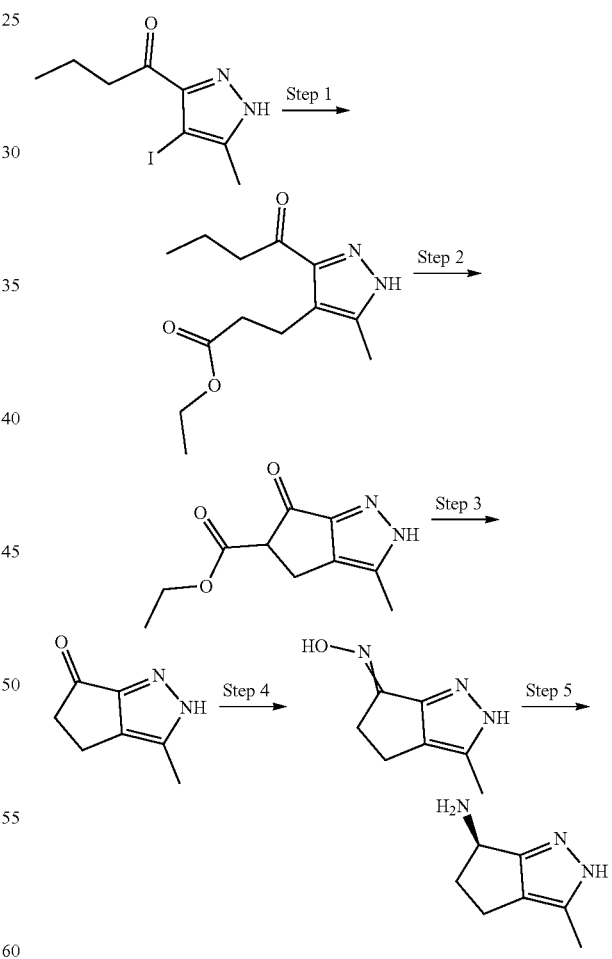

Step 1: Ethyl 4-(3-ethoxy-3-oxopropyl)-5-methyl-1H-pyrazole-3-carboxylate

Under argon atmosphere a mixture of ethyl 4-iodo-5-methyl-1H-pyrazole-3-carboxylate (220 g), 3,3-diethoxyprop-1-ene (112 g), palladium-II-acetate (Pd(OAc)$_2$, 35.3 g), tetrabutylammonium chloride (240 g) and DIPEA (203 g) in DMF (900 mL) is stirred at 110° C. for 2 h and at 120° C. for 1 h. After cooling to ca. 67° C., EtOAc (1.5 L) is added. The mixture is cooled to rt, filtered over celite and the filter cake is washed with EtOAc (2×). The combined filtrates are washed with half-saturated aqueous NaCl (3×) and water (4×). After drying (MgSO$_4$), the mixture is concentrated in vacuo to give the crude product, which is used as is in the next step. Mass spectrum (ESI$^+$): m/z=255 [M+H]$^+$.

Step 2: Ethyl 3-methyl-6-oxo-2H,4H,5H,6H-cyclopenta[c]pyrazole-5-carboxylate

Under argon atmosphere a solution of ethyl 4-(3-ethoxy-3-oxopropyl)-5-methyl-1H-pyrazole-3-carboxylate (191 g) in THF (500 mL) is added between 41 and 64° C. to a solution of NaN(Si(CH$_3$)$_3$)$_2$ (2 M in THF, 1.3 L). The mixture is stirred for 15 min at 60° C. and for 1 h at rt. Then the mixture is poured into a mixture of aqueous HCl (6 N, 851 mL), ice (1 kg) and 2-methyl-tetrahydrofuran (2.5 L). After stirring for 10 min the phases are separated. The organic phase is concentrated in vacuo to give the crude product, which is used as is in the next step. Mass spectrum (ESI$^+$): m/z=209 [M+H]$^+$.

Step 3: 3-Methyl-2H,4H,5H,6H-cyclopenta[c]pyrazol-6-one

A mixture of ethyl 3-methyl-6-oxo-2H,4H,5H,6H-cyclopenta[c]pyrazole-5-carboxylate (363 g) in 1,4-dioxane (1.5 L) and water (110 mL) is heated to 90° C. for 22 h. The mixture is concentrated in vacuo to give the crude product, which is used as is in the next step. Mass spectrum (ESI$^+$): m/z=137 [M+H]$^+$.

Step 4: N-[3-Methyl-2H,4H,5H,6H-cyclopenta[c]pyrazol-6-ylidene]hydroxylamine; hydrochloride A solution of 3-methyl-2H,4H,5H,6H-cyclopenta[c]pyrazol-6-one (294 g) in EtOH (800 mL) is heated to 65° C. and treated with hydroxylamine hydrochloride (52.5 g). The mixture is stirred for 2 h at 60° C. and for 12 h at rt. The precipitate is collected and washed with EtOH and tert.-butyl-methyl-ether. The crude product is dried in vacuo and used as is in the next step. Mass spectrum (ESI$^+$): m/z=152 [M+H]$^+$.

Step 5: (6R)-3-Methyl-2H,4H,5H,6H-cyclopenta[c]pyrazol-6-amine; semi-(2S,3S)-2,3-bis(4-methylbenzoyloxy)-butanedioic acid salt N-[3-Methyl-2H,4H,5H,6H-cyclopenta[c]pyrazol-6-ylidene]hydroxylamine; hydrochloride (85 g) is suspended in MeOH (2.2 L), treated with (1R)-1-phenylethan-1-amine (165 g) and stirred at 40° C. for 30 minutes. 20% Pd(OH)$_2$ on carbon (18 g) is added and the mixture is stirred under hydrogen atmosphere (21 bar) at 65° C. for 8 h and at 100° C. for 12 h. The mixture is cooled to rt, filtered over celite and concentrated in vacuo. The residue is dissolved in isopropanol (1.4 L) and water (70 mL), heated to 60° C. and treated with K$_2$CO$_3$ (94 g). The mixture is stirred for 10 minutes at 60° C., for 50 minutes at 55° C. and filtered. The filter cake is washed with isopropanol. The combined filtrates are concentrated in vacuo. The residue is dissolved in isopropanol (100 mL), heated to 60° C. and treated with a solution of (2S,3S)-2,3-bis(4-methylbenzoyloxy)butanedioic acid (79 g) in isopropanol (700 mL) and water (40 mL). The mixture is heated to 35° C. and filtered. The filtrate is stirred for 30 minutes, heated to 60° C. for 1 h and then for 12 h at rt. The precipitate is collected by filtration and washed with isopropanol and tert.-butyl-methyl-ether. The crude product is dried in vacuo and used as is in the next step. Mass spectrum (ESI$^+$): m/z=138 [M+H]$^+$.

Intermediate 2

6-{5-Azaspiro[2.3]hexan-5-yl}-2-chloropyridine-3-carbaldehyde

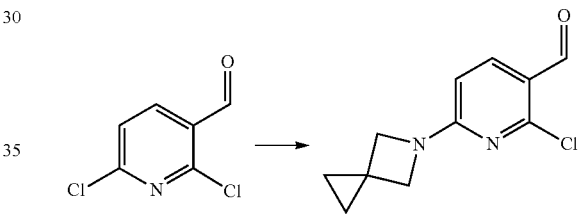

Under argon atmosphere a mixture of 2,6-dichloropyridine-3-carbaldehyde (10 g), 5-azaspiro[2.3]hexane trifluoroacetate (16 g) and DIPEA (40 mL) in DMF (40 mL) is heated to 40° C. for 12 h. The mixture is cooled, concentrated, partitioned between water and DCM and the phases are separated. The organic phase is washed with brine, dried (MgSO$_4$), concentrated and the residue is chromatographed on silica gel (petroleum ether/EtOAc 90:10→70:30) to give the title compound. LC (Method 2): t$_R$=1.03 min; Mass spectrum (ESI+): m/z=223 [M+H]$^+$.

Intermediates 2-1 to 2-4 are prepared in analogy to Intermediate 2:

| Intermediate | Structure | t$_R$ | Mass spectrum (ESI+): m/z [M + H]$^+$ | LC Method |
|---|---|---|---|---|
| 2-1 | ![structure] | 1.04 | 267 | Method 2 |

| Intermediate | Structure | $t_R$ | Mass spectrum (ESI+): m/z [M + H]+ | LC Method |
|---|---|---|---|---|
| 2-2 | ![structure] | 0.99 | 223 | Method 2 |
| 2-3 | ![structure] | 1.02 | 259 | Method 2 |
| 2-4 | ![structure] | 1.03 | 303 | Method 2 |

| Intermediate | Comment on reaction conditions |
|---|---|
| 2-1 | The reaction is conducted for 12 h at rt. |
| 2-2 | The reaction is conducted for 6 h at 90° C. |
| 2-4 | The reaction is conducted for 12 h at 50° C. |

| Intermediate | Name | Name of Starting Material 1 | Name of Starting Material 2 |
|---|---|---|---|
| 2-1 | 6-{3-Azabicyclo[3.1.0]hexan-3-yl}-2-bromopyridine-3-carbaldehyde | 2,6-Dibromopyridine-3-carbaldehyde | 3-Azabicyclo[3.1.0]hexane hydrochloride |
| 2-2 | 6-{3-Azabicyclo[3.1.0]hexan-3-yl}-2-chloropyridine-3-carbaldehyde | 2,6-Dichloropyridine-3-carbaldehyde | 3-Azabicyclo[3.1.0]hexane hydrochloride |
| 2-3 | 2-Chloro-6-{6,6-difluoro-3-azabicyclo-[3.1.0]hexan-3-yl}pyridine-3-carbaldehyde | 2,6-Dichloropyridine-3-carbaldehyde | 6,6-Difluoro-3-azabicyclo-[3.1.0]hexane hydrochloride |
| 2-4 | 2-Bromo-6-{6,6-difluoro-3-azabicyclo-[3.1.0]hexan-3-yl}pyridine-3-carbaldehyde | 2,6-Dibromopyridine-3-carbaldehyde | 6,6-Difluoro-3-azabicyclo-[3.1.0]hexane hydrochloride |

Intermediate 3

(6-{5-Azaspiro[2.3]hexan-5-yl}-2-chloropyridin-3-yl)methanol

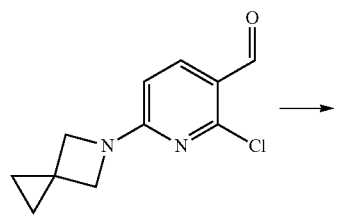

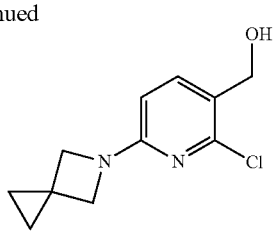

NaBH$_4$ (2.1 g) is added portionwise to a ice-cooled mixture of 6-{5-azaspiro[2.3]hexan-5-yl}-2-chloropyridine-3-carbaldehyde (12 g) in THF (300 mL) and water (3 mL). The mixture is stirred for 20 minutes at 0° C. and for 30 minutes at rt. Then the mixture is poured into a mixture of 500 g ice and saturated aqueous NH$_4$Cl (500 mL). The aqueous phase is extracted twice with DCM. The combined organic phases are dried (MgSO$_4$) and concentrated in vacuo to give the title compound. LC (Method 2): t$_R$=0.84 min; Mass spectrum (ESI+): m/z=225 [M+H]$^+$.

Intermediates 3-1 to 3-4 are prepared in analogy to Intermediate 3:

| Intermediate | Structure | t$_R$ | m/z [M + H]$^+$ | LC Method |
|---|---|---|---|---|
| 3-1 | 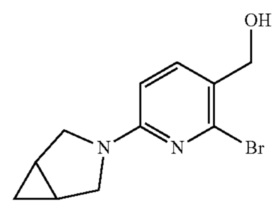 [SMILES: OCc1ccc(N2CC3CC3C2)nc1Br] | 0.94 | 269 | Method 2 |
| 3-2 | 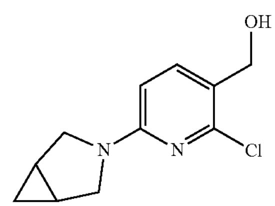 [SMILES: OCc1ccc(N2CC3CC3C2)nc1Cl] | 0.89 | 225 | Method 1 |
| 3-3 | 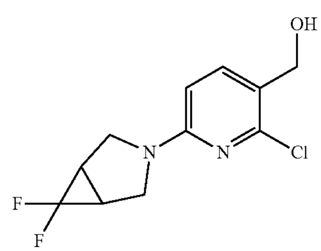 [SMILES: OCc1ccc(N2CC3C(C2)C3(F)F)nc1Cl] | 0.90 | 261 | Method 2 |
| 3-4 | 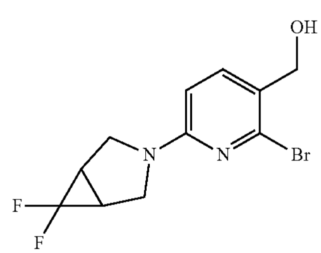 [SMILES: OCc1ccc(N2CC3C(C2)C3(F)F)nc1Br] | 0.94 | 305 | Method 2 |

| Intermediate | Comment on reaction conditions |
|---|---|
| 3-1 | The reaction is conducted in EtOH for 1.5 h. |
| 3-2 | The reaction is conducted in THF/MeOH 2:1 for 30 minutes at 0° C. and for 1 h at rt. |
| 3-3 | The reaction is conducted in THF/MeOH 1:1 for 1 h at rt. |
| 3-4 | The reaction is conducted in EtOH. |

| Intermediate | Name | Name of Starting Material |
|---|---|---|
| 3-1 | (6-{3-Azabicyclo[3.1.0]hexan-3-yl}-2-bromopyridin-3-yl)methanol | 6-{3-Azabicyclo[3.1.0]hexan-3-yl}-2-bromopyridine-3-carbaldehyde |
| 3-2 | (6-{3-Azabicyclo[3.1.0]hexan-3-yl}-2-chloropyridin-3-yl)methanol | 6-{3-Azabicyclo[3.1.0]hexan-3-yl}-2-chloropyridine-3-carbaldehyde |
| 3-3 | (2-Chloro-6-{6,6-difluoro-3-azabicyclo-[3.1.0]hexan-3-yl}pyridin-3-yl)methanol | 2-Chloro-6-{6,6-difluoro-3-azabicyclo-[3.1.0]hexan-3-yl}pyridine-3-carbaldehyde |
| 3-4 | (2-Bromo-6-{6,6-difluoro-3-azabicyclo-[3.1.0]hexan-3-yl}pyridin-3-yl)methanol | 2-Bromo-6-{6,6-difluoro-3-azabicyclo-[3.1.0]hexan-3-yl}pyridine-3-carbaldehyde |

Intermediate 4

Ethyl 1-[(6-{5-azaspiro[2.3]hexan-5-yl}-2-chloropyridin-3-yl)methyl]-1H-pyrazole-4-carboxylate

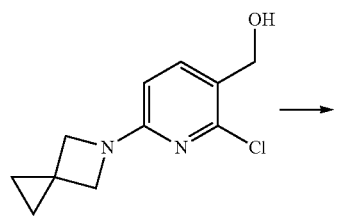

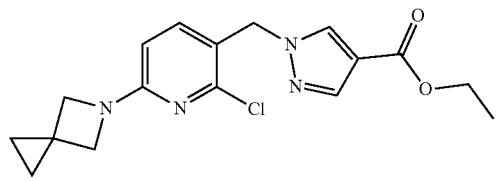 [SMILES: CCOC(=O)c1cn(Cc2ccc(N3CC4(CC4)C3)nc2Cl)nn1]

A mixture of (6-{5-azaspiro[2.3]hexan-5-yl}-2-chloropyridin-3-yl)methanol (5.6 g), ethyl 1H-pyrazole-4-carboxylate (3.6 g) and p-toluenesulfonic acid (2.6 g) in ACN (80 mL) is heated for 2 h to 60° C. After cooling to rt, the mixture is partitioned between saturated aqueous NaHCO$_3$ and EtOAc. The aqueous phase is extracted with EtOAc and the combined organic phases are dried (MgSO$_4$) and concentrated. The residue is chromatographed on silica gel (petroleum ether/EtOAc 100:0→50:50) to give the title compound.

1e;2qLC (Method 2): t$_R$=1.05 min; Mass spectrum (ESI+): m/z=347 [M+H]$^+$.

Intermediates 4-1 to 4-9 are prepared in analogy to Intermediate 4:

| | | Mass spectrum (ESI+): | | |
|---|---|---|---|---|
| Intermediate | Structure | t$_R$ | m/z [M + H]$^+$ | LC Method |
| 4-1 | | 1.08 | 392 | Method 2 |
| 4-2 | | 1.03 | 348 | Method 2 |

-continued

| Intermediate | Structure | $t_R$ | Mass spectrum (ESI+): m/z [M + H]⁺ | LC Method |
|---|---|---|---|---|
| 4-3 | 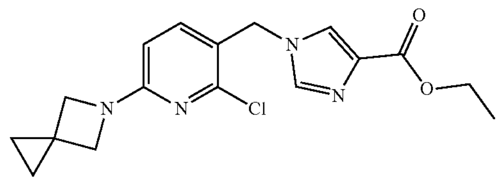 [SMILES: CCOC(=O)c1cn(Cc2ccc(N3CC4(CC4)C3)nc2Cl)cn1] | 0.97 | 347 | Method 1 |
| 4-4 | 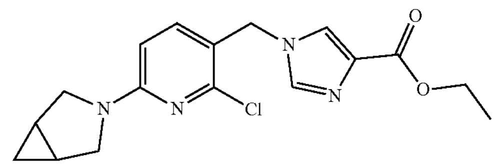 [SMILES: CCOC(=O)c1cn(Cc2ccc(N3CC4CC4C3)nc2Cl)cn1] | 0.91 | 347 | Method 2 |
| 4-5 | 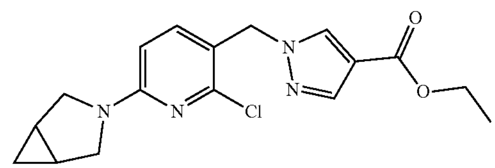 [SMILES: CCOC(=O)c1cnn(Cc2ccc(N3CC4CC4C3)nc2Cl)c1] | 1.08 | 347 | Method 2 |
| 4-6 | 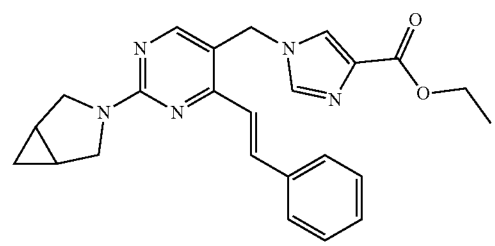 [SMILES: CCOC(=O)c1cn(Cc2cnc(N3CC4CC4C3)nc2/C=C/c2ccccc2)cn1] | 0.93 | 416 | Method 2 |
| 4-7 | 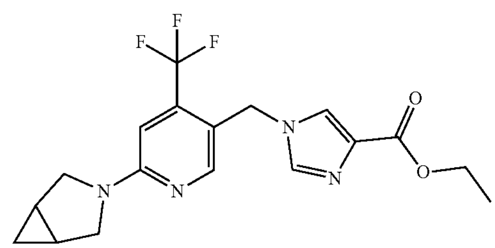 [SMILES: CCOC(=O)c1cn(Cc2cnc(N3CC4CC4C3)cc2C(F)(F)F)cn1] | 1.00 | 381 | Method 1 |
| 4-8 | 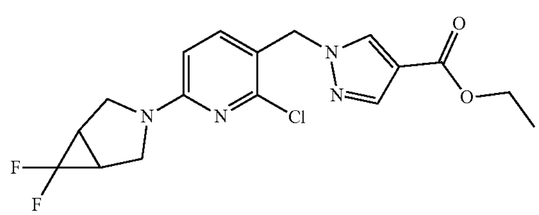 [SMILES: CCOC(=O)c1cnn(Cc2ccc(N3CC4C(C3)C4(F)F)nc2Cl)c1] | 1.10 | 383 | Method 2 |
| 4-9 | 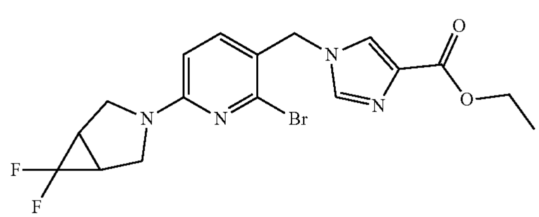 [SMILES: CCOC(=O)c1cn(Cc2ccc(N3CC4C(C3)C4(F)F)nc2Br)cn1] | 0.98 | 427 | Method 1 |

| Intermediate | Comment on reaction conditions |
|---|---|
| 4-1 | The reaction is conducted for 15 minutes at 70° C. |
| 4-2 | The reaction is conducted for 15 minutes at 70° C. |
| 4-3 | The reaction is conducted for 15 h at 80° C. |
| 4-4 | The reaction is conducted for 12 h at 80° C. |
| 4-5 | The reaction is conducted for 1 h at 70° C. |
| 4-6 | Camphersulfonic acid is used instead of p-toluenesulfonic acid. The reaction is conducted for 4 h at 80° C. |
| 4-7 | The reaction is conducted for 22 h at 70° C. |
| 4-8 | The reaction is conducted for 2 h at 80° C. |
| 4-9 | The reaction is conducted for 7 h at 80° C. and for 2 h at 90° C. |

| Intermediate | Name | Name of Starting Material 1 | Name of Starting Material 2 |
|---|---|---|---|
| 4-1 | Ethyl 1-[(6-{3-azabicyclo[3.1.0]-hexan-3-yl}-2-bromopyridin-3-yl)methyl]-1H-1,2,3-triazole-4-carboxylate | (6-{3-Azabicyclo[3.1.0]-hexan-3-yl}-2-bromo-pyridin-3-yl)methanol | Ethyl 1H-1,2,3-triazole-4-carboxylate |
| 4-2 | Ethyl 1-[(6-{5-azaspiro[2.3]-hexan-5-yl}-2-chloropyridin-3-yl)methyl]-1H-1,2,3-triazole-4-carboxylate | (6-{5-Azaspiro[2.3]hexan-5-yl}-2-chloropyridin-3-yl)methanol | Ethyl 1H-1,2,3-triazole-4-carboxylate |
| 4-3 | Ethyl 1-[(6-{5-azaspiro[2.3]-hexan-5-yl}-2-chloropyridin-3-yl)methyl]-1H-imidazole-4-carboxylate | (6-{5-Azaspiro[2.3]hexan-5-yl}-2-chloropyridin-3-yl)methanol | Ethyl 1H-imidazole-4-carboxylate |
| 4-4 | Ethyl 1-[(6-{3-azabicyclo[3.1.0]-hexan-3-yl}-2-chloropyridin-3-yl)methyl]-1H-imidazole-4-carboxylate | (6-{3-Azabicyclo[3.1.0]-hexan-3-yl}-2-chloro-pyridin-3-yl)methanol | Ethyl 1H-imidazole-4-carboxylate |
| 4-5 | Ethyl 1-[(6-{3-azabicyclo[3.1.0]-hexan-3-yl}-2-chloropyridin-3-yl)methyl]-1H-pyrazole-4-carboxylate | (6-{3-Azabicyclo[3.1.0]-hexan-3-yl}-2-chloro-pyridin-3-yl)methanol | Ethyl 1H-pyrazole-4-carboxylate |
| 4-6 | Ethyl 1-[(2-{3-azabicyclo[3.1.0]-hexan-3-yl}-4-[(1E)-2-phenyl-ethenyl]-pyrimidin-5-yl)methyl]-1H-imidazole-4-carboxylate | (2-{3-Azabicyclo[3.1.0]-hexan-3-yl}-4-[(1E)-2-phenylethenyl]pyrimidin-5-yl)methanol | Ethyl 1H-imidazole-4-carboxylate |
| 4-7 | Ethyl 1-[(6-{3-azabicyclo[3.1.0]-hexan-3-yl}-4-(trifluoromethyl)-pyridin-3-yl)methyl]-1H-imidazole-4-carboxylate | (6-{3-Azabicyclo[3.1.0]-hexan-3-yl}-4-(trifluoro-methyl)pyridin-3-yl)methanol | Ethyl 1H-imidazole-4-carboxylate |
| 4-8 | Ethyl 1-[(2-chloro-6-{6,6-difluoro-3-azabicyclo[3.1.0]hexan-3-yl}pyridin-3-yl)methyl]-1H-pyrazole-4-carboxylate | (2-Chloro-6-{6,6-difluoro-3-azabicyclo[3.1.0]hexan-3-yl}pyridin-3-yl)methanol | Ethyl 1H-pyrazole-4-carboxylate |
| 4-9 | Ethyl 1-[(2-bromo-6-{6,6-difluoro-3-azabicyclo[3.1.0]hexan-3-yl}-pyridin-3-yl)methyl]-1H-imidazole-4-carboxylate | (2-Bromo-6-{6,6-difluoro-3-azabicyclo[3.1.0]hexan-3-yl}pyridin-3-yl)methanol | Ethyl 1H-imidazole-4-carboxylate |

Intermediate 5

Ethyl 1-[(6-{5-azaspiro[2.3]hexan-5-yl}-2-ethenylpyridin-3-yl)methyl]-1H-pyrazole-4-carboxylate

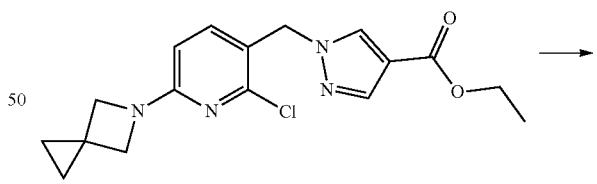

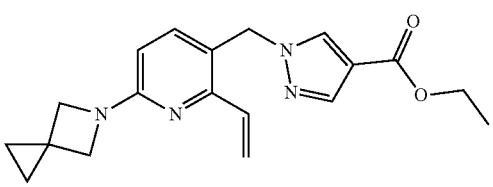 [SMILES: C=Cc1nc(N2CC3(CC3)C2)ccc1Cn1cc(C(=O)OCC)nn1]

In a microwave vial a mixture of ethyl 1-[(6-{5-azaspiro[2.3]hexan-5-yl}-2-chloropyridin-3-yl)methyl]-1H-pyrazole-4-carboxylate (1.2 g), potassium vinyltrifluoroborate (535 mg), K₂CO₃ (920 mg) and THF (25 mL) is purged for 10 minutes with argon. 1,1'-Bis(diphenylphosphino)ferrocenepalladium(II) dichloride (Pd(dppf)Cl₂, 120 mg) is added, the vial is sealed and the mixture is heated to 80° C. for 12 h. After cooling to rt the mixture is diluted with EtOAc. The mixture is washed successively with water and brine. After drying (MgSO₄), the mixture is concentrated in vacuo and the residue is chromatographed on silica gel (petroleum ether/EtOAc 60:40→40:60) to give the title compound.

LC (Method 2): $t_R$=0.78 min; Mass spectrum (ESI+): m/z=339 [M+H]⁺.

Intermediate 5-1 is prepared in analogy to Intermediate 5:

| Intermediate | Structure | $t_R$ | Mass spectrum (ESI+): m/z [M + H]⁺ | LC Method |
|---|---|---|---|---|
| 5-1 | ![structure] | 0.74 | 340 | Method 2 |

| Intermediate | Name | Name of Starting Material |
|---|---|---|
| 5-1 | Ethyl 1-[(6-{5-azaspiro[2.3]hexan-5-yl}-2-ethenylpyridin-3-yl)methyl]-1H-1,2,3-triazole-4-carboxylate | Ethyl 1-[(6-{5-azaspiro[2.3]hexan-5-yl}-2-chloropyridin-3-yl)methyl]-1H-1,2,3-triazole-4-carboxylate |

Intermediate 6

Ethyl 1-[(6-{5-azaspiro[2.3]hexan-5-yl}-2-formylpyridine-3-yl)methyl]-1H-pyrazole-4-carboxylate

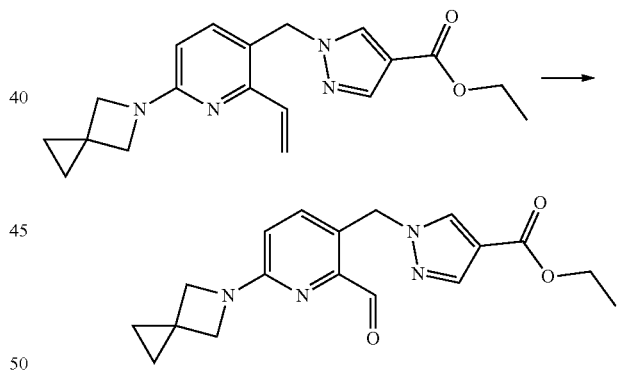

OsO₄ (4% in water, 285 μL) is added to a mixture of ethyl 1-[(6-{5-azaspiro[2.3]hexan-5-yl}-2-ethenylpyridin-3-yl)methyl]-1H-pyrazole-4-carboxylate (760 mg) in 1,4-dioxane (20 mL) and water (2 mL). The mixture is stirred for 30 minutes, treated with NaIO₄ (1.5 g) and stirred for 2 h at rt. The mixture is diluted with EtOAc and washed successively with water, 10% Na₂S₂O₃ in water and brine. After drying (MgSO₄) the mixture is concentrated in vacuo and the residue is chromatographed on silica gel (petroleum ether/EtOAc 80:20→50:50) to give the title compound.

LC (Method 2): $t_R$=0.93 min; Mass spectrum (ESI+): m/z=341 [M+H]⁺.

Intermediates 6-1 to 6-8 are prepared in analogy to Intermediate 6:

| Intermediate | Structure | $t_R$ | Mass spectrum (ESI+): m/z [M + H]$^+$ | LC Method |
|---|---|---|---|---|
| 6-1 | 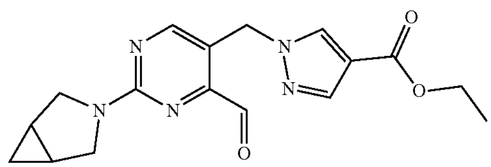 [SMILES: CCOC(=O)c1cnn(Cc2cnc(N3CC4CC4C3)nc2C=O)c1] | | 342 | |
| 6-2 | 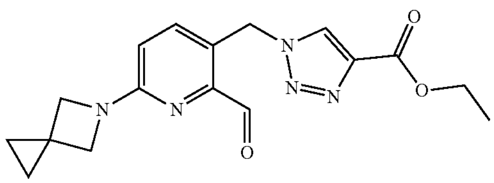 [SMILES: CCOC(=O)c1cn(Cc2ccc(N3CC4(CC4)C3)nc2C=O)nn1] | 0.90 | 342 | Method 2 |
| 6-3 | 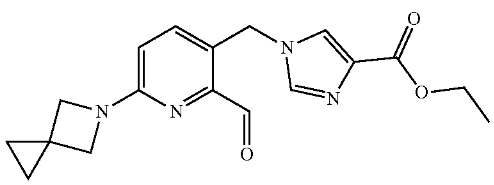 [SMILES: CCOC(=O)c1cn(Cc2ccc(N3CC4(CC4)C3)nc2C=O)cn1] | 0.95 | 341 | Method 1 |
| 6-4 | 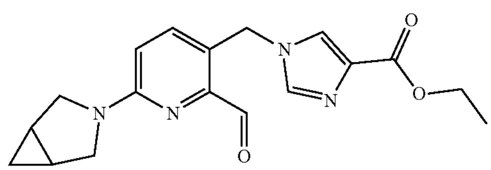 [SMILES: CCOC(=O)c1cn(Cc2ccc(N3CC4CC4C3)nc2C=O)cn1] | 0.98 | 341 | Method 1 |
| 6-5 | 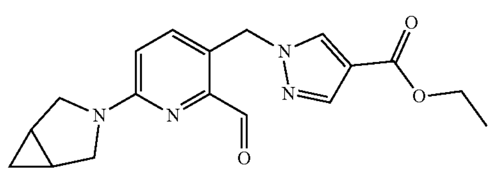 [SMILES: CCOC(=O)c1cnn(Cc2ccc(N3CC4CC4C3)nc2C=O)c1] | 1.08 | 341 | Method 1 |
| 6-6 | 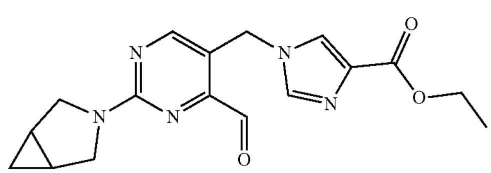 [SMILES: CCOC(=O)c1cn(Cc2cnc(N3CC4CC4C3)nc2C=O)cn1] | 0.87 | 342 | Method 1 |
| 6-7 | 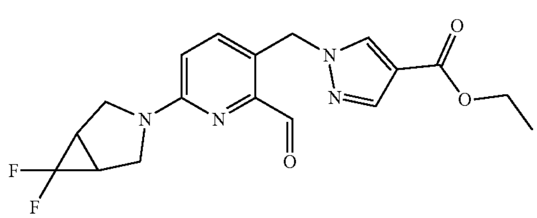 | 1.06 | 377 | Method 2 |
| 6-8 | 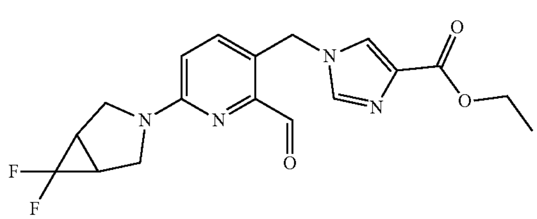 | 0.95 | 377 | Method 1 |

| Intermediate | Comment on reaction conditions |
|---|---|
| 6-6 | The mixture is stirred for 12 h after addition of NaIO₄. |

| Intermediate | Name | Name of Starting Material |
|---|---|---|
| 6-1 | Ethyl 1-[(2-{3-azabicyclo[3.1.0]hexan-3-yl}-4-formylpyrimidin-5-yl)methyl]-1H-pyrazole-4-carboxylate | Ethyl 1-[(2-{3-azabicyclo[3.1.0]hexan-3-yl}-4-[(1E)-2-phenylethenyl]pyrimidin-5-yl)methyl]-1H-pyrazole-4-carboxylate |
| 6-2 | Ethyl 1-[(6-{5-azaspiro[2.3]hexan-5-yl}-2-formylpyridin-3-yl)methyl]-1H-1,2,3-triazole-4-carboxylate | Ethyl 1-[(6-{5-azaspiro[2.3]hexan-5-yl}-2-ethenylpyridin-3-yl)methyl]-1H-1,2,3-triazole-4-carboxylate |
| 6-3 | Ethyl 1-[(6-{5-azaspiro[2.3]hexan-5-yl}-2-formylpyridin-3-yl)methyl]-1H-imidazole-4-carboxylate | Ethyl 1-[(6-{5-azaspiro[2.3]hexan-5-yl}-2-ethenylpyridin-3-yl)methyl]-1H-imidazole-4-carboxylate |
| 6-4 | Ethyl 1-[(6-{3-azabicyclo[3.1.0]hexan-3-yl}-2-formylpyridin-3-yl)methyl]-1H-imidazole-4-carboxylate | Ethyl 1-[(6-{3-azabicyclo[3.1.0]hexan-3-yl}-2-ethenylpyridin-3-yl)methyl]-1H-imidazole-4-carboxylate |
| 6-5 | Ethyl 1-[(6-{3-azabicyclo[3.1.0]hexan-3-yl}-2-formylpyridin-3-yl)methyl]-1H-pyrazole-4-carboxylate | Ethyl 1-[(6-{3-azabicyclo[3.1.0]hexan-3-yl}-2-ethenylpyridin-3-yl)methyl]-1H-pyrazole-4-carboxylate |
| 6-6 | Ethyl 1-[(2-{3-azabicyclo[3.1.0]hexan-3-yl}-4-formylpyrimidin-5-yl)methyl]-1H-imidazole-4-carboxylate | Ethyl 1-[(2-{3-azabicyclo[3.1.0]hexan-3-yl}-4-[(1E)-2-phenylethenyl]pyrimidin-5-yl)methyl]-1H-imidazole-4-carboxylate |
| 6-7 | Ethyl 1-[(6-{6,6-difluoro-3-azabicyclo[3.1.0]hexan-3-yl}-2-formylpyridin-3-yl)methyl]-1H-pyrazole-4-carboxylate | Ethyl 1-[(6-{6,6-difluoro-3-azabicyclo[3.1.0]hexan-3-yl}-2-ethenylpyridin-3-yl)methyl]-1H-pyrazole-4-carboxylate |
| 6-8 | Ethyl 1-[(6-{6,6-difluoro-3-azabicyclo[3.1.0]hexan-3-yl}-2-formylpyridin-3-yl)methyl]-1H-imidazole-4-carboxylate | Ethyl 1-[(6-{6,6-difluoro-3-azabicyclo[3.1.0]hexan-3-yl}-2-ethenylpyridin-3-yl)methyl]-1H-imidazole-4-carboxylate |

Intermediate 7

Ethyl 1-[(6-{5-azaspiro[2.3]hexan-5-yl}-2-(difluoromethyl)pyridin-3-yl)methyl]-1H-pyrazole-4-carboxylate

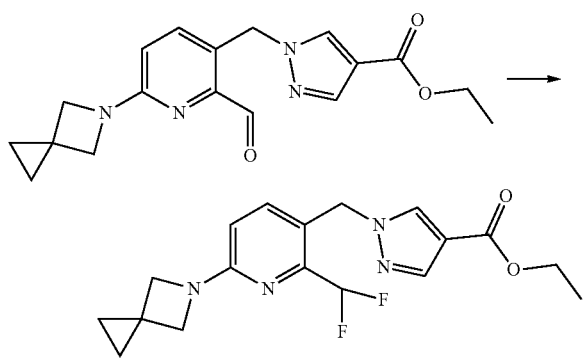

In a microwave vial ethyl 1-[(6-{5-azaspiro[2.3]hexan-5-yl}-2-formylpyridin-3-yl)methyl]-1H-pyrazole-4-carboxylate (584 mg) is dissolved in DCM (7 mL). Diethylaminosulfurtrifluoride (DAST, 700 µL) is added, the vial is sealed and the mixture is heated to 50° C. for 12 h. After cooling to rt the mixture is carefully treated with 1 N aqueous NaHCO₃ until gas evolution has stopped. Then the mixture is partitioned between saturated aqueous NaHCO₃ and DCM. The phases are separated and the aqueous phase is extracted with DCM. The combined organic phases are washed with brine, dried (MgSO₄) and concentrated. The residue is chromatographed on silica gel (petroleum ether/EtOAc 99:1→50:50) to give the title compound. LC (Method 2): $t_R$=1.09 min; Mass spectrum (ESI+): m/z=363 [M+H]⁺.

Intermediates 7-1 to 7-8 are prepared in analogy to Intermediate 7:

| Intermediate | Structure | $t_R$ | Mass spectrum (ESI+): m/z [M + H]⁺ | LC Method |
|---|---|---|---|---|
| 7-1 | 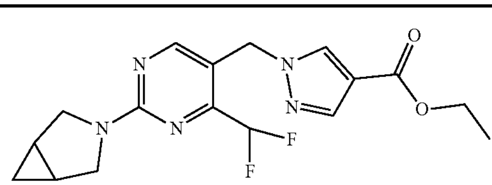 | 1.10 | 364 | Method 2 |

-continued

| Intermediate | Structure | $t_R$ | Mass spectrum (ESI+): m/z [M + H]+ | LC Method |
|---|---|---|---|---|
| 7-2 | 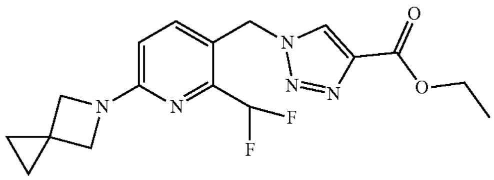 [SMILES: CCOC(=O)c1cn(Cc2ccc(N3CC4(CC4)C3)nc2C(F)F)nn1] | 1.05 | 364 | Method 2 |
| 7-3 | 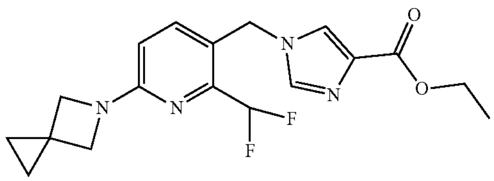 [SMILES: CCOC(=O)c1cn(Cc2ccc(N3CC4(CC4)C3)nc2C(F)F)cn1] | 1.00 | 363 | Method 1 |
| 7-4 | 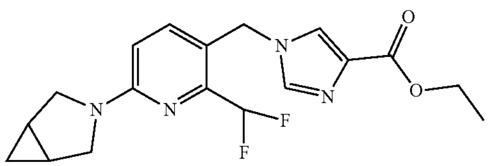 [SMILES: CCOC(=O)c1cn(Cc2ccc(N3CC4CC4C3)nc2C(F)F)cn1] | 1.03 | 363 | Method 1 |
| 7-5 | 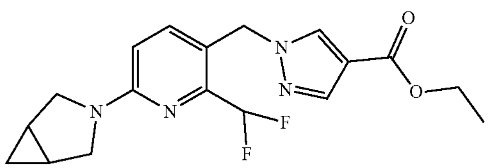 [SMILES: CCOC(=O)c1cnn(Cc2ccc(N3CC4CC4C3)nc2C(F)F)c1] | 1.08 | 363 | Method 2 |
| 7-6 | 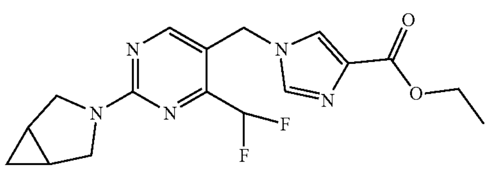 [SMILES: CCOC(=O)c1cn(Cc2cnc(N3CC4CC4C3)nc2C(F)F)cn1] | 0.88 | 364 | Method 2 |
| 7-7 | 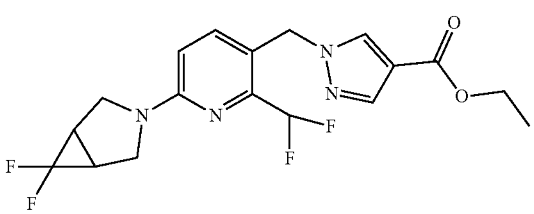 [SMILES: CCOC(=O)c1cnn(Cc2ccc(N3CC4C(C3)C4(F)F)nc2C(F)F)c1] | 1.07 | 399 | Method 1 |
| 7-8 | 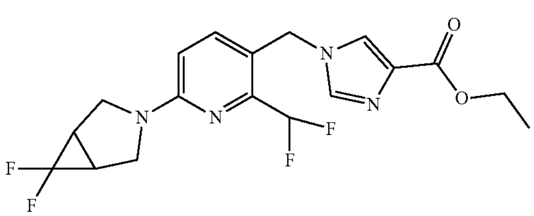 [SMILES: CCOC(=O)c1cn(Cc2ccc(N3CC4C(C3)C4(F)F)nc2C(F)F)cn1] | 0.99 | 399 | Method 1 |

| Intermediate | Name | Name of Starting Material |
|---|---|---|
| 7-1 | Ethyl 1-[(2-{3-azabicyclo[3.1.0]hexan-3-yl}-4-(difluoromethyl)pyrimidin-5-yl)methyl]-1H-pyrazole-4-carboxylate | Ethyl 1-[(2-{3-azabicyclo[3.1.0]hexan-3-yl}-4-formylpyrimidin-5-yl)methyl]-1H-pyrazole-4-carboxylate |
| 7-2 | Ethyl 1-[(6-{5-azaspiro[2.3]hexan-5-yl}-2-(difluoromethyl)pyridin-3-yl)methyl]-1H-1,2,3-triazole-4-carboxylate | Ethyl 1-[(6-{5-azaspiro[2.3]hexan-5-yl}-2-formylpyridin-3-yl)methyl]-1H-1,2,3-triazole-4-carboxylate |

-continued

| Intermediate | Name | Name of Starting Material |
|---|---|---|
| 7-3 | Ethyl 1-[(6-{5-azaspiro[2.3]hexan-5-yl}-2-(difluoromethyl)pyridin-3-yl)methyl]-1H-imidazole-4-carboxylate | Ethyl 1-[(6-{5-azaspiro[2.3]hexan-5-yl}-2-formylpyridin-3-yl)methyl]-1H-imidazole-4-carboxylate |
| 7-4 | Ethyl 1-[(6-{3-azabicyclo[3.1.0]hexan-3-yl}-2-(difluoromethyl)pyridin-3-yl)methyl]-1H-imidazole-4-carboxylate | Ethyl 1-[(6-{3-azabicyclo[3.1.0]hexan-3-yl}-2-formylpyridin-3-yl)methyl]-1H-imidazole-4-carboxylate |
| 7-5 | Ethyl 1-[(6-{3-azabicyclo[3.1.0]hexan-3-yl}-2-(difluoromethyl)pyridin-3-yl)methyl]-1H-pyrazole-4-carboxylate | Ethyl 1-[(6-{3-azabicyclo[3.1.0]hexan-3-yl}-2-formylpyridin-3-yl)methyl]-1H-pyrazole-4-carboxylate |
| 7-6 | Ethyl 1-[(2-{3-azabicyclo[3.1.0]hexan-3-yl}-4(difluoromethyl)pyrimidin-5-yl)methyl]-1H-imidazole-4-carboxylate | Ethyl 1-[(2-{3-azabicyclo[3.1.0]hexan-3-yl}-4-formylpyrimidin-5-yl)methyl]-1H-imidazole-4-carboxylate |
| 7-7 | Ethyl 1-[(6-{6,6-difluoro-3-azabicyclo[3.1.0]hexan-3-yl}-2-(difluoromethyl)pyridin-3-yl)methyl]-1H-pyrazole-4-carboxylate | Ethyl 1-[(6-{6,6-difluoro-3-azabicyclo[3.1.0]hexan-3-yl}-2-formylpyridin-3-yl)methyl]-1H-pyrazole-4-carboxylate |
| 7-8 | Ethyl 1-[(6-{6,6-difluoro-3-azabicyclo[3.1.0]hexan-3-yl}-2-(difluoromethyl)pyridin-3-yl)methyl]-1H-imidazole-4-carboxylate | Ethyl 1-[(6-{6,6-difluoro-3-azabicyclo[3.1.0]hexan-3-yl}-2-formylpyridin-3-yl)methyl]-1H-imidazole-4-carboxylate |

Intermediate 8

1-[(6-{5-Azaspiro[2.3]hexan-5-yl}-2-(difluoromethyl)pyridin-3-yl)methyl]-1H-pyrazole-4-carboxylic acid

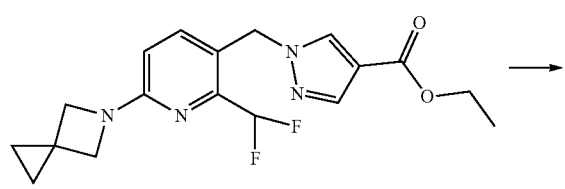

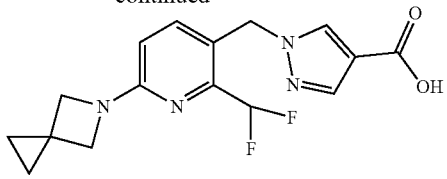

A mixture of ethyl 1-[(6-{5-azaspiro[2.3]hexan-5-yl}-2-(difluoromethyl)pyridin-3-yl)methyl]-1H-pyrazole-4-carboxylate (148 mg), EtOH (3 mL) and NaOH (4 M aqueous solution, 400 µL) is stirred for 48 h at rt. Aqueous HCl (4 M, 400 µL) is added and the mixture is purified by HPLC on reversed phase (ACN, water) to give the title compound.

LC (Method 2): $t_R$=0.93 min; Mass spectrum (ESI+): m/z=335 [M+H]$^+$.

Intermediates 8-1 to 8-10 are prepared in analogy to Intermediate 8:

| | | | Mass spectrum (ESI+): | | |
|---|---|---|---|---|---|
| Intermediate | Structure | | $t_R$ | m/z [M + H]$^+$ | LC Method |
| 8-1 | | | 0.62 | 336 | Method 1 |
| 8-2 | | | 0.95 | 336 | Method 2 |
| 8-3 | | | 0.91 | 336 | Method 2 |

-continued

| Intermediate | Structure | $t_R$ | Mass spectrum (ESI+): m/z [M + H]$^+$ | LC Method |
|---|---|---|---|---|
| 8-4 | 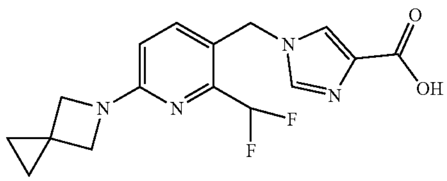 [SMILES: O=C(O)c1cn(Cc2ccc(N3CC4(CC4)C3)nc2C(F)F)cn1] | 0.64 | | Method 1 |
| 8-5 | 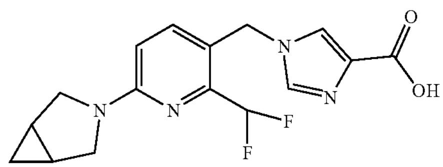 [SMILES: O=C(O)c1cn(Cc2ccc(N3CC4CC4C3)nc2C(F)F)cn1] | 0.66 | 335 | Method 1 |
| 8-6 | 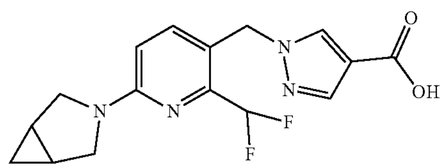 [SMILES: O=C(O)c1cnn(Cc2ccc(N3CC4CC4C3)nc2C(F)F)c1] | 0.66 | 335 | Method 1 |
| 8-7 | 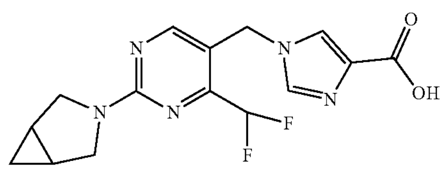 [SMILES: O=C(O)c1cn(Cc2cnc(N3CC4CC4C3)nc2C(F)F)cn1] | 0.67 | 336 | Method 2 |
| 8-8 | 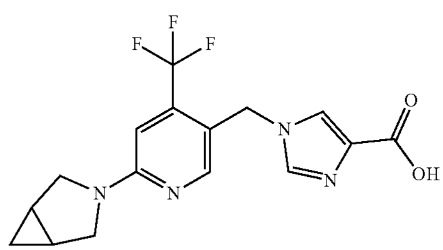 [SMILES: O=C(O)c1cn(Cc2cnc(N3CC4CC4C3)cc2C(F)(F)F)cn1] | 0.71 | 353 | Method 2 |
| 8-9 | 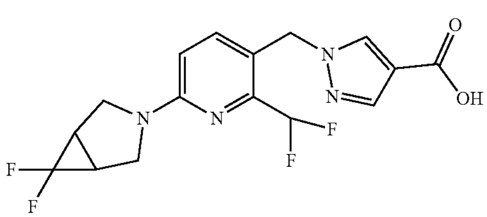 [SMILES: O=C(O)c1cnn(Cc2ccc(N3CC4C(C3)C4(F)F)nc2C(F)F)c1] | 0.65 | 371 | Method 1 |
| 8-10 | 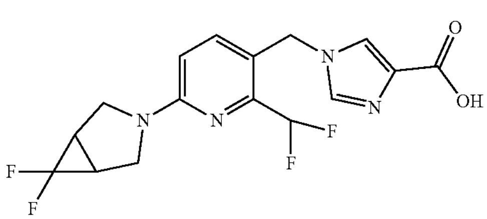 [SMILES: O=C(O)c1cn(Cc2ccc(N3CC4C(C3)C4(F)F)nc2C(F)F)cn1] | 0.65 | 371 | Method 1 |

| Intermediate | Comment on reaction conditions |
|---|---|
| 8-1 | KOH is used instead of NaOH. The reaction is conducted THF/EtOH 4:1 at 50° C. for 48 h. |
| 8-2 | The reaction is conducted in THF/MeOH 1:1 at 70° C. for 1 h. |
| 8-3 | The reaction is conducted in EtOH for 48 h at rt. The product is purified by HPLC on reversed phase (ACN, water). |
| 8-4 | The reaction is conducted in THF/EtOH for 45 minutes at 70° C. |
| 8-5 | The reaction is conducted in THF/EtOH for 40 minutes at 70° C. |
| 8-6 | The reaction is conducted in THF/MeOH 1:1 at 70° C. for 8 h. |
| 8-7 | KOH is used instead of NaOH. The reaction is conducted in THF/EtOH for 4 h at 50° C. |
| 8-8 | The reaction is conducted for 2.5 h at 70° C. |
| 8-9 | The reaction is conducted in THF/EtOH for 2 h at 70° C. |
| 8-10 | The reaction is conducted in THF/EtOH for 45 minutes at 70° C. |

| Intermediate | Name | Name of Starting Material |
|---|---|---|
| 8-1 | 1-[(2-{3-azabicyclo[3.1.0]hexan-3-yl}-4-(difluoromethyl)pyrimidin-5-yl)methyl]-1H-pyrazole-4-carboxylic acid | Ethyl 1-[(2-{3-azabicyclo[3.1.0]hexan-3-yl}-4-(difluoromethyl)pyrimidin-5-yl)methyl]-1H-pyrazole-4-carboxylate |
| 8-2 | 1-[(6-{3-Azabicyclo[3.1.0]hexan-3-yl}-2-(difluoromethyl)pyridin-3-yl)methyl]-1H-1,2,3-triazole-4-carboxylic acid | Ethyl 1-[(6-{3-azabicyclo[3.1.0]hexan-3-yl}-2-(difluoromethyl)pyridin-3-yl)methyl]-1H-1,2,3-triazole-4-carboxylate |
| 8-3 | 1-[(6-{5-Azaspiro[2.3]hexan-5-yl}-2-(difluoromethyl)pyridin-3-yl)methyl]-1H-1,2,3-triazole-4-carboxylic acid | Ethyl 1-[(6-{5-Azaspiro[2.3]hexan-5-yl}-2-(difluoromethyl)pyridin-3-yl)methyl]-1H-1,2,3-triazole-4-carboxylic acid |
| 8-4 | 1-[(6-{5-Azaspiro[2.3]hexan-5-yl}-2-(difluoromethyl)pyridin-3-yl)methyl]-1H-imidazole-4-carboxylic acid | Ethyl 1-[(6-{5-azaspiro[2.3]hexan-5-yl}-2-(difluoromethyl)pyridin-3-yl)methyl]-1H-imidazole-4-carboxylate |
| 8-5 | 1-[(6-{3-Azabicyclo[3.1.0]hexan-3-yl}-2-(difluoromethyl)pyridin-3-yl)methyl]-1H-imidazole-4-carboxylic acid | Ethyl 1-[(6-{3-azabicyclo[3.1.0]hexan-3-yl}-2-(difluoromethyl)pyridin-3-yl)methyl]-1H-imidazole-4-carboxylate |
| 8-6 | 1-[(6-{3-Azabicyclo[3.1.0]hexan-3-yl}-2-(difluoromethyl)pyridin-3-yl)methyl]-1H-pyrazole-4-carboxylic acid | Ethyl 1-[(6-{3-azabicyclo[3.1.0]hexan-3-yl}-2-(difluoromethyl)pyridin-3-yl)methyl]-1H-pyrazole-4-carboxylate |
| 8-7 | 1-[(2-{3-Azabicyclo[3.1.0]hexan-3-yl}-4-(difluoromethyl)pyrimidin-5-yl)methyl]-1H-imidazole-4-carboxylic acid | Ethyl 1-[(2-{3-azabicyclo[3.1.0]hexan-3-yl}-4(difluoromethyl)pyrimidin-5-yl)methyl]-1H-imidazole-4-carboxylate |
| 8-8 | 1-[(6-{3-Azabicyclo[3.1.0]hexan-3-yl}-4-(trifluoromethyl)pyridin-3-yl)methyl]-1H-imidazole-4-carboxylic acid | Ethyl 1-[(6-{3-azabicyclo[3.1.0]hexan-3-yl}-4-(trifluoromethyl)pyridin-3-yl)methyl]-1H-imidazole-4-carboxylate |
| 8-9 | 1-[(6-{6,6-Difluoro-3-azabicyclo[3.1.0]hexan-3-yl}-2-(difluoromethyl)pyridin-3-yl)methyl]-1H-pyrazole-4-carboxylic acid | Ethyl 1-[(6-{6,6-difluoro-3-azabicyclo[3.1.0]-hexan-3-yl}-2-(difluoromethyl)pyridin-3-yl)methyl]-1H-pyrazole-4-carboxylate |
| 8-10 | 1-[(6-{6,6-Difluoro-3-azabicyclo[3.1.0]hexan-3-yl}-2-(difluoromethyl)pyridin-3-yl)methyl]-1H-imidazole-4-carboxylic acid | Ethyl 1-[(6-{6,6-difluoro-3-azabicyclo[3.1.0]-hexan-3-yl}-2-(difluoromethyl)pyridin-3-yl)methyl]-1H-imidazole-4-carboxylate |

Intermediate 9

Ethyl 2-chloro-4-[(1E)-2-phenylethenyl]pyrimidine-5-carboxylate

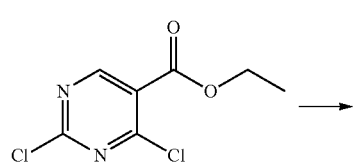
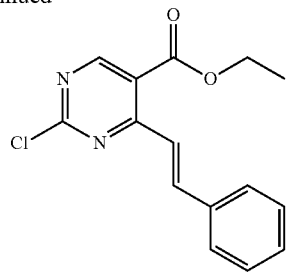

In a microwave vial a mixture of ethyl 2,4-dichloropyrimidine-5-carboxylate (2.5 g), potassium trans-beta-styryl-trifluoroborate (2.5 g), Na$_2$CO$_3$ (2 M aqueous solution, 12.5 mL) and 1,4-dioxane (50 mL) is purged for 10 minutes with argon. Bis(di-tert-butyl(4-dimethylaminophenyl)phosphine)dichloropalladium(II) (Pd(amphos)$_2$Cl$_2$, 300 mg) is added, the vial is sealed and the mixture is heated to 50° C. for 2 h. After cooling to rt the mixture is partitioned between EtOAc and water. The organic phase is washed with brine, dried (MgSO$_4$) and concentrated. The residue is chromatographed on silica gel (petroleum ether/EtOAc 80:20→60:40) to give the title compound.

LC (Method 2): t$_R$=1.21 min; Mass spectrum (ESI+): m/z=289 [M+H]$^+$.

Intermediate 10

Ethyl 2-{3-azabicyclo[3.1.0]hexan-3-yl}-4-[(1E)-2-phenylethenyl]pyrimidine-5-carboxylate

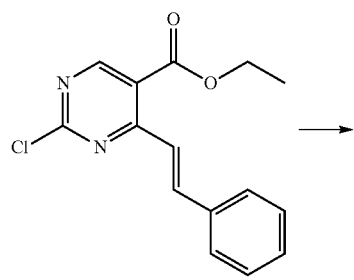

→

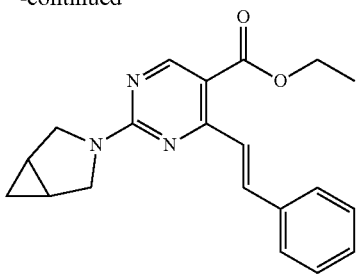

Under argon atmosphere a mixture of ethyl 2-chloro-4-[(1E)-2-phenylethenyl]pyrimidine-5-carboxylate (2.56 g), 3-azabicyclo[3.1.0]hexane hydrochloride (1.3 g) and KHCO$_3$ (2.3 g) in THF (30 mL) is stirred for 12 h at rt. The mixture is partitioned between saturated aqueous NH$_4$Cl and EtOAc and the phases are separated. The organic phase is washed with brine. The organic phase is dried (MgSO$_4$), concentrated and the residue is chromatographed on silica gel (petroleum ether/EtOAc 80:20→60:40) to give the title compound.

LC (Method 2): t$_R$=1.27 min; Mass spectrum (ESI+): m/z=336 [M+H]$^+$.

Intermediate 10-1 is prepared in analogy to Intermediate 10:

| Intermediate | Structure | t$_R$ | m/z [M + H]$^+$ | LC Method |
|---|---|---|---|---|
| 10-1 | ![structure] | 1.07 | 287 | Method 1 |

| Intermediate | Comment on reaction conditions |
|---|---|
| 10-1 | DMSO instead of DMF is used. The reaction is conducted at 45° C. for 4 h. |

| Intermediate Name | Name of Starting Material 1 | Name of Starting Material 2 |
|---|---|---|
| 10-1 Methyl 6-{3-azabicyclo[3.1.0]hexan-3-yl}-4-(trifluoromethyl)pyridine-3-carboxylate | Methyl 6-chloro-4-(trifluoromethyl)pyridine-3-carboxylate | 3-Azabicyclo[3.1.0]hexane hydrochloride |

Intermediate 11

(2-{3-Azabicyclo[3.1.0]hexan-3-yl}-4-[(1E)-2-phenylethenyl]pyrimidin-5-yl)methanol

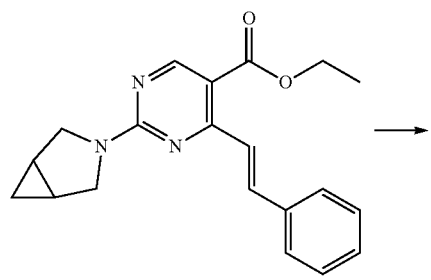

↓

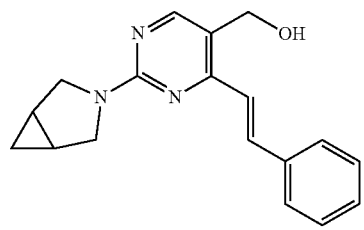

Under argon atmosphere a mixture of ethyl 2-{3-azabicyclo[3.1.0]hexan-3-yl}-4-[(1E)-2-phenylethenyl]pyrimidine-5-carboxylate (1.96 g) in THF (40 mL) is treated dropwise with diisobutylaluminumhydride (DIBAH, 1 M in THF, 25 mL). The mixture is stirred for 2 h at rt, cooled to 0° C. and treated dropwise with 4 M aqueous HCl (15 mL). Then the mixture is stirred for 5 minutes and 4 M aqueous NaOH (15 mL) is added. The mixture is partitioned between brine and DCM and the phases are separated. The organic phase is dried (MgSO$_4$), concentrated and the residue is chromatographed on silica gel (DCM/MeOH 98:2→90:10) to give the title compound.

LC (Method 2): $t_R$=0.84 min; Mass spectrum (ESI+): m/z=294 [M+H]$^+$.

Intermediate 12

Ethyl 1-[(2-{3-azabicyclo[3.1.0]hexan-3-yl}-4-[(1E)-2-phenylethenyl]pyrimidin-5-yl)methyl]-1H-pyrazole-4-carboxylate

↓

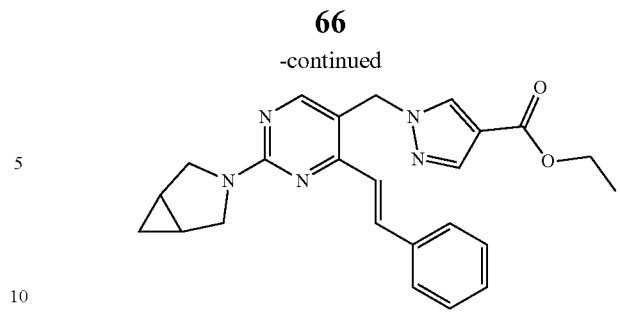

SOCl$_2$ (5 mL) is added under argon atmosphere to a mixture of (2-{3-azabicyclo[3.1.0]hexan-3-yl}-4-[(1E)-2-phenylethenyl]pyrimidin-5-yl)methanol (1.89 g) in toluene (20 mL). The mixture is heated to 60° C. for 3 h, cooled to rt and concentrated in vacuo. The residue is taken up in DCM (20 mL) and added dropwise to a mixture of ethyl 1H-pyrazole-4-carboxylate (950 mg) and DIPEA (2.2 mL) in DCM (20 mL). After stirring for 12 h at rt the mixture is partitioned between water and DCM. The organic phase is washed with brine, dried (MgSO$_4$), concentrated and the residue is chromatographed on silica gel (petroleum ether/EtOAc 50:50→0:100) to give the title compound.

LC (Method 2): $t_R$=1.06 min; Mass spectrum (ESI+): m/z=416 [M+H]$^+$.

Intermediate 13

Ethyl 1-[(6-{3-azabicyclo[3.1.0]hexan-3-yl}-2-(difluoromethyl)pyridin-3-yl)methyl]-1H-1,2,3-triazole-4-carboxylate

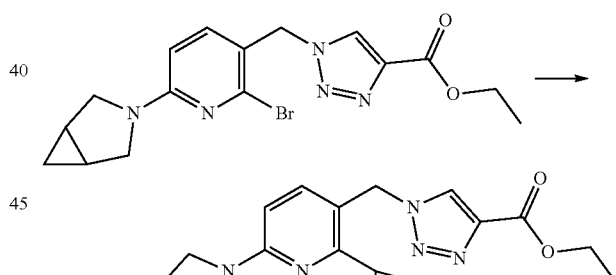

↓

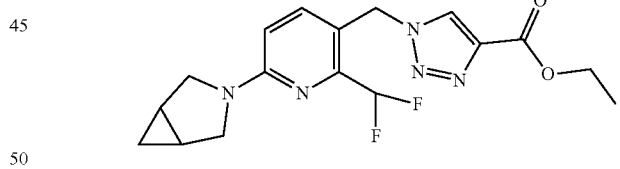

A microwave vial charged with a stir bar, ethyl 1-[(6-{3-azabicyclo[3.1.0]hexan-3-yl}-2-bromopyridin-3-yl)methyl]-1H-1,2,3-triazole-4-carboxylate (300 mg), and NMP (4 mL) is flushed with Ar for 5 min. CsF (349 mg), CuF (146 mg) and difluoromethyl-trimethylsilane (522 µL) are successively added, the vial is sealed, and the mixture is stirred at 120° C. for 1.5 h. After cooling to rt, the mixture is partitioned between water and EtOAc. The mixture is filtered over celite, the phases are separated and the aqueous phase is extracted with EtOAc. The combined organic phases are dried (MgSO$_4$) and concentrated. The residue is purified by HPLC on reversed phase (ACN, water) to give the title compound.

LC (Method 2): $t_R$=1.08 min; Mass spectrum (ESI+): m/z=364 [M+H]$^+$.

Intermediate 14

Ethyl 1-[(6-{5-azaspiro[2.3]hexan-5-yl}-2-ethenylpyridin-3-yl)methyl]-1H-imidazole-4-carboxylate

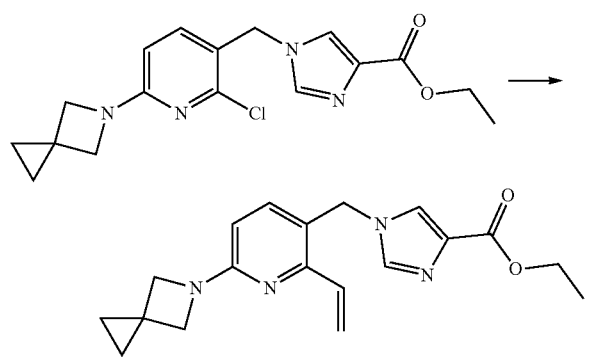

A microwave vial charged with a stir bar, ethyl 1-[(6-{5-azaspiro[2.3]hexan-5-yl}-2-chloropyridin-3-yl)methyl]-1H-imidazole-4-carboxylate (2.6 g), vinylboronic acid pinacolester (1.4 mL), $Na_2CO_3$ (1 M aqueous solution, 18.6 mL), and 1,4-dioxane (40 mL) is purged for 5 minutes with argon. 1,1'-Bis(diphenylphosphino)ferrocenepalladium(II) dichloride (Pd(dppf)Cl$_2$, 304 mg) is added, the vial is sealed, and the mixture is stirred at 100° C. for 6 h. After cooling to rt, the mixture is partitioned between water and EtOAc. The aqueous phase is extracted twice with EtOAc. The combined organic phases are washed with brine, dried (MgSO$_4$), and concentrated. The residue is chromatographed on silica gel (petroleum ether/EtOAc 50:50→0:100) to give the title compound.

LC (Method 1): $t_R$=1.01 min; Mass spectrum (ESI+): m/z=339 [M+H]$^+$.

Intermediates 14-1 to 14-4 are prepared in analogy to Intermediate 14:

| Intermediate | Structure | $t_R$ | Mass spectrum (ESI+): m/z [M + H]$^+$ | LC Method |
|---|---|---|---|---|
| 14-1 | 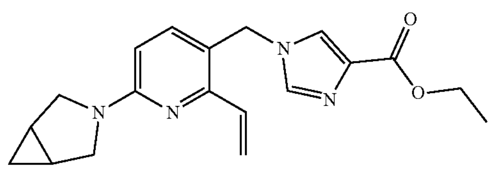 [SMILES: C=Cc1nc(N2CC3CC3C2)ccc1Cn1cnc(C(=O)OCC)c1] | 1.04 | 339 | Method 1 |
| 14-2 | 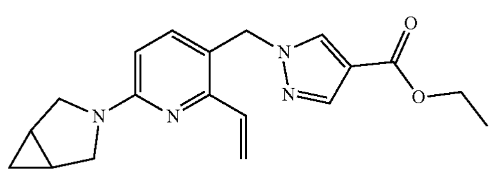 [SMILES: C=Cc1nc(N2CC3CC3C2)ccc1Cn1cc(C(=O)OCC)cn1] | 0.78 | 339 | Method 2 |
| 14-3 | 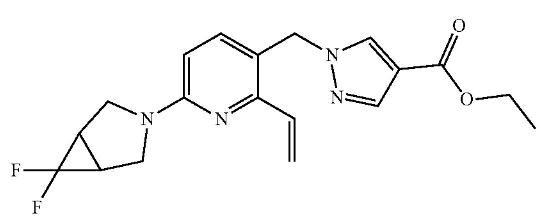 [SMILES: C=Cc1nc(N2CC3C(C2)C3(F)F)ccc1Cn1cc(C(=O)OCC)cn1] | 0.92 | 375 | Method 2 |
| 14-4 | 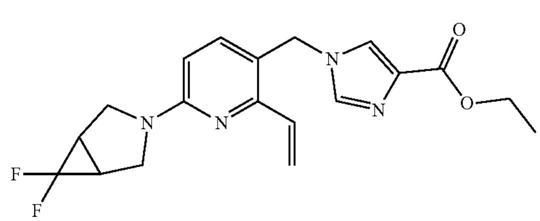 [SMILES: C=Cc1nc(N2CC3C(C2)C3(F)F)ccc1Cn1cnc(C(=O)OCC)c1] | 0.99 | | Method 1 |

| Intermediate | Comment on reaction conditions |
|---|---|
| 14-2 | The reaction is conducted for 12 h at 100° C. |
| 14-3 | The reaction is conducted for 12 h at 100° C. |

| Intermediate | Name | Name of Starting Material |
|---|---|---|
| 14-1 | Ethyl 1-[(6-{3-azabicyclo[3.1.0]hexan-3-yl}-2-ethenylpyridin-3-yl)methyl]-1H-imidazole-4-carboxylate | Ethyl 1-[(6-{3-azabicyclo[3.1.0]hexan-3-yl}-2-chloropyridin-3-yl)methyl]-1H-imidazole-4-carboxylate |
| 14-2 | Ethyl 1-[(6-{3-azabicyclo[3.1.0]hexan-3-yl}-2-ethenylpyridin-3-yl)methyl]-1H-pyrazole-4-carboxylate | Ethyl 1-[(6-{3-azabicyclo[3.1.0]hexan-3-yl}-2-chloropyridin-3-yl)methyl]-1H-pyrazole-4-carboxylate |
| 14-3 | Ethyl 1-[(6-{6,6-difluoro-3-azabicyclo[3.1.0]hexan-3-yl}-2-ethenylpyridin-3-yl)methyl]-1H-pyrazole-4-carboxylate | Ethyl 1-[(2-chloro-6-{6,6-difluoro-3-azabicyclo[3.1.0]hexan-3-yl}pyridin-3-yl)methyl]-1H-pyrazole-4-carboxylate |
| 14-4 | Ethyl 1-[(6-{6,6-difluoro-3-azabicyclo[3.1.0]hexan-3-yl}-2-ethenylpyridin-3-yl)methyl]-1H-imidazole-4-carboxylate | Ethyl 1-[(2-bromo-6-{6,6-difluoro-3-azabicyclo[3.1.0]hexan-3-yl}pyridin-3-yl)methyl]-1H-imidazole-4-carboxylate |

Intermediate 15

(6-{3-Azabicyclo[3.1.0]hexan-3-yl}-4-(trifluoromethyl)pyridin-3-yl)methanol

Intermediate 16

1-[(6-{3-Azabicyclo[3.1.0]hexan-3-yl}-2-(trifluoromethyl)pyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-pyrazole-4-carboxamide

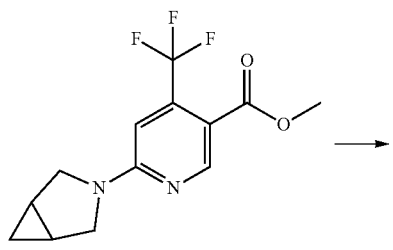

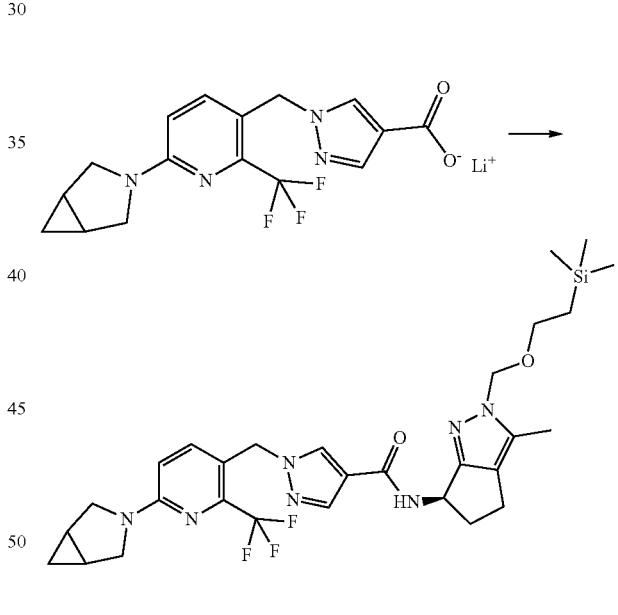

A mixture of methyl 6-{3-azabicyclo[3.1.0]hexan-3-yl}-4-(trifluoromethyl)pyridine-3-carboxylate (1.1 g) in THF (15 mL) is cooled to −50° C. and treated dropwise with LiAlH$_4$ (1 M solution in THF, 3.5 mL). The mixture is stirred for 3 h at −25° C. and then carefully treated with 10% NH$_4$Cl in water. Then the mixture is partitioned between water and EtOAc and filtered over celite. The phases are separated and the aqueous phase is extracted with EtOAc. The combined organic phases are dried (MgSO$_4$) and concentrated in vacuo to give the crude product, which is used directly in the next step.

LC (Method 1): t$_R$=0.93 min; Mass spectrum (ESI+): m/z=259 [M+H]$^+$.

A mixture of 1-[(6-{3-azabicyclo[3.1.0]hexan-3-yl}-2-(trifluoromethyl)pyridin-3-yl)methyl]-1H-pyrazole-4-carboxylic acid, lithium salt (30 mg), DIPEA (90 μL) and O-(7-azabenzotriazol-1-yl)-N,N,N',N'-tetramethyluronium-hexafluorophosphat (HATU, 50 mg) in DMF (2 mL) is stirred for 5 min. (6R)-3-Methyl-2-{[2-(trimethylsilyl)ethoxy]methyl}-2H,4H,5H,6H-cyclopenta[c]pyrazol-6-amine (30 mg) is added and the mixture is stirred for 1 h. The mixture is diluted with EtOAc, washed with water and brine, dried (MgSO$_4$), concentrated in vacuo and the residue is chromatographed on silica gel (DCM/MeOH 98:2→90:10) to give the title compound.

LC (Method 2): t$_R$=1.25 min; Mass spectrum (ESI$^+$): m/z=602 [M+H]$^+$.

Intermediate 17

(6R)-3-Methyl-2-{[2-(trimethylsilyl)ethoxy]methyl}-2H,4H,5H,6H-cyclopenta[c]pyrazol-6-amine

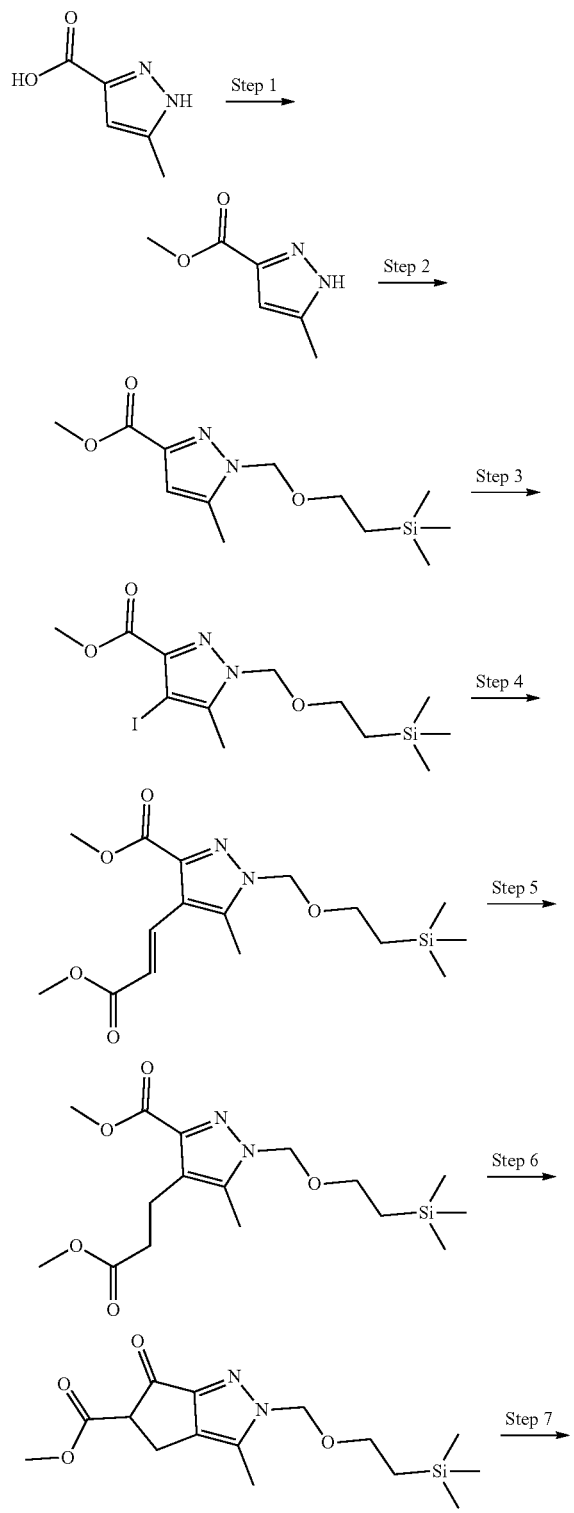

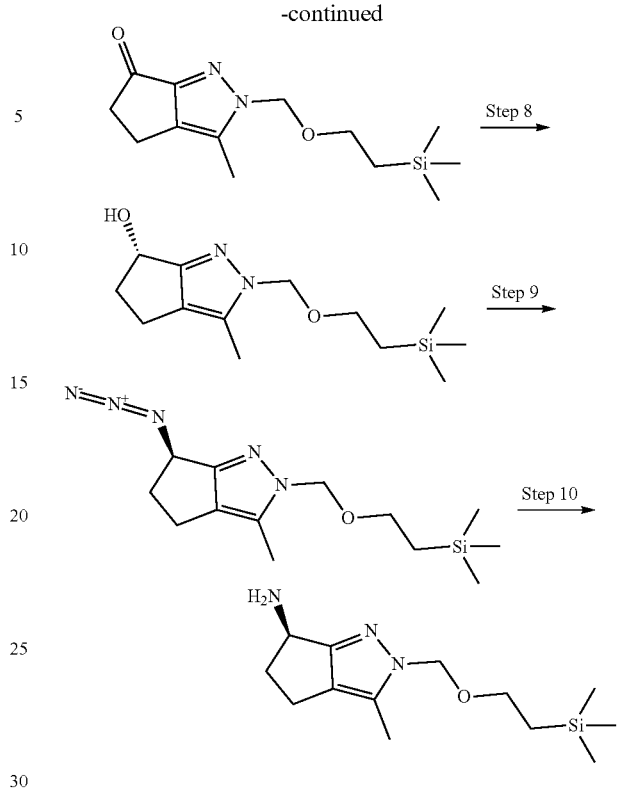

Step 1: Methyl 5-methyl-1H-pyrazole-3-carboxylate

To a solution of 5-methyl-1H-pyrazole-3-carboxylic acid (45 g) in MeOH (450 mL) is added dropwise thionylchloride (58 mL). After addition the mixture is stirred for 16 h at rt. The mixture is concentrated in vacuo. The residue is dissolved in EtOAc, washed successively with saturated aqueous NaHCO$_3$ and brine. After drying (MgSO$_4$) the mixture is concentrated in vacuo to give the title compound.

LC (Method 1): t$_R$=0.64 min; Mass spectrum (ESI$^+$): m/z=141 [M+H]$^+$.

Step 2: Methyl 5-methyl-1-{[2-(trimethylsilyl)ethoxy]methyl}-1H-pyrazole-3-carboxylate Sodium hydride (60% in mineral oil, 16.8 g) is added portionwise to DMF (470 mL). The mixture is stirred for 10 min, cooled to 0° C. and treated dropwise with a solution of methyl 5-methyl-1H-pyrazole-3-carboxylate (46.9 g) in DMF (470 mL). After stirring for 20 min [2-(chloromethoxy)ethyl]trimethylsilane (SEM-CI, 77.7 mL) is added dropwise. The mixture is stirred for 2 h, diluted with EtOAc and washed successively water and brine. After drying (MgSO$_4$) the mixture is concentrated in vacuo and the residue is chromatographed over silica gel with petroleum ether/EtOAc 2:1. The solvents are evaporated in vacuo to give the title compound, which is used directly in the next step.

Step 3: Methyl 4-iodo-5-methyl-1-{[2-(trimethylsilyl)ethoxy]methyl}-1H-pyrazole-3-carboxylate To a solution of methyl 5-methyl-1-{[2-(trimethylsilyl)ethoxy]methyl}-1H-pyrazole-3-carboxylate (94.4 g) in ACN (1.4 L) is added TFA (2.7 mL) and N-iodosuccinimide (94.2 g). The mixture is stirred for 48 h, diluted with EtOAc and washed successively with water, saturated aqueous $Na_2S_2O_3$ and brine. After drying ($MgSO_4$) the mixture is concentrated in vacuo and the residue is chromatographed over silica gel with petroleum ether/EtOAc 2:1. The solvents are evaporated in vacuo to give the title compound, which contains approximately 15% of the regioisomeric methyl 4-iodo-3-methyl-1-{[2-(trimethylsilyl)ethoxy]methyl}-1H-pyrazole-5-carboxylate.

LC (Method 1): $t_R$=1.17 min; Mass spectrum (ESI$^+$): m/z=397 [M+H]$^+$.

Step 4: Methyl 4-[(1E)-3-methoxy-3-oxoprop-1-en-1-yl]-5-methyl-1-{[2-(trimethylsilyl)ethoxy]methyl}-1H-pyrazole-3-carboxylate Methyl 4-iodo-5-methyl-1-{[2-(trimethylsilyl)ethoxy]methyl}-1H-pyrazole-3-carboxylate (44 g), methylacrylate (15 mL) and N-methyldicyclohexylamin (35 mL) are dissolved in dimethylacetamide (430 mL) and water (110 mL). The mixture is purged for 10 min with argon. Dichlorobis(tri-o-tolylphosphine)palladium(II) ($PdCl_2[P(o\text{-}Tol)_3]_2$, 2.6 g) is added and the mixture is stirred for 2 h at 85° C. Then the mixture is diluted with EtOAc and washed successively with 1 M aqueous $H_3PO_4$ and brine. After drying ($MgSO_4$) the mixture is concentrated in vacuo and the residue is chromatographed on silica gel (petroleum ether/EtOAc 95:5→50:50) to give the title compound.

LC (Method 1): $t_R$=1.13 min; Mass spectrum (ESI$^+$): m/z=355 [M+H]$^+$.

Step 5: Methyl 4-(3-methoxy-3-oxopropyl)-5-methyl-1-{[2-(trimethylsilyl)ethoxy]methyl}-1H-pyrazole-3-carboxylate A mixture of methyl 4-[(1E)-3-methoxy-3-oxoprop-1-en-1-yl]-5-methyl-1-{[2-(trimethylsilyl)ethoxy]methyl}-1H-pyrazole-3-carboxylate (38.6 g) and 10% palladium on carbon (5.8 g) in EtOAc (580 mL) is shaken under hydrogen atmosphere (3 bar) at rt for 3 h. The mixture is filtered, and the filtrate is concentrated to give the title compound.

LC (Method 1): $t_R$=1.10 min; Mass spectrum (ESI$^+$): m/z=357 [M+H]$^+$.

Step 6: Methyl 3-methyl-6-oxo-2-{[2-(trimethylsilyl)ethoxy]methyl}-2H,4H,5H,6H-cyclopenta[c]pyrazole-5-carboxylate A solution of methyl 4-(3-methoxy-3-oxopropyl)-5-methyl-1-{[2-(trimethylsilyl)ethoxy]methyl}-1H-pyrazole-3-carboxylate (37.8 g) in THF is cooled to 0° C., treated with $NaN(Si(CH_3)_3)_2$ (40% in THF; 105 mL) and stirred for 15 min. The mixture is poured under ice-cooling and vigorous stirring into 1 M aqueous $H_3PO_4$. The organic phase is separated, washed with brine and dried ($MgSO_4$). The solvents are evaporated in vacuo to give the title compound.

LC (Method 1): $t_R$=1.06 min; Mass spectrum (ESI$^+$): m/z=325 [M+H]$^+$.

Step 7: 3-Methyl-2-{[2-(trimethylsilyl)ethoxy]methyl}-2H,4H,5H,6H-cyclopenta[c]pyrazol-6-one A solution of methyl 3-methyl-6-oxo-2-{[2-(trimethylsilyl)ethoxy]methyl}-2H,4H,5H,6H-cyclopenta[c]pyrazole-5-carboxylate (34.9 g) in 1,4-dioxane (350 mL) and water (9 mL) is heated under reflux for 12 h. The solvents are evaporated in vacuo and the residue is chromatographed on silica gel (petroleum ether/EtOAc 80:20→40:60) to give the title compound. LC (Method 1): $t_R$=1.05 min; Mass spectrum (ESI$^+$): m/z=267 [M+H]$^+$.

Step 8: (6S)-3-Methyl-2-{[2-(trimethylsilyl)ethoxy]methyl}-2H,4H,5H,6H-cyclopenta[c]pyrazol-6-ol To a solution of triethylamine (27 mL) in DCM (260 mL) is added at 0° C. formic acid (11 mL). The mixture is warmed to rt and 3-methyl-2-{[2-(trimethylsilyl)ethoxy]methyl}-2H,4H,5H,6H-cyclopenta[c]pyrazol-6-one (26 g) is added. After purging for 10 min with argon [N-[(1S,2S)-2-(amino-κN)-1,2-diphenylethyl]-4-methylbenzenesulfonamidato-κN]chloro-[(1,2,3,4,5,6-η)-1,3,5-trimethylbenzene]-ruthenium (RuCl[(S,S)-TsDPEN](mesitylene); 0.5 g) is added and the mixture is stirred for 48 h at rt. Then the mixture is treated with 1 M aqueous $NaHCO_3$ under vigorous stirring. The phases are separated and the aqueous phase is extracted with DCM. The combined organic phases are washed with water and brine. After drying ($MgSO_4$), the solvents are evaporated in vacuo and the residue is chromatographed on silica gel (DCM/MeOH 98:2→90:10) to give the title compound with an enantiomeric excess (ee) of 84%.

LC (Method 1): $t_R$=0.99 min; Mass spectrum (ESI$^+$): m/z=269 [M+H]$^+$.

Step 9: (6R)-6-Azido-3-methyl-2-{[2-(trimethylsilyl)ethoxy]methyl}-2H,4H,5H,6H-cyclopenta[c]pyrazole Under argon atmosphere DBU (16 mL) is added to a solution of (6S)-3-methyl-2-{[2-(trimethylsilyl)ethoxy]methyl}-2H,4H,5H,6H-cyclopenta[c]pyrazol-6-ol (25.5 g) in toluene (250 mL). The mixture is cooled to 0° C. and diphenylphosphorylazide (22 mL) is added dropwise over 1 h. The mixture is stirred for 12 h while warming to rt. Then MeOH (25 mL) is added and the mixture is stirred for 1 h. The mixture is washed twice with water, dried ($MgSO_4$) and concentrated in vacuo. The residue is chromatographed on $Al_2O_3$ (DCM) to give the title compound.

LC (Method 1): $t_R$=1.15 min; Mass spectrum (ESI$^+$): m/z=294 [M+H]$^+$.

Step 10: (6R)-3-Methyl-2-{[2-(trimethylsilyl)ethoxy]methyl}-2H,4H,5H,6H-cyclopenta[c]pyrazol-6-amine A mixture of (6R)-6-azido-3-methyl-2-{[2-(trimethylsilyl)ethoxy]methyl}-2H,4H,5H,6H-cyclopenta[c]pyrazole (19.7 g) and 10% palladium on carbon (3 g) in EtOH (200 mL) is shaken under hydrogen atmosphere (3 bar) at rt for 12 h. The mixture is filtered, and the filtrate is concentrated to give the title compound.

LC (Method 1): $t_R$=0.80 min; Mass spectrum (ESI$^+$): m/z=268 [M+H]$^+$.

Synthesis of Examples

Example 1

1-[(6-{5-Azaspiro[2.3]hexan-5-yl}-2-(difluoromethyl)pyridin-3-yl)methyl]-N-[(6R)-3-methyl-2H,4H,5H,6H-cyclopenta[c]pyrazol-6-yl]-1H-pyrazole-4-carboxamide

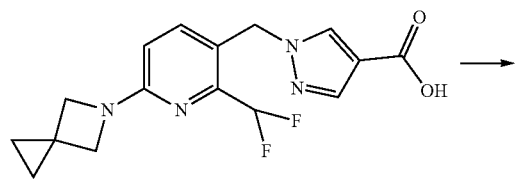
→
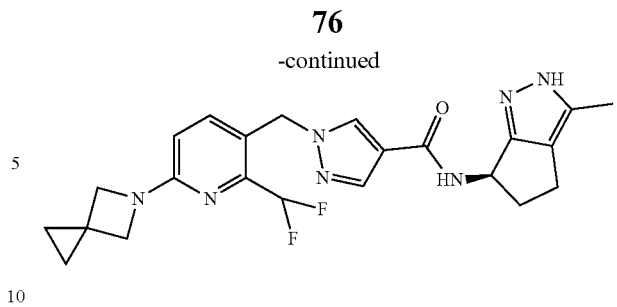

A mixture of 1-[(6-{5-azaspiro[2.3]hexan-5-yl}-2-(difluoromethyl)pyridin-3-yl)methyl]-1H-pyrazole-4-carboxylic acid (110 mg), DIPEA (280 µL) and O-(7-azabenzotriazol-1-yl)-N,N,N',N'-tetramethyluronium-hexafluorophosphat (HATU, 130 mg) in DMF (2 mL) is stirred for 20 min. (6R)-3-Methyl-2H,4H,5H,6H-cyclopenta[c]pyrazol-6-amine; semi-(2S,3S)-2,3-bis(4-methylbenzoyloxy)butanedioic acid (130 mg) is added and the mixture is stirred for 1 h. The mixture is purified by HPLC on reversed phase (ACN, water) to give the title compound.

LC (Method 1): $t_R$=0.97 min; Mass spectrum (ESI$^+$): m/z=454 [M+H]$^+$.

Examples 2 to 12 are prepared in analogy to example 1:

| Example | Structure | $t_R$ | Mass spectrum (ESI+): m/z [M + H]$^+$ | LC Method |
|---|---|---|---|---|
| 2 | 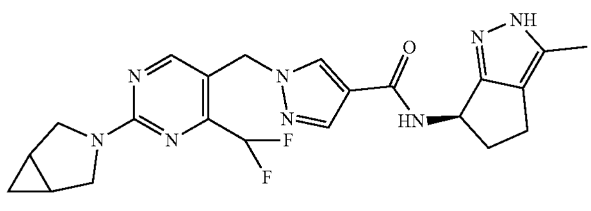 [SMILES: Cc1[nH]nc2c1CC[C@H]2NC(=O)c1cnn(Cc2cnc(N3CC4CC4C3)nc2C(F)F)c1] | 0.87 | 455 | Method 2 |
| 3 | 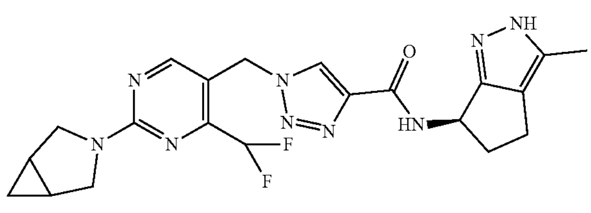 [SMILES: Cc1[nH]nc2c1CC[C@H]2NC(=O)c1cn(Cc2cnc(N3CC4CC4C3)nc2C(F)F)nn1] | 0.93 | 455 | Method 2 |
| 4 | 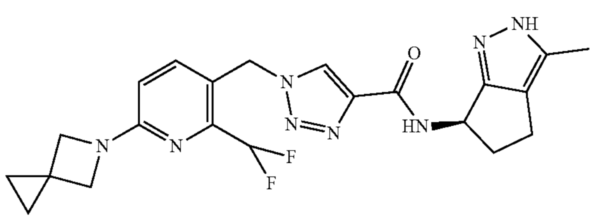 [SMILES: Cc1[nH]nc2c1CC[C@H]2NC(=O)c1cn(Cc2ccc(N3CC4(CC4)C3)nc2C(F)F)nn1] | 0.99 | 455 | Method 1 |
| 5 | 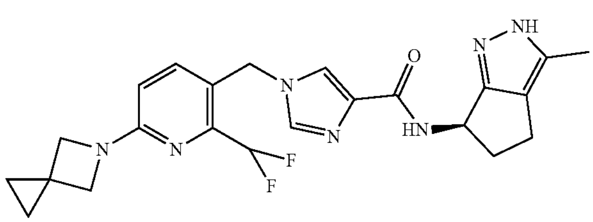 [SMILES: Cc1[nH]nc2c1CC[C@H]2NC(=O)c1cn(Cc2ccc(N3CC4(CC4)C3)nc2C(F)F)cn1] | 0.96 | 454 | Method 1 |

-continued

| Example | Structure | $t_R$ | Mass spectrum (ESI+): m/z [M + H]+ | LC Method |
|---|---|---|---|---|
| 6 | 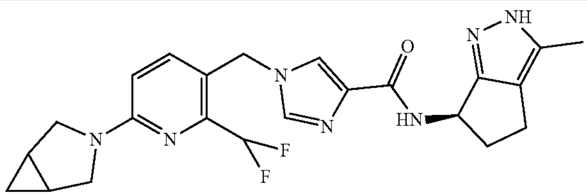 [SMILES: Cc1[nH]nc2c1CC[C@H]2NC(=O)c1cn(Cc2ccc(N3CC4CC4C3)nc2C(F)F)cn1] | 0.99 | 454 | Method 1 |
| 7 | 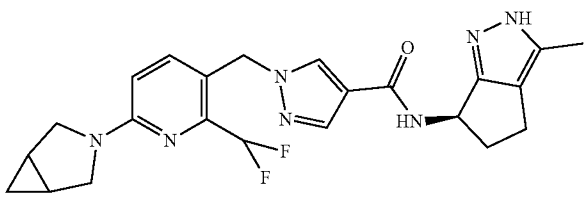 [SMILES: Cc1[nH]nc2c1CC[C@H]2NC(=O)c1cnn(Cc2ccc(N3CC4CC4C3)nc2C(F)F)c1] | 0.99 | 454 | Method 1 |
| 8 | 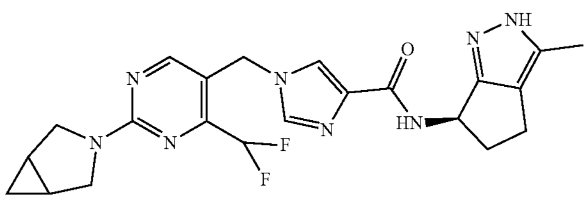 [SMILES: Cc1[nH]nc2c1CC[C@H]2NC(=O)c1cn(Cc2cnc(N3CC4CC4C3)nc2C(F)F)cn1] | 0.81 | 455 | Method 2 |
| 9 | 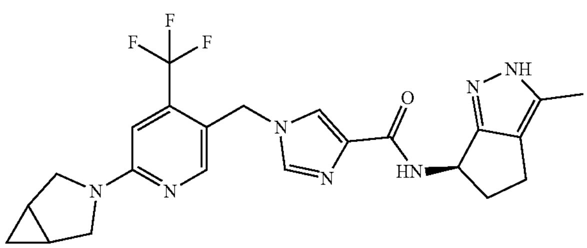 [SMILES: Cc1[nH]nc2c1CC[C@H]2NC(=O)c1cn(Cc2cnc(N3CC4CC4C3)cc2C(F)(F)F)cn1] | 0.97 | 472 | Method 1 |
| 10 | 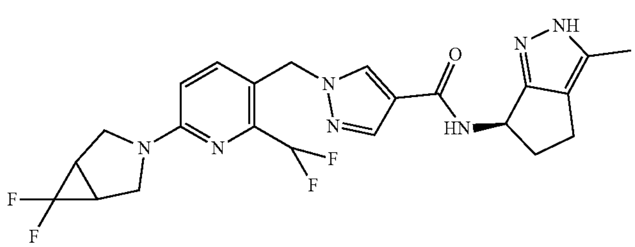 [SMILES: Cc1[nH]nc2c1CC[C@H]2NC(=O)c1cnn(Cc2ccc(N3CC4C(C3)C4(F)F)nc2C(F)F)c1] | 0.96 | 490 | Method 1 |
| 11 | 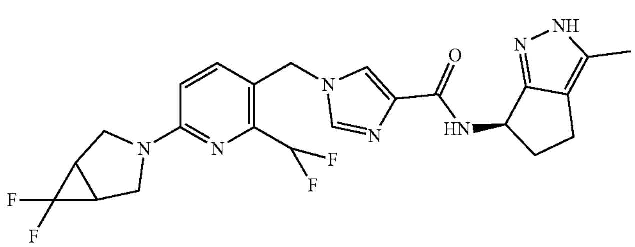 [SMILES: Cc1[nH]nc2c1CC[C@H]2NC(=O)c1cn(Cc2ccc(N3CC4C(C3)C4(F)F)nc2C(F)F)cn1] | 0.96 | 490 | Method 1 |
| 12 | 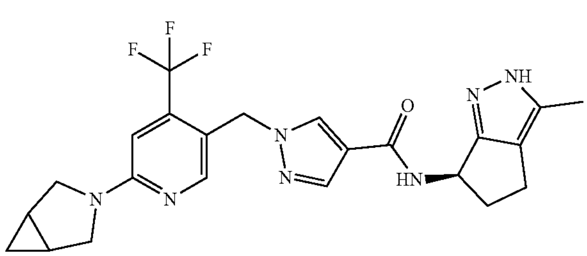 [SMILES: Cc1[nH]nc2c1CC[C@H]2NC(=O)c1cnn(Cc2cnc(N3CC4CC4C3)cc2C(F)(F)F)c1] | 0.97 | 472 | Method 1 |

| Example | Name | Name of Starting Material |
|---|---|---|
| 2 | 1-[(2-{3-Azabicyclo[3.1.0]hexan-3-yl}-4-(difluoromethyl)-pyrimidin-5-yl)methyl]-N-[(6R)-3-methyl-2H,4H,5H,6H-cyclopenta[c]pyrazol-6-yl]-1H-pyrazole-4-carboxamide | 1-[(2-{3-Azabicyclo[3.1.0]hexan-3-yl}-4-difluoromethyl)pyrimidin-5-yl)methyl]-1H-pyrazole-4-carboxylic acid |
| 3 | 1-[(6-{3-Azabicyclo[3.1.0]hexan-3-yl}-2-(difluoromethyl)-pyridin-3-yl)methyl]-N-[(6R)-3-methyl-2H,4H,5H,6H-cyclopenta[c]pyrazol-6-yl]-1H-1,2,3-triazole-4-carboxamide | 1-[(6-{3-Azabicyclo[3.1.0]hexan-3-yl}-2-(difluoromethyl)pyridin-3-yl)methyl]-1H-1,2,3-triazole-4-carboxylic acid |
| 4 | 1-[(6-{5-Azaspiro[2.3]hexan-5-yl}-2-(difluoromethyl)pyridin-3-yl)methyl]-N-[(6R)-3-methyl-2H,4H,5H,6H-cyclopenta[c]-pyrazol-6-yl]-1H-1,2,3-triazole-4-carboxamide | 1-[(6-{5-Azaspiro[2.3]hexan-5-yl}-2-(difluoromethyl)pyridin-3-yl)methyl]-1H-1,2,3-triazole-4-carboxylic acid |
| 5 | 1-[(6-{5-Azaspiro[2.3]hexan-5-yl}-2-(difluoromethyl)-pyridin-3-yl)methyl]-N-[(6R)-3-methyl-2H,4H,5H,6H-cyclopenta[c]pyrazol-6-yl]-1H-imidazole-4-carboxamide | 1-[(6-{5-Azaspiro[2.3]hexan-5-yl}-2-(difluoromethyl)pyridin-3-yl)methyl]-1H-imidazole-4-carboxylic acid |
| 6 | 1-[(6-{3-Azabicyclo[3.1.0]hexan-3-yl}-2-(difluoromethyl)-pyridin-3-yl)methyl]-N-[(6R)-3-methyl-2H,4H,5H,6H-cyclopenta[c]pyrazol-6-yl]-1H-imidazole-4-carboxamide | 1-[(6-{3-Azabicyclo[3.1.0]hexan-3-yl}-2-(difluoromethyl)pyridin-3-yl)methyl]-1H-imidazole-4-carboxylic acid |
| 7 | 1-[(6-{3-Azabicyclo[3.1.0]hexan-3-yl}-2-(difluoromethyl)-pyridin-3-yl)methyl]-N-[(6R)-3-methyl-2H,4H,5H,6H-cyclopenta[c]pyrazol-6-yl]-1H-pyrazole-4-carboxamide | 1-[(6-{3-Azabicyclo[3.1.0]hexan-3-yl}-2-(difluoromethyl)pyridin-3-yl)methyl]-1H-pyrazole-4-carboxylic acid |
| 8 | 1-[(2-{3-Azabicyclo[3.1.0]hexan-3-yl}-4-(difluoromethyl)-pyrimidin-5-yl)methyl]-N-[(6R)-3-methyl-2H,4H,5H,6H-cyclopenta[c]pyrazol-6-yl]-1H-imidazole-4-carboxamide | 1-[(2-{3-Azabicyclo[3.1.0]hexan-3-yl}-4-(difluoromethyl)pyrimidin-5-yl)-methyl]-1H-imidazole-4-carboxylic acid |
| 9 | 1-[(6-{3-Azabicyclo[3.1.0]hexan-3-yl}-4-(trifluoromethyl)-pyridin-3-yl)methyl]-N-[(6R)-3-methyl-2H,4H,5H,6H-cyclopenta[c]pyrazol-6-yl]-1H-imidazole-4-carboxamide | 1-[(6-{3-Azabicyclo[3.1.0]hexan-3-yl}-4-(trifluoromethyl)pyridin-3-yl)methyl]-1H-imidazole-4-carboxylic acid |
| 10 | 1-[(6-{6,6-Difluoro-3-azabicyclo[3.1.0]hexan-3-yl}-2-(difluoromethyl)pyridin-3-yl)methyl]-N-[(6R)-3-methyl-2H,4H,5H,6H-cyclopenta-[c]pyrazol-6-yl]-1H-pyrazole-4-carboxamide | 1-[(6-{6,6-Difluoro-3-azabicyclo[3.1.0]hexan-3-yl}-2-(difluoromethyl)pyridin-3-yl)methyl]-1H-pyrazole-4-carboxylic acid |
| 11 | 1-[(6-{6,6-Difluoro-3-azabicyclo[3.1.0]hexan-3-yl}-2-(difluoromethyl)pyridin-3-yl)methyl]-N-[(6R)-3-methyl-2H,4H,5H,6H-cyclopenta-[c]pyrazol-6-yl]-1H-imidazole-4-carboxamide | 1-[(6-{6,6-Difluoro-3-azabicyclo[3.1.0]hexan-3-yl}-2-(difluoromethyl)pyridin-3-yl)methyl]-1H-imidazole-4-carboxylic acid |
| 12 | 1-[(6-{3-Azabicyclo[3.1.0]hexan-3-yl}-4-(trifluoromethyl)-pyridin-3-yl)methyl]-N-[(6R)-3-methyl-2H,4H,5H,6H-cyclopenta[c]pyrazol-6-yl]-1H-pyrazole-4-carboxamide | 1-[(6-{3-Azabicyclo[3.1.0]hexan-3-yl}-4-(trifluoromethyl)pyridin-3-yl)methyl]-1H-pyrazole-4-carboxylic acid, lithium salt |

Example 13

1-[(6-{3-Azabicyclo[3.1.0]hexan-3-yl}-2-(trifluoromethyl)pyridin-3-yl)methyl]-N-[(6R)-3-methyl-2H,4H,5H,6H-cyclopenta[c]pyrazol-6-yl]-1H-pyrazole-4-carboxamide

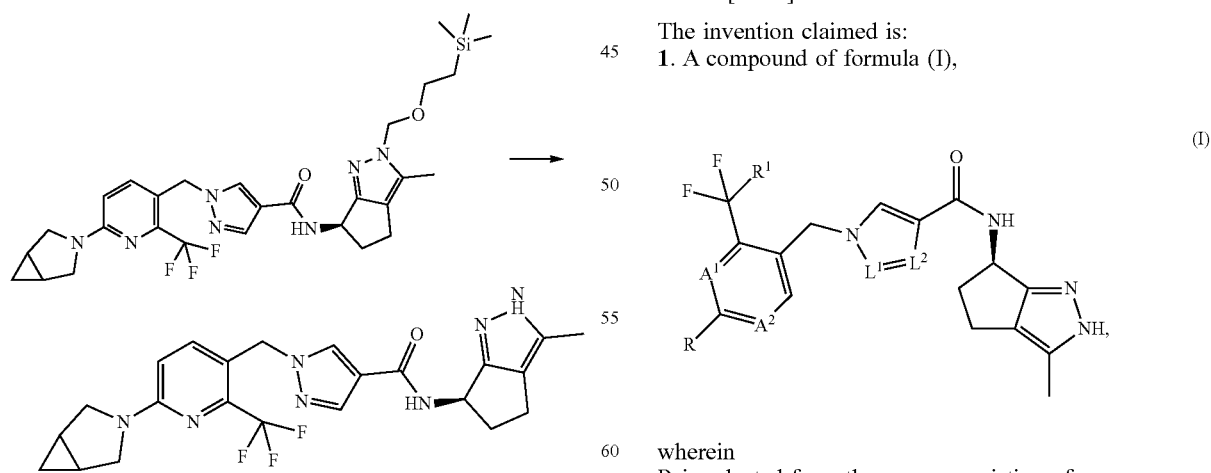

A mixture of 1-[(6-{3-azabicyclo[3.1.0]hexan-3-yl}-2-(trifluoromethyl)pyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-pyrazole-4-carboxamide (45 mg) and trifluoroacetic acid (1 mL) in DCM (2 mL) is stirred for 12 h at rt. The mixture is concentrated in vacuo, taken up in MeOH (2 mL) and treated with a solution of $NH_3$ in MeOH (7 M, 5 mL). The mixture is transferred to a microwave vial. The vial is sealed and the mixture is heated for 12 h to 80° C. After cooling to rt, the mixture is concentrated in vacuo and purified by HPLC on reversed phase (ACN, water) to give the title compound.

LC (Method 3): $t_R$=1.25 min; Mass spectrum (ESI$^+$): m/z=602 [M+H]$^+$.

The invention claimed is:

1. A compound of formula (I),

wherein
R is selected from the group consisting of

-continued

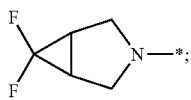

R¹ is selected from the group consisting of H and F;
the moiety =A¹-CR=A²- is selected from the group consisting of =N—CR=N—, =N—CR=CH— and =CH—CR=N—; and
the moiety -L¹=L²- is selected from the group consisting of —N=N—, —N=CH— and —CH=N—;
and/or its tautomers
or a pharmaceutically acceptable salt thereof.

2. The compound according to claim 1,
wherein R is

and/or its tautomers
or a pharmaceutically acceptable salt thereof.

3. The compound according to claim 1,
wherein R is

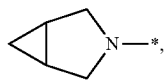

and/or its tautomers
or a pharmaceutically acceptable salt thereof.

4. The compound according to claim 1,
wherein R is

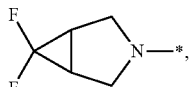

and/or its tautomers
or a pharmaceutically acceptable salt thereof.

5. The compound according to claim 1,
the moiety =A¹-CR=A²- is =N—CR=N—,
and/or its tautomers
or a pharmaceutically acceptable salt thereof.

6. The compound according to claim 1,
the moiety =A¹-CR=A²- is =N—CR=CH—,
and/or its tautomers
or a pharmaceutically acceptable salt thereof.

7. The compound according to claim 1,
the moiety =A¹-CR=A²- is =CH—CR=N—,
and/or its tautomers
or a pharmaceutically acceptable salt thereof.

8. The compound according to claim 1, wherein
the compound of formula (I) is selected from the group consisting of

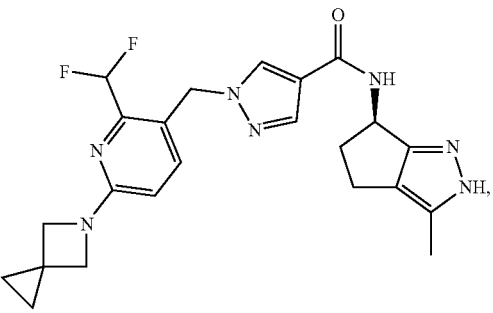

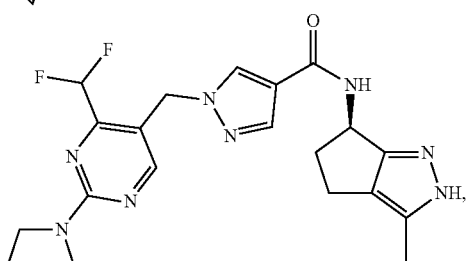

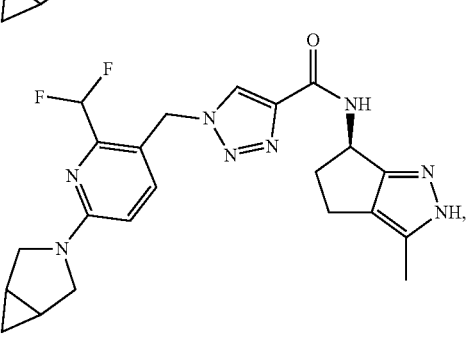

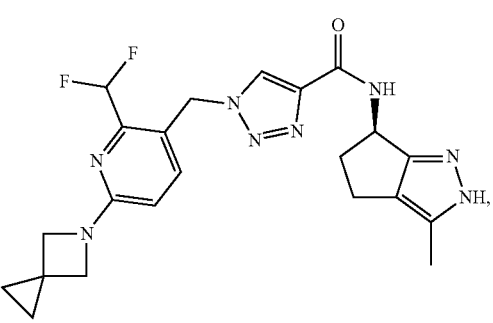

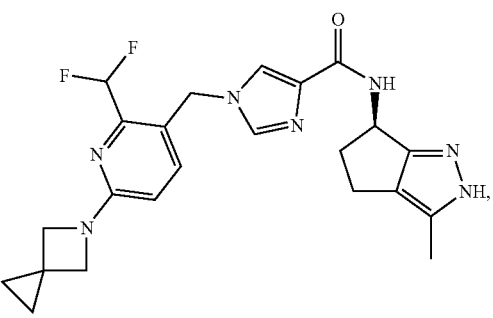

83
-continued

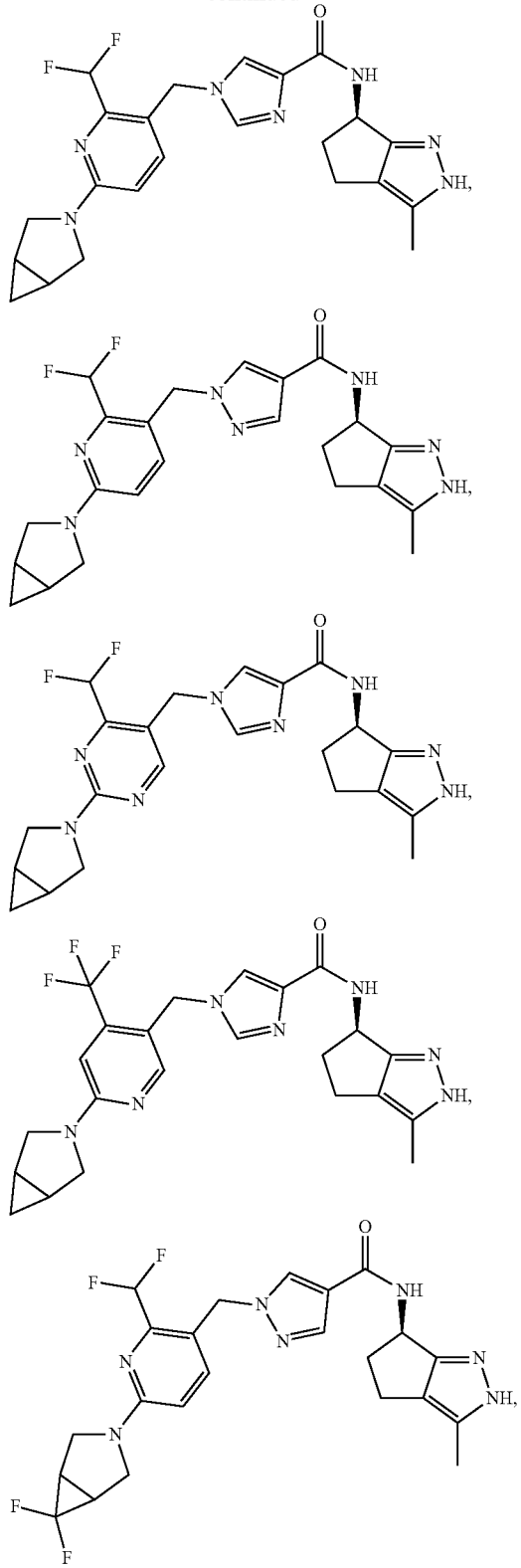

84
-continued

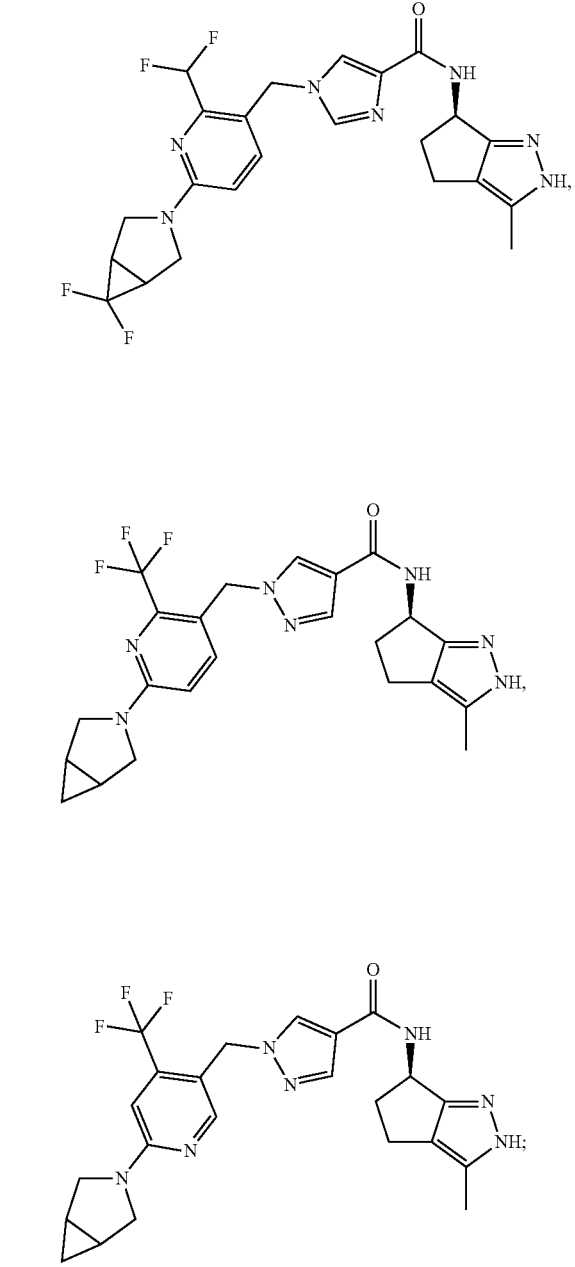

and/or its tautomers
or a pharmaceutically acceptable salt thereof.

9. A pharmaceutically acceptable salt of the compound according to claim 1 and/or its tautomers.

10. A pharmaceutical composition comprising one or more compounds according to claim 1 and/or their tautomers, or pharmaceutically acceptable salts thereof, optionally together with one or more inert carriers and/or diluents.

* * * * *